United States Patent
Chen et al.

(10) Patent No.: US 11,938,105 B1
(45) Date of Patent: *Mar. 26, 2024

(54) METHODS AND COMPOSITIONS FOR THE TREATMENT OF CANCER CACHEXIA

(71) Applicant: Ohio State Innovation Foundation, Columbus, OH (US)

(72) Inventors: Ching-Shih Chen, Columbus, OH (US); Christopher C. Coss, Columbus, OH (US); Samuel Kulp, Columbus, OH (US); Yu-Chou Tseng, Columbus, OH (US); Tanios Bekaii-Saab, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/067,924

(22) Filed: Dec. 19, 2022

Related U.S. Application Data

(63) Continuation of application No. 16/646,424, filed as application No. PCT/US2018/050928 on Sep. 13, 2018, now Pat. No. 11,529,323.

(60) Provisional application No. 62/558,228, filed on Sep. 13, 2017.

(51) Int. Cl.
*A61K 31/167* (2006.01)
*A61K 45/06* (2006.01)
*A61P 21/06* (2006.01)

(52) U.S. Cl.
CPC ............ *A61K 31/167* (2013.01); *A61K 45/06* (2013.01); *A61P 21/06* (2018.01)

(58) Field of Classification Search
CPC ...................................................... A61P 21/06
See application file for complete search history.

(56) References Cited

U.S. PATENT DOCUMENTS

| 2006/0229237 A1 | 10/2006 | Chung et al. |
| 2011/0237664 A1 | 9/2011 | Dalton |
| 2017/0217903 A1 | 8/2017 | Qin et al. |

FOREIGN PATENT DOCUMENTS

| EP | 3071196 A1 | 9/2016 |
| WO | 2005120483 A2 | 12/2005 |
| WO | 2015077353 A1 | 5/2015 |
| WO | 2017030892 A1 | 2/2017 |

OTHER PUBLICATIONS

Search Report issued by the European Patent Office for application EP18856027, dated May 7, 2021.

(Continued)

*Primary Examiner* — Savitha M Rao
*Assistant Examiner* — Andrew P Lee
(74) *Attorney, Agent, or Firm* — Thomas | Horstemeyer, LLP

(57) ABSTRACT

In one aspect, the disclosure relates to methods and compositions for treatment of cancer cachexia. In a further aspect, the composition is a pharmaceutical composition comprising a class I/IIB HDAC inhibitor and an androgen. In a still further aspect, the method of treatment comprises administering a class I/IIB HDAC inhibitor and an androgen to a subject or patient who has been diagnosed as having cancer cachexia. In some aspects, the class I/IIB HDAC inhibitor is a compound known as AR-42.

3 Claims, 60 Drawing Sheets

(56) References Cited

OTHER PUBLICATIONS

Tseng, et al., "Preclinical investigation of the novel histone deacetylase (HDAC) inhibitor AR-42 in the treatment of cancer-induced cachexia", Proceedings: AACR Annual Meeting 2014; Apr. 5-9, 2014; San Diego, CA, vol. 74, No. 19.
Srinath, Enobosarm, "(GTx-024, S-22): a potential treatment for cachexia," Future Oncology, vol. 10, No. 2 (2014), pp. 187-194.

|  | Isoform | % inhib. at 1 μM |
|---|---|---|
| Class I | HDAC1 | 95 |
|  | HDAC2 | 72 |
|  | HDAC3 | 93 |
|  | HDAC8 | 87 |
| Class IIa | HDAC4 | 21 |
|  | HDAC5 | 0 |
|  | HDAC7 | 22 |
|  | HDAC9 | 41 |
| Class IIb | HDAC6 | 100 |
|  | HDAC10 | 86 |

| pg/ml | Tumor-free mice | | C-26 Tumor-bearing mice | | | |
|---|---|---|---|---|---|---|
| | Vehicle | GTx-024 | Vehicle | GTx-024 | AR-42 | Combo |
| G-CSF | 248.66 ± 64.60* | 338.39 ± 71.70* | 12164.11 ± 18944.48 | 2446.63 ± 1625.70* | 2782.18 ± 2191.30 | 1674.20 ± 1160.74* |
| GM-CSF | 18.71 ± 5.56 | 13.27 ± 4.62* | 21.92 ± 5.36 | 17.35 ± 4.33 | 18.70 ± 3.77 | 20.58 ± 5.40 |
| IL-6 | 3.35 ± 1.51* | 2.45 ± 1.31* | 537.66 ± 417.18 | 397.54 ± 341.43 | 256.59 ± 183.1 | 448.16 ± 294.52 |
| IL-17 | 3.04 ± 2.26 | 5.01 ± 1.18* | 1.30 ± 0.57 | 1.75 ± 1.28 | 1.82 ± 0.85 | 2.11 ± 1.21 |
| IP-10 | 162.64 ± 43.04 | 145.68 ± 48.83* | 238.29 ± 124.78 | 154.76 ± 17.98* | 215.35 ± 52.46 | 227.77 ± 45.23 |
| KC | 65.92 ± 26.47 | 90.02 ± 17.69 | 326.10 ± 215.79 | 288.89 ± 154.46 | 363.38 ± 200.65 | 1094.01 ± 528.53* |
| LIF | 2.03 ± 2.17* | 2.50 ± 2.34 | 24.51 ± 11.26 | 45.26 ± 21.57* | 15.79 ± 5.15 | 28.08 ± 21.16 |
| M-CSF | 47.72 ± 27.44* | 27.23 ± 10.09 | 23.63 ± 8.29 | 22.23 ± 9.45 | 20.21 ± 4.63 | 21.00 ± 4.19 |

FIG. 4A

| Dose (mg/kg) | Tissue | $C_{max}$ (nM) | $AUC_{all}$ (nM*h) | $C_{avg}$ (nM) |
| --- | --- | --- | --- | --- |
| 10 | Plasma | 1,501.6 | 10,931.6 | 455.5 |
| 10 | Muscle | 1,109.5 | 11,076.7 | 461.5 |
| 20 | Plasma | 3,858.9 | 34,369.3 | 1,432.1 |
| 20 | Muscle | 3,662.4 | 36,504.2 | 1,521.0 |
| 50 | Plasma | 7,925.1 | 74,307.3 | 3,096.1 |
| 50 | Muscle | 6,367.0 | 72,624.7 | 3,026.2 |

FIG. 7

METHODS AND COMPOSITIONS FOR THE TREATMENT OF CANCER CACHEXIA

CROSS-REFERENCE TO RELATED APPLICATIONS

This application is a continuation of Ser. No. 16/646,424 filed Mar. 11, 2020, which is a National Stage of International Application No. PCT/US2018/050928, filed Sep. 13, 2018, which claims benefit of U.S. Provisional Application No. 62/558,228, filed Sep. 13, 2017, which are all incorporated herein by reference in their entireties.

STATEMENT REGARDING FEDERALLY SPONSORED RESEARCH

This disclosure was made with Government Support under Grant No. CA133250 and Grant No. CA016058 awarded by the National Institutes of Health. The Government has certain rights in the disclosure.

BACKGROUND

Cancer cachexia is a multifactorial syndrome characterized by the involuntary loss of muscle mass occurring with or without concurrent losses in adipose tissue. Cachexia is distinct from simple starvation in that it is not reversible with nutritional support and the accompanying progressive loss of lean mass is associated with decreased quality of life, decreased tolerance of chemotherapy and reduced overall survival. It is estimated that 50-80% of all cancer patients experience cachexia symptoms and up to 20% of all cancer related deaths are attributable to complications arising from cachexia-mediated functional decline. A multitude of tumor and host factors are recognized as contributing to the multi-organ system dysfunction in cancer cachexia which presents a considerable therapeutic challenge. Diverse cachexia treatment strategies have been evaluated in patients with few offering effective palliation and none gaining FDA approval for this devastating consequence of advanced malignancy. Among the complex sequelae associated with cachectic progression, compromised muscle function associated with reduced muscle mass is viewed as a primary contributor patient morbidity and mortality. Recognizing this feature of cancer cachexia, regulatory agencies require the demonstration of meaningful improvements in physical function in addition to improvements in patient body composition for successful registration of novel cachexia therapies. Anabolic Androgenic Steroids (AAS) or steroidal androgens are among the most well recognized function promoting therapies and as such have been extensively evaluated in muscle wasting of diverse etiology. Despite meeting FDA approval criteria in other wasting diseases, steroidal androgens are yet to demonstrate clinical benefit in cancer cachexia. The continued pursuit of novel androgens for the treatment of wasting diseases suggests confidence in this therapeutic strategy remains.

In addition to their well characterized anabolic effects on skeletal muscle, steroidal androgens elicit a number of undesirable virilizing side effects and can promote prostatic hypertrophy which limits their wide spread clinical use. Recently developed, non-steroidal, selective androgen receptor modulators (SARMs) offer a number of improvements over steroidal androgens including prolonged plasma exposures and orally bioavailability with greatly reduced side effects (virilization, etc.) while maintaining full agonism in anabolic tissues like skeletal muscle. With once daily dosing, the SARM GTx-024 (Enobosarm) showed promising gains in fat free mass in both male and female cancer patients but ultimately failed to demonstrate a clear functional benefit in pivotal Phase III trials in a cachectic non-small cell lung cancer (NSCLC) population. GTx-024 has a strong safety profile and proven effects on skeletal muscle but is no longer being developed for cancer cachexia.

Hypogonadism is a feature of advanced malignancy and experimental cachexia leading to a worsening of multiple cachectic sequelae including decreased skeletal muscle mass. Though the relationship between androgen status and body composition is well established the exact molecular means by which androgens modulate skeletal muscle mass is complex and poorly understood. The direct stimulation of muscle precursor cells, reduced expression of several atrogenes, and indirect hypertrophic signaling through multiple pathways all appear to play a role.

Strong evidence supports the importance of indirect IGF-PI3K-Akt cross-talk as muscle stem cell specific androgen receptor knock-out (ARKO) animals have reduced skeletal muscle mass but respond to both orchiectomy and administration of GTx-024. Furthermore, skeletal muscle atrophy induced by either orchiectomy or glucocorticoid administration is associated with suppression of the IGF-PI3K-Akt pathway that is reversible by androgen administration. Androgens have also been directly linked to myostatin signaling which itself has a well characterized role in governing skeletal muscle size.

The effectiveness of a novel class I/IIB HDAC inhibitor (HDACi, AR-42) was recently demonstrated, and AR-42 is currently under clinical evaluation in hematologic malignancy, as anti-cachexia therapy in the C26 mouse model of cancer cachexia. AR-42 administration completely spared body weight and was associated with improvements, but not complete rescue, of skeletal muscle mass relative to controls. Mechanistic studies revealed a number of potentially causative metabolic changes in addition to complete suppression of tumor induced muscle specific E3-ligase expression (Atrogin-1 and MuRF1). AR-42 differed from other approved HDACi's in its ability to fully suppress tumor mediated ligase induction and prolong survival in the C26 model. However, AR-42's effects on skeletal muscle mass, and to a lesser degree muscle function, diminished with delayed treatment suggesting AR-42's anti-catabolic activity is central to its anti-cachectic activity and its ability to restore muscle mass once lost is limited.

Despite advances in research directed to therapeutic intervention for cancer cachexia, there is still a scarcity of therapeutic approaches for efficacious treatment of cancer cachexia. These needs and other needs are satisfied by the present disclosure.

SUMMARY

In accordance with the purpose(s) of the disclosure, as embodied and broadly described herein, the disclosure, in one aspect, relates to compositions comprising an HDAC inhibitor and an androgen or SARM, pharmaceutical compositions comprising same, methods of administering the combination of therapeutic agents to a subject in need thereof. In some aspects, the subject can have a muscle wasting disease, including, but not limited to, cancer cachexia.

Disclosed are compositions comprising an HDAC inhibitor, or a pharmaceutically acceptable salt, hydrate, solvate, or polymorph thereof, and an androgen receptor modulator, or a pharmaceutically acceptable salt, hydrate, solvate, or polymorph thereof.

Also disclosed are pharmaceutical compositions comprising a therapeutically effective amount of a class I/II B HDAC inhibitor, or a pharmaceutically acceptable salt, hydrate, solvate, or polymorph thereof, and an androgen receptor modulator, or a pharmaceutically acceptable salt, hydrate, solvate, or polymorph thereof, and a pharmaceutically acceptable carrier.

Also disclosed are methods for treating a muscle wasting disease or disorder in a subject, comprising administering to the subject a therapeutically effective amount of a class I/II B HDAC inhibitor, or a pharmaceutically acceptable salt, hydrate, solvate, or polymorph thereof, and an androgen receptor modulator, or a pharmaceutically acceptable salt, hydrate, solvate, or polymorph thereof.

Also disclosed are uses of an HDAC inhibitor, or a pharmaceutically acceptable salt, hydrate, solvate, or polymorph thereof, and an androgen or SARM, or a pharmaceutically acceptable salt, hydrate, solvate, or polymorph thereof, in the manufacture of a medicament for the treatment of a muscle wasting disease or disorder in a mammal.

Also disclosed are methods for the manufacture of a medicament to treat a muscle wasting disease or disorder in a mammal comprising combining an HDAC inhibitor and an androgen or SARM with a pharmaceutically acceptable carrier or diluent.

Also disclosed are methods for treating cancer cachexia in a subject, comprising administering to the subject a therapeutically effective amount of a class I/IIB HDAC inhibitor, or a pharmaceutically acceptable salt, hydrate, solvate, or polymorph thereof, and an androgen receptor modulator, or a pharmaceutically acceptable salt, hydrate, solvate, or polymorph thereof.

Also disclosed are uses of an HDAC inhibitor, or a pharmaceutically acceptable salt, hydrate, solvate, or polymorph thereof, and an androgen or SARM, or a pharmaceutically acceptable salt, hydrate, solvate, or polymorph thereof, in the manufacture of a medicament for the treatment of cancer cachexia in a mammal.

Also disclosed are methods for the manufacture of a medicament to treat cancer cachexia in a mammal comprising combining an HDAC inhibitor and an androgen or SARM with a pharmaceutically acceptable carrier or diluent.

The details of one or more aspects of the disclosure are set forth in the accompanying drawings and the description below. Other features, objects, and advantages of the disclosure will be apparent from the description and drawings, and from the claims.

BRIEF DESCRIPTION OF THE FIGURES

The accompanying figures, which are incorporated in and constitute a part of this specification, illustrate several aspects and together with the description serve to explain the principles of the disclosure.

FIG. 2A is a plot showing terminal (Day 18 post-injection) bodyweights compared to baseline (Day 0), corrected for tumor mass. FIG. 2B is a plot showing terminal hindlimb skeletal muscle masses. FIG. 2D is a plot showing terminal (Day 17) body weights compared to baseline (Day 0), corrected for tumor mass. FIG. 2E is a plot showing terminal hindlimb skeletal muscle masses. FIG. 2F is a bar graph showing grip strength measurements performed on the final day of treatment compared to pre-treatment baseline. Statistics for all panels: Mean±SD. *p<0.05, p<0.01, *p<0.001, ****p<0.0001 versus tumor-bearing vehicle-treated controls, Dunnett's multiple comparison test; ns, no significant difference. An additional Tukey's multiple comparison test was used in panel 2D to demonstrate AR-42 combined with DHT resulted in significant improvement (p<0.0001) in terminal body weight compared to AR-42 treatment alone.

FIG. 3A contains bar graphs showing genes associated with muscle atrophy. FIG. 3B is a bar graph showing androgen receptor (AR) mRNA expression.

FIG. 4A is a table showing multiplex analysis of diverse serum cytokines in terminal samples from Study 2. Presented cytokines are limited to those showing significant differences from tumor-bearing vehicle-treated controls. G-CSF: granulocyte colony-stimulating factor, GM-CSF: granulocyte macrophage colony-stimulating factor, IL-6: interleukin-6, IL-17: interleukin-17, IP-10: interferon gamma-induced protein 10, KC: chemokine (C—X—C motif) ligand 1, LIF: leukemia inhibitory factor, M-CSF: macrophage colony-stimulating factor. Complete cytokine data are presented in Table 1.

FIG. 7 is a table showing non-compartmental analysis of single dose AR-42 pharmacokinetics in mouse.

FIG. 8A is a bar graph showing terminal body weights. FIG. 8B is a bar graph showing terminal gastrocnemius weights. FIG. 8C is a bar graph showing terminal quadriceps weights. FIG. 8D is a bar graph showing forelimb grip strength expressed as % baseline defined as (end of study grip strength)×100/(pre-treatment grip strength). ****p<0.0001, one-way ANOVA followed by Tukey's multiple comparisons procedure. Data are presented as means±SD.

FIG. 9A is a bar graph showing serum luteinizing hormone levels measured on Day 18. FIG. 9B is a graph showing per animal food consumption measured every two days. FIG. 9C is a plot showing spleen weights normalized to tumor mass-corrected terminal body weight. ****p<0.001, versus tumor-bearing vehicle-treated controls, Dunnett's multiple comparison test.

FIG. 10A is a plot showing terminal tumor volume comparisons between the initial (Study 1, Day 18) and confirmatory (Study 2, Day 17) combination studies. **p<0.0001, Study 1 versus Study 2; ns, no significant differences among treatment groups within each study; Sidak's multiple comparison test. FIG. 10B is a plot showing terminal (Day 17) body weights compared to baseline (Day 0), corrected for tumor mass. FIG. 10C is a plot showing terminal hindlimb skeletal muscle masses. FIG. 10D** is a plot showing terminal epididymal fat pad and heart mass. Data are presented as means±SD. Statistics for panels B-D: *p<0.05, p<0.01, *p<0.001, ****p<0.0001 versus tumor-bearing vehicle-treated controls, Dunnett's multiple comparison test; ns, no significant difference.

FIG. 11A is a plot showing tumor volume comparisons between Day 8 and Day 16. p<0.01 versus tumor-bearing controls, Sidak's multiple comparison test; ns, no significant differences. FIG. 11B is a plot showing terminal epididymal fat pad mass. **p<0.0001, versus tumor-bearing vehicle-treated controls, Dunnett's multiple comparison test. Data are presented as means±SD.

Figure 1B:
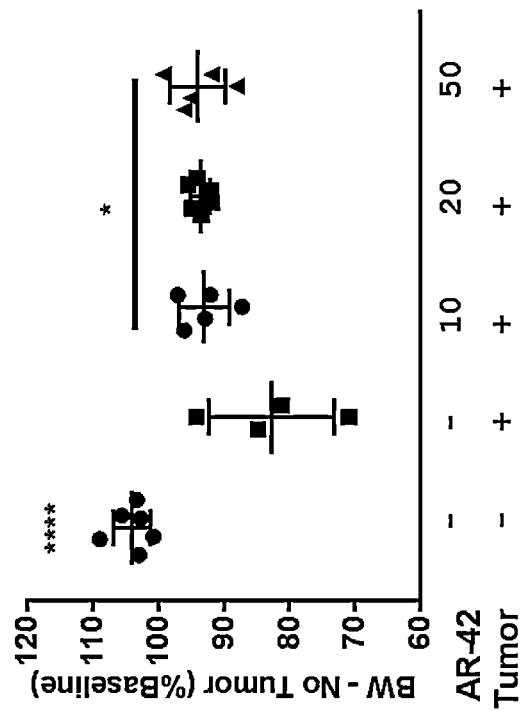
FIG. 1B is a graph showing AR-42 dose-response. Starting six days after C-26 cell injection, animals received vehicle or AR-42 orally at 10 or 20 mg/kg daily or 50 mg/kg every other day for 13 days (n=4-6). Day 18 bodyweights compared to Day 0, corrected for tumor mass according to the Materials and Methods. Bars represent mean±SD. *p<0.05, ****p<0.0001 versus tumor-bearing vehicle-treated controls, Tukey's multiple comparison test.

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

The present disclosure can be understood more readily by reference to the following detailed description of the disclosure and the Examples included therein.

Many modifications and other aspects disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific aspects disclosed and that modifications and other aspects are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual aspects described and illustrated herein has discrete components and features which may be readily separated from or combined with the features of any of the other several aspects without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present disclosure is not entitled to antedate such publication by virtue of prior disclosure. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Aspects of the present disclosure will employ, unless otherwise indicated, techniques of molecular biology, microbiology, organic chemistry, biochemistry, physiology, cell biology, blood vessel biology, and the like, which are within the skill of the art. Such techniques are explained fully in the literature.

Prior to describing the various aspects of the present disclosure, the following definitions are provided and should be used unless otherwise indicated. Additional terms may be defined elsewhere in the present disclosure.

A. Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

As used herein, the terms "optional" or "optionally" means that the subsequently described event or circumstance can or cannot occur, and that the description includes instances where said event or circumstance occurs and instances where it does not.

The term "Histone deacetylase (HDAC)" as used herein refers to and comprises a group of enzymes that remove acetyl groups (0=C—CH3) from a c-N-acetyl lysine amino acid on a histone, allowing the histones to wrap the DNA more tightly (EC Number 3.5.1.98). This is important because DNA is wrapped around histones, and DNA expression is regulated by acetylation and de-acetylation. HDACs are classified in four classes I to IV based on function and DNA sequence similarity. Class I includes isoforms HDAC1, HDAC2, HDAC3, and HDAC8; class II includes HDAC4, HDAC5, HDAC6, HDAC7, HDAC9 and HDAC10; Class IV includes HDAC11.

As used herein, the term "androgen" comprises the sex steroids; testosterone, dihydrotestosterone, DHEA, and diepiandrostenone.

Further as used herein "activity" comprises the signaling of a ligand/receptor system and includes the bio-availability of ligand, the ability of ligand to interact with receptor, the number and function of the receptors, and the ability of receptor signals to mediate biological effects. As used herein, "androgen activity" comprises the signaling of the androgen/androgen receptor system and includes bio-availability of androgens, the ability of androgens to interact with androgen receptors, the number and signaling of androgen receptors and the ability of androgen receptor signals to mediate biological effects.

As used herein, "administering" can refer to an administration that is oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intra-articular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The terms "co-administer(s)", "co-administering", and "co-administration" all refer to with respect to compounds or compositions, is meant either simultaneous administration or any manner of separate sequential administration of one or more Class I/IIB HDAC inhibitors with one or more androgens or SARMs. Preferably, if the administration is not simultaneous, the compounds are administered in a close time proximity to each other. Furthermore, it does not matter if the compounds are administered in the same dosage form, e.g. one compound may be administered topically and another compound may be administered orally. "Substantially simultaneously" means that the compound, i.e. a Class I/IIB HDAC inhibitor compound, is typically administered during or within a reasonably short time either before or after the administration of the androgen or SARM. Additionally, "co-administration", "co-administer(s)", and "co-administering" include administering more than one dose of the pharmaceutically active agent within 24 hours after a dose of a Class I/IIB HDAC inhibitor compound. In other words, Class I/IIB HDAC inhibitors need not be administered again before or with every administration of the androgen or SARM, but may be administered intermittently during the course of treatment. "Co-administration", "co-administer(s)", and "co-administering" also includes administering a Class I/IIB HDAC inhibitor and an androgen or SARM as a part of one or more pharmaceutical compositions, and such one or more pharmaceutical compositions may contain a co-formulation of a Class I/IIB HDAC inhibitor compound and an androgen or SARM, or individual formulations of a Class I/IIB HDAC inhibitor compound and an androgen or SARM compound.

It is understood that co-administration a Class I/IIB HDAC inhibitor compound and an androgen or SARM can be independently co-administered by any appropriate route of administration. The active agents, i.e. a Class I/IIB HDAC inhibitor compound and an androgen or SARM, can be administered by the same or different routes of administration, as appropriate. For example, one of the active ingredients can be administered orally and the other administered orally or by some other appropriate route of administration. Alternatively, the combination of active ingredients can be concurrently orally administered. In a further example, consistent with this understanding, one of the active ingredients can be administered parenterally, for example, intravenously, intramuscularly, subcutaneously, topically, intravaginally, rectally, intranasally, inhalationally, intrathecally, intraocularly, and one or more of the other active ingredients administrated by a similar or distinct route of administration. Moreover, it is understood, that a Class I/IIB HDAC inhibitor compound and an androgen or SARM can be co-administered or independently administered by distinct routes of administration such as parenterally, orally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, or intrathecally.

As used herein, "combination therapy" (or "co-therapy") refers to the administration of a Class I/IIB HDAC inhibitor compound and an androgen or SARM during the course of therapy or treatment for a cancer cachexia. Such combination therapy may involve the administration of the Class I/IIB HDAC inhibitor compound before, during, and/or after the administration of the androgen or SARM administered to ameliorate, treat, reverse, or cure the cancer cachexia or symptoms associated with the cancer cachexia. The administration of the Class I/IIB HDAC inhibitor compound may be separated in time from the administration of androgen or SARM by up to several weeks, and may precede it or follow it, but more commonly the administration of the Class I/IIB HDAC inhibitor compound will accompany at least one aspect of the administration of the androgen or SARM.

As used herein, "concurrently" means (1) simultaneously in time, or (2) at different times during the course of a common treatment schedule.

As used herein, "therapeutic agent" can refer to any substance, compound, molecule, and the like, which can be biologically active or otherwise can induce a pharmacologic, immunogenic, biologic and/or physiologic effect on a subject to which it is administered to by local and/or systemic action. A therapeutic agent can be a primary active agent, or in other words, the component(s) of a composition to which the whole or part of the effect of the composition is attributed. A therapeutic agent can be a secondary therapeutic agent, or in other words, the component(s) of a composition to which an additional part and/or other effect of the composition is attributed. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, "attached" can refer to covalent or non-covalent interaction between two or more molecules. Non-covalent interactions can include ionic bonds, electrostatic interactions, van der Walls forces, dipole-dipole interactions, dipole-induced-dipole interactions, London dispersion forces, hydrogen bonding, halogen bonding, electromagnetic interactions, $\pi$-$\pi$ interactions, cation-$\pi$ interactions, anion-$\pi$ polar $\pi$-interactions, and hydrophobic effects.

As used interchangeably herein, "subject," "individual," or "patient" can refer to a vertebrate organism, such as a mammal (e.g. human). "Subject" can also refer to a cell, a population of cells, a tissue, an organ, or an organism, preferably to human and constituents thereof.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as cancer cachexia. The effect can be therapeutic in terms of a partial or complete cure of a disease, condition, symptom or adverse effect attributed to the disease, disorder, or condition.

The term "treatment" as used herein can include any treatment of cancer cachexia in a subject, particularly a human and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, e.g., such as treating the pain of a subject by administration of an analgesic agent even though such agent does not treat the cause of the pain.

As used herein, "dose," "unit dose," or "dosage" can refer to physically discrete units suitable for use in a subject, each unit containing a predetermined quantity of a disclosed compound and/or a pharmaceutical composition thereof calculated to produce the desired response or responses in association with its administration.

As used herein, "therapeutic" can refer to treating, healing, and/or ameliorating a disease, disorder, condition, or side effect, or to decreasing in the rate of advancement of a disease, disorder, condition, or side effect.

As used herein, "effective amount" can refer to the amount of a disclosed compound or pharmaceutical composition provided herein that is sufficient to effect beneficial or desired biological, emotional, medical, or clinical response of a cell, tissue, system, animal, or human. An effective amount can be administered in one or more administrations, applications, or dosages. The term can also include within its scope amounts effective to enhance or restore to substantially normal physiological function.

As used herein, the term "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors within the knowledge and expertise of the health practitioner and which may be well known in the medical arts. In the case of treating a particular disease or condition, in some instances, the desired response can be inhibiting the progression of the disease or condition. This may involve only slowing the progression of the disease temporarily. However, in other instances, it may be desirable to halt the progression of the disease permanently. This can be monitored by routine diagnostic methods known to one of ordinary skill in the art for any particular disease. The desired response to treatment of the disease or condition also can be delaying the onset or even preventing the onset of the disease or condition.

For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. It is generally preferred that a maximum dose of the pharmacological agents of the disclosure (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

A response to a therapeutically effective dose of a disclosed compound and/or pharmaceutical composition, for example, can be measured by determining the physiological effects of the treatment or medication, such as the decrease or lack of disease symptoms following administration of the treatment or pharmacological agent. Other assays will be known to one of ordinary skill in the art and can be employed for measuring the level of the response. The amount of a treatment may be varied for example by increasing or decreasing the amount of a disclosed compound and/or pharmaceutical composition, by changing the disclosed compound and/or pharmaceutical composition administered, by changing the route of administration, by changing the dosage timing and so on. Dosage can vary, and can be administered in one or more dose administrations daily, for one or several days. Guidance can be found in the literature for appropriate dosages for given classes of pharmaceutical products.

As used herein, the term "prophylactically effective amount" refers to an amount effective for preventing onset or initiation of a disease or condition.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

The term "pharmaceutically acceptable" describes a material that is not biologically or otherwise undesirable, i.e., without causing an unacceptable level of undesirable biological effects or interacting in a deleterious manner.

The term "pharmaceutically acceptable salts", as used herein, means salts of the active principal agents which are prepared with acids or bases that are tolerated by a biological system or tolerated by a subject or tolerated by a biological system and tolerated by a subject when administered in a therapeutically effective amount. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include, but are not limited to; sodium, potassium, calcium, ammonium, organic amino, magnesium salt, lithium salt, strontium salt or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include, but are not limited to; those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like.

The term "pharmaceutically acceptable ester" refers to esters of compounds of the present disclosure which hydrolyze in vivo and include those that break down readily in the human body to leave the parent compound or a salt thereof. Examples of pharmaceutically acceptable, non-toxic esters of the present disclosure include C 1-to-C 6 alkyl esters and C 5-to-C 7 cycloalkyl esters, although C 1-to-C 4 alkyl esters are preferred. Esters of disclosed compounds can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, for example with methyl iodide, benzyl iodide, cyclopentyl iodide or alkyl triflate. They also can be prepared by reaction of the compound with an acid such as hydrochloric acid and an alcohol such as ethanol or methanol.

The term "pharmaceutically acceptable amide" refers to non-toxic amides of the present disclosure derived from ammonia, primary C 1-to-C 6 alkyl amines and secondary C 1-to-C 6 dialkyl amines. In the case of secondary amines, the amine can also be in the form of a 5- or 6-membered heterocycle containing one nitrogen atom. Amides derived from ammonia, C 1-to-C 3 alkyl primary amides and C 1-to-C 2 dialkyl secondary amides are preferred. Amides of disclosed compounds can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable amides are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, and piperidine. They also can be prepared by reaction of the compound with an acid such as sulfuric acid and an alkylcarboxylic acid such as acetic acid, or with acid and an arylcarboxylic acid such as benzoic acid under dehydrating conditions such as with molecular sieves added. The composition can contain a compound of the present disclosure in the form of a pharmaceutically acceptable prodrug.

The term "pharmaceutically acceptable prodrug" or "prodrug" represents those prodrugs of the compounds of the present disclosure which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the present disclosure can be rapidly transformed in vivo to a parent compound having a structure of a disclosed compound, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

The term "contacting" as used herein refers to bringing a disclosed compound or pharmaceutical composition in proximity to a cell, a target protein, or other biological entity together in such a manner that the disclosed compound or pharmaceutical composition can affect the activity of the a cell, target protein, or other biological entity, either directly; i.e., by interacting with the cell, target protein, or other biological entity itself, or indirectly; i.e., by interacting with another molecule, co-factor, factor, or protein on which the activity of the cell, target protein, or other biological entity itself is dependent.

It is understood, that unless otherwise specified, temperatures referred to herein are based on atmospheric pressure (i.e. one atmosphere).

B. Therapeutic Agents for Treatment of Muscle Wasting and Cachexias

Described herein are compounds, such as an HDAC inhibitor and an androgen or SARM, that have therapeutic or clinical utility when combined or co-administered. Also described herein are methods of administering the combination of therapeutic agents to a subject in need thereof. In some aspects, the subject can have a muscle wasting disease, including, but not limited to, cancer cachexia. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

In various aspects, surprisingly, it has been determined that androgen or SARM administration when combined with an HDAC inhibitor, e.g., AR-42, is effective in the C-26 model of cancer cachexia. Without wishing to be bound by a particular theory, it is hypothesized that the mechanisms underlying an established anabolic therapy and a novel anti-catabolic therapy may be sufficiently distinct to allow for improved overall efficacy, when combined, in muscle wasting dieases, including, but not limited to, cancer cachexia.

In various aspects, it is contemplated herein that the disclosed compounds or therapeutic agents further comprise their biosteric equivalents. The term "bioisosteric equivalent" refers to compounds or groups that possess near equal molecular shapes and volumes, approximately the same distribution of electrons, and which exhibit similar physical and biological properties. Examples of such equivalents are: (i) fluorine vs. hydrogen, (ii) oxo vs. thia, (iii) hydroxyl vs. amide, (iv) carbonyl vs. oxime, (v) carboxylate vs. tetrazole. Examples of such bioisosteric replacements can be found in the literature and examples of such are: (i) Burger A, *Relation of chemical structure and biological activity*; in Medicinal Chemistry Third ed., Burger A, ed.; Wiley-Interscience; New York, 1970, 64-80; (ii) Burger, A.; "Isosterism and bioisosterism in drug design"; Prog. Drug Res. 1991, 37, 287-371; (iii) Burger A, "Isosterism and bioanalogy in drug design", *Med. Chem. Res.* 1994, 4, 89-92; (iv) Clark R D, Ferguson A M, Cramer R D, "Bioisosterism and molecular diversity", *Perspect. Drug Discovery Des.* 1998, 9/10/11, 213-224; (v) Koyanagi T, Haga T, "Bioisosterism in agrochemicals", *ACS Symp. Ser.* 1995, 584, 15-24; (vi) Kubinyi H, "Molecular similarities. Part 1. Chemical structure and biological activity", *Pharm. Unserer Zeit* 1998, 27, 92-106; (vii) Lipinski C A.; "Bioisosterism in drug design"; *Annu. Rep. Med. Chem.* 1986, 21, 283-91; (viii) Patani G A, LaVoie E J, "Bioisosterism: A rational approach in drug design", *Chem. Rev.* (Washington, D.C.) 1996, 96, 3147-3176; (ix) Soskic V, Joksimovic J, "Bioisosteric approach in the design of new dopaminergic/serotonergic ligands", *Curr. Med. Chem.* 1998, 5, 493-512 (x) Thornber C W, "Isosterism and molecular modification in drug design", *Chem. Soc. Rev.* 1979, 8, 563-80.

In further aspects, bioisosteres are atoms, ions, or molecules in which the peripheral layers of electrons can be considered substantially identical. The term bioisostere is usually used to mean a portion of an overall molecule, as opposed to the entire molecule itself. Bioisosteric replacement involves using one bioisostere to replace another with the expectation of maintaining or slightly modifying the biological activity of the first bioisostere. The bioisosteres in this case are thus atoms or groups of atoms having similar size, shape and electron density. Preferred bioisosteres of esters, amides or carboxylic acids are compounds containing two sites for hydrogen bond acceptance. In one aspect, the ester, amide or carboxylic acid bioisostere is a monocyclic heteroaryl ring, such as an optionally substituted 1H-imidazolyl, an optionally substituted oxazolyl, 1H-tetrazolyl, [1,2,4]triazolyl, or an optionally substituted [1,2,4]oxadiazolyl.

In various aspects, it is contemplated herein that the disclosed compounds further comprise their isotopically-labelled or isotopically-substituted variants, i.e., compounds identical to those described, but for the fact that one or more atoms are replaced by an atom having an atomic mass or mass number different from the atomic mass or mass number typically found in nature. Examples of isotopes that can be incorporated into compounds of the disclosure include isotopes of hydrogen, carbon, nitrogen, oxygen, phosphorous, fluorine and chlorine, such as $^{2}$H, $^{3}$H, $^{13}$C, $^{14}$C, $^{15}$N, $^{18}$O, $^{17}$O, $^{35}$S, $^{18}$F and $^{36}$Cl, respectively. Compounds further comprise prodrugs thereof, and pharmaceutically acceptable salts of said compounds or of said prodrugs which contain the aforementioned isotopes and/or other isotopes of other atoms are within the scope of this disclosure. Certain isotopically-labelled compounds of the present disclosure, for example those into which radioactive isotopes such as $^{3}$H and $^{14}$O are incorporated, are useful in drug and/or substrate tissue distribution assays. Tritiated, i.e., $^{3}$H, and carbon-14, i.e., $^{14}$C, isotopes are particularly preferred for their ease of preparation and detectability. Further, substitution with heavier isotopes such as deuterium, i.e., $^{2}$H, can afford certain therapeutic advantages resulting from greater metabolic stability, for example increased in vivo half-life or reduced dosage requirements and, hence, may be preferred in some circumstances. Isotopically labelled compounds of the present disclosure and prodrugs thereof can generally be prepared by carrying out the procedures below, by substituting a readily available isotopically labelled reagent for a non-isotopically labelled reagent.

In various aspects, the disclosed compounds can possess at least one center of asymmetry, they can be present in the form of their racemates, in the form of the pure enantiomers and/or diastereomers or in the form of mixtures of these enantiomers and/or diastereomers. The stereoisomers can be present in the mixtures in any arbitrary proportions. In some aspects, provided this is possible, the disclosed compounds can be present in the form of the tautomers.

Thus, methods which are known per se can be used, for example, to separate the disclosed compounds which possess one or more chiral centers and occur as racemates into their optical isomers, that is enantiomers or diastereomers. The separation can be effected by means of column separation on chiral phases or by means of recrystallization from an optically active solvent or using an optically active acid or base or by means of derivatizing with an optically active reagent, such as an optically active alcohol, and subsequently cleaving off the residue.

In various aspects, the disclosed compounds can be in the form of a co-crystal. The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Preferred co-crystals include p-toluenesulfonic acid and benzenesulfonic acid.

The term "pharmaceutically acceptable co-crystal" means one that is compatible with the other ingredients of the formulation and not deleterious to the recipient thereof.

In a further aspect, the disclosed compounds can be isolated as solvates and, in particular, as hydrates of a disclosed compound, which can be obtained, for example, by crystallization from a solvent or from aqueous solution. In this connection, one, two, three or any arbitrary number of solvate or water molecules can combine with the compounds according to the disclosure to form solvates and hydrates.

The disclosed compounds can be used in the form of salts derived from inorganic or organic acids. Pharmaceutically acceptable salts include salts of acidic or basic groups present in the disclosed compounds. Suitable pharmaceutically acceptable salts include base addition salts, including alkali metal salts, e.g., sodium or potassium salts; alkaline earth metal salts, e.g., calcium or magnesium salts; and salts formed with suitable organic ligands, e.g., quaternary ammonium salts, which may be similarly prepared by reacting the drug compound with a suitable pharmaceutically acceptable base. The salts can be prepared in situ during the final isolation and purification of the compounds of the present disclosure; or following final isolation by reacting a free base function, such as a secondary or tertiary amine, of a disclosed compound with a suitable inorganic or organic acid; or reacting a free acid function, such as a carboxylic acid, of a disclosed compound with a suitable inorganic or organic base.

Acidic addition salts can be prepared in situ during the final isolation and purification of a disclosed compound, or separately by reacting moieties comprising one or more nitrogen groups with a suitable acid. In various aspects, acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. In a further aspect, salts further include, but are not limited, to the following: hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate, butyrate, camphorate, camphorsulfonate, digluconate, glycerophosphate, hemisulfate, heptanoate, hexanoate, fumarate, hydrochloride, 2-hydroxyethanesulfonate (isethionate), nicotinate, 2-naphthalenesulfonate, oxalate, pectinate, persulfate, 3-phenylpropionate, picrate, pivalate, propionate, succinate, tartrate, thiocyanate, phosphate, glutamate, bicarbonate, undecanoate, and pamoate (i.e., 1,1'-methylene-bis-(2-hydroxy-3-naphthoate)) salts. Also, basic nitrogen-containing groups can be quatemized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others.

Basic addition salts can be prepared in situ during the final isolation and purification of a disclosed compound, or separately by reacting carboxylic acid moieties with a suitable base such as the hydroxide, carbonate or bicarbonate of a pharmaceutical acceptable metal cation or with ammonia, or an organic primary, secondary or tertiary amine. Pharmaceutical acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like. In further aspects, bases which may be used in the preparation of pharmaceutically acceptable salts include the following: ammonia, L-arginine, benethamine, benzathine, calcium hydroxide, choline, deanol, diethanolamine, diethylamine, 2-(diethylamino)-ethanol, ethanolamine, ethylenediamine, N-methylglucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

C. Class I/IIB HDAC Inhibitors

In various aspects, the disclosed Class I/IIB HDAC inhibitor comprises the disclosed compound and/or its analog, derivative, isomer, metabolite, pharmaceutically acceptable salt, hydrate, N-oxide, prodrug, polymorph, crystal, or any combination thereof, in an amount effective to treat cancer cachexia in combination or co-administered with an androgen or SARM in the subject. Histone deacetylase (HDAC) proteins are a family of enzymes that control the acetylation state of protein lysine residues, notably lysine residues contained in the N-terminal extensions of core histones. The acetylation state of histones affect gene expression by influencing chromatin conformation. In addition, the stability or biological function of several nonhistone proteins is regulated by the acetylation state of specific lysine residues (Gallinari et al., 2007, Cell Res. 17:191-211; Kazantsev and Thompson, 2008, Nat Rev Drug Discov. 7:854-868). Histone deacetylases may include class I and class II enzymes, and may also be of human origin, including, but not limited to, HDAC-1, HDAC-2, HDAC-3, HDAC-4, HDAC-5, HDAC-6, HDAC-7, and HDAC-8.

In humans, HDAC proteins comprise a family of 18 members, which are separated into four classes based on size, cellular localization, number of catalytic active sites, and homology to yeast HDAC proteins. Class I includes HDAC1, HDAC2, HDAC3, and HDAC8. Class II consists of six HDAC proteins that are further divided into two subclasses. Class IIa includes HDAC4, HDAC5, HDAC7, and HDAC9, which each contain a single catalytic active site. Class IIb includes HDAC6 and HDAC10, which each contain two active sites, although only HDAC6 has two catalytically competent active sites. HDAC11 is the sole member of class IV, based on phylogenetic analysis. Class I, II, and IV HDAC proteins operate by a metal ion-dependent mechanism, as indicated by crystallographic analysis. In contrast, class III HDAC proteins, referred to as sirtuins (i.e., SIRT1 through SIRT7), operate by a NAD+-dependent mechanism unrelated to the other HDAC proteins (Gregoretti et al., 2004, J Mol Biol. 338:17-31; Grozinger and Schreiber, 2002, Chem Biol. 9:3-16).

As used herein, the terms "histone deacetylase inhibitor" and "HDAC inhibitor" are intended to refer to a compound which is capable of interacting with a histone deacetylase and inhibiting its enzymatic activity. The phrase "inhibiting histone deacetylase enzymatic activity" means reducing the ability of a histone deacetylase to remove an acetyl group from a histone. In some aspects, such reduction of histone deacetylase activity is at least about 50%, at least about 75%, or at least about 90%. In other aspects, histone deacetylase activity is reduced by at least about 95% or at least about 99%. In the methods of this disclosure, a single HDAC inhibitor and/or any combination of HDAC inhibitors may be employed.

As used herein, the terms "Class I histone deacetylase inhibitor" and "Class I HDAC inhibitor" are intended to refer to a compound which is capable of interacting with a Class I histone deacetylase and inhibiting its enzymatic activity. The phrase "inhibiting Class I histone deacetylase enzymatic activity" means reducing the ability of a Class I histone deacetylase to remove an acetyl group from a histone. In some aspects, such reduction of a Class I histone deacetylase activity is at least about 50%, at least about 75%, or at least about 90%. In other aspects, Class I histone deacetylase activity is reduced by at least about 95% or at least about 99%. In the methods of this disclosure, a single Class I HDAC inhibitor and/or any combination of Class I HDAC inhibitors may be employed.

As used herein, the terms "Class IIb histone deacetylase inhibitor" and "Class IIb HDAC inhibitor" are intended to refer to a compound which is capable of interacting with a Class IIb histone deacetylase and inhibiting its enzymatic activity. The phrase "inhibiting Class IIb histone deacetylase enzymatic activity" means reducing the ability of a Class IIb histone deacetylase to remove an acetyl group from a histone. In some aspects, such reduction of a Class IIb histone deacetylase activity is at least about 50%, at least about 75%, or at least about 90%. In other aspects, Class IIb histone deacetylase activity is reduced by at least about 95% or at least about 99%. In the methods of this disclosure, a single Class IIb HDAC inhibitor and/or any combination of Class IIb HDAC inhibitors may be employed.

As used herein, the terms "Class I/IIb histone deacetylase inhibitor" and "Class I/IIb HDAC inhibitor" are intended to refer to a compound which is capable of interacting with a Class I and/or Class IIb histone deacetylase and inhibiting its enzymatic activity. The phrase "inhibiting Class I and/or Class IIb histone deacetylase enzymatic activity" means reducing the ability of a Class I and/or Class IIb histone deacetylase to remove an acetyl group from a histone. In some aspects, such reduction of a Class I and/or Class IIb histone deacetylase activity is at least about 50%, at least about 75%, or at least about 90%. In other aspects, Class I and/or Class IIb histone deacetylase activity is reduced by at least about 95% or at least about 99%. In the methods of this disclosure, a single Class I and/or Class IIb HDAC inhibitor and/or any combination of Class I and/or Class IIb HDAC inhibitors may be employed.

In various aspects, it is understood that a Class 1/IIB HDAC inhibitor can selectively inhibit a Class I HDAC enzyme, a Class IIB HDAC enzyme, or both Class I and Class IIB enzymes. However, it is understood that a Class 1/IIB HDAC inhibitor, can, in some aspects, be a pan-HDAC inhibitor, or inhibit a HDAC-3, HDAC-4, HDAC-5, HDAC-6, HDAC-7, and HDAC-8, in addition to inhibiting a Class I HDAC enzyme, a Class IIB HDAC enzyme, or both Class I and Class IIB enzymes.

In a further aspect, the disclosed Class 1/IIB HDAC inhibitor comprises those HDAC inhibitors described in U.S. Pat. No. 8,318,808, and these compounds can be used in the disclosed methods of treatment and pharmaceutical compositions. These HDAC inhibitors are based on, for example, fatty acids coupled with $Zn^{2+}$-chelating motifs through aromatic Ω-amino acid linkers. In various aspects, the HDAC inhibitors may have the formula:

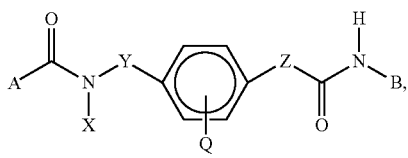

wherein X is chosen from H and CH3; Y is (CH2)n wherein n is 0-2; Z is chosen from (CH2)m wherein m is 0-3 and (CH)2; A is a hydrocarbyl group; B is o-aminophenyl or hydroxyl group; and Q is a halogen, hydrogen, or methyl.

In another aspect, methods described herein utilize AR-42, also known as (S)—N-hydroxy-4-(3-methyl-2-phenylbutanamido)benzamide having the following chemical structure:

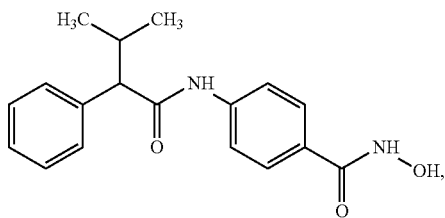

In yet another aspect, AR-42 includes salts, solvates, hydrates, anhydrous, co-crystalline and other crystalline forms and combinations. AR-42 can be formulated into a variety of dosage forms having increased stability, increased bioavailability, sustained release, and other properties. In a further aspect, AR-42 includes one or more of the polymorph forms as disclosed in U.S. Patent Publ. No. 2014/0271604, which is incorporated herein by reference in its entirety.

In one aspect, HDAC inhibitors are classified characterized as being zinc dependent or nicotinamide adenine dinucleotide (NAD) dependent (Discov Med November 2010) and are placed into four classes with eighteen family subtypes based on its HDAC substrate: class I (HDACs 1, 2, 3, and 8); class II (HDACs 4, 5, 6, 7, 9, and 10; class III (sirtuins 1-7 (SIRT)); and class IV (HDAC 11). Id. In another aspect, HDAC inhibitors include, but are not limited to, Vorinostat (SAHA) (class I and II inhibitor), Depsipeptide class I inhibitor, and AR-42 (class I and IIb inhibitor). See, e.g., Strahl, B. D. and Allis, C. D. (2000) Nature 403:41-45. Other HDAC inhibitors (e.g., Trichostatin A or TSA) inhibit class 1 and class 2 HDACs. The substrates for HDAC inhibitors vary among the classes and subtypes.

In another aspect, the disclosed Class I/IIB HDAC inhibitor inhibits class 1 and class 2b HDACs. In yet another aspect, the HDAC inhibitor is AR-42.

In another aspect, the disclosed Class I/IIB HDAC inhibitor is selected from ACY1215 (Acetylon), CG200745 (Crystal Genomics), 4SC-202 (4SC corporation), CHR-2845 (Chroma Therapeutics), AR-42 (Arno Therapeutics), CUDC-101 (Curis Inc), Givinostat (Italfarmaco), Resminostat (4SC-Corporation), Pracinostat (S*B10 Pte Ltd), Etinostat (Syndax), Abexinostat (Pharmacyclics), Mocetinostat (Methylgene), Belinostat (TopoTarget), Valproic Acid (Instituto Nacional de Cancerologia), Panobinostat (Novartis), Vorinostat (Merck), and Romidepsin (Celgene), or combinations thereof.

In a further aspect, the disclosed Class I/IIB HDAC inhibitor is an HDAC inhibitor disclosed in U.S. Pat. Publ. No. 2017/0044185, which is incorporated herein by reference in its entirety.

In some aspects, the disclosed Class I/IIB HDAC inhibitor is selected from 8-(hydroxyamino)-8-oxo-N-phenyl-octanamide (2-01); (1 S,4 S,7Z,10 S,16E,21R)-7-ethylidene-4,21-diisopropyl-2-oxa-12,13-dithia-(E)-3-[4-[[2-(2-methyl-1H-indol-3-yl)ethylamino]methyl]phenyl]prop-2-enehydroxamic acid (2-03); (E)-3-[3-(phenylsulfamoyl)phenyl]prop-2-enehydroxamic acid (2-07); 2-propylpentanoic acid (2-17); 5,8,20,23-tetrazabicyclo[8.7.6]tricos-16-ene-3,6,9,19,22-pentone (2-02); 3-pyridylmethyl N-[[4-[(2-aminophenyl)carbamoyl]phenyl]methyl] carbamate (2-04); N-(2-aminophenyl)-4-[[[4-(3-pyridyl)pyrimidin-2-yl]amino]methyl]benzamide (2-05); N-[7-(hydroxyamino)-7-oxo-heptyl]-2-(N-phenylanilino) pyrimidine-5-carboxamide (2-06); (E)-3-[1-[4-[(dimethylamino)methyl]phenyl]sulfonylpyrrol-3-yl]prop-2-enehydroxamic acid (2-08); [6-(diethylaminomethyl)-2-naphthyl]methyl N-[4-(hydroxycarbamoyl)phenyl]-carbamate (2-09); (E)-3-[2-butyl-1-[2-(diethylamino)ethyl]benzimidazol-5-yl]prop-2-enehydroxamic acid (2-10); 3-[(dimethylamino)methyl]-N-[2-[4-(hydroxycarbamoyl)phenoxy]ethyl]benzofuran-2-carboxamide (2-11); (E)-N-(2-aminophenyl)-3-[1-[4-(1-methylpyrazol-4-yl)phenyl]sulfonylpyrrol-3-yl]prop-2-enamide (2-12); (2S)—N-[4-(hydroxycarbamoyl)phenyl]-3-methyl-2-phenyl-butanamide (2-13); (E)-N-[3-(dimethylamino)propyl]-8-(hydroxyamino)-2-(1-naphthyloxymethyl)-8-oxo-oct-2-enamide (2-14); 4-[(2-methyl-3,4-dihydro-1H-pyrido[4,3-b]indol-5-yl)methyl]benzenecarbohydroxamic acid (2-15) sodium; 4-phenylbutanoate (2-16); N-(2-amino-5-fluorophenyl)-4-[[[(E)-3-(3-pyridyl)prop-2-enoyl]amino]methyl]benzamide (2-18); 2-[4-[[(1-methylindol-3-yl)methylamino]methyl]-1-piperidyl]pyrimidine-5-carbohydroxamic acid (2-19); cyclopentyl (2S)-2-[[4-[[8-(hydroxyamino)-8-oxo-octanoyl]amino]phenyl]-methylamino]-2-phenyl-acetate (2-20); 2-[(1R,5S)-6-[(6-fluoro-2-quinolyl)methylamino]-3-bicyclo[3.1.0]hexanyl]pyrimidine-5-carbohydroxamic acid (2-21); N-[6-(2-aminoanilino)-6-oxo-hexyl]-4-methyl-benzamide (2-22); 4-acetamido-N-(2-aminophenyl)benzamide (2-23); ACY-241 (2-24); OCID-4681 (2-25) and FRM-0334 (2-26) or a pharmaceutically or veterinary acceptable salt thereof, or any stereoisomer thereof.

In various aspects, further suitable HDAC inhibitors include, but are not limited to, short-chain fatty acid, a hydroxamic acid, a cyclic tetrapeptide, a benzamide, a tricyclic lactam, a sultam derivative, an organosulfur compound; an electrophilic ketone, pimeloylanilide o-aminoanilide (PAOA), depudecin, a psammaplin, Vorinostat, tubacin, curcumin, histacin, 6-Chloro-2,3,4,9-tetrahydro-1H-carbazole-1-carboxamide, CRA-024781, CRA-026440, CG1521, PXD101, G2M-777, CAY10398, CTPB MGCD0103, CUDC-100, and/or any derivative thereof, as well as any combination thereof.

In some aspects, a short-chain fatty acid can be, but is not limited to, butyrate, phenylbutyrate, pivaloyloxymethyl butyrate, N-Hydroxy-4-(3-methyl-2-phenyl-butyrylamino)-benzamide,4-(2,2-Dimethyl-4-phenylbutyrylamino)-N-hydroxybenzamide, valproate, valproic acid, and/or any derivative thereof, as well as any combination thereof.

In some aspects, a hydroxamic acid can be, but is not limited to, suberoylanilide hydroxamic acid (SAHA), oxamflatin, M-carboxycinnamic acid bishydroxamide, suberic bishydroxamate (SBHA), nicotinamide, scriptaid (SB-556629), scriptide, splitomicin, lunacin, ITF2357, A-161906, NVP-LAQ824, LBH589, pyroxamide, Panobinostat (LB589), givinostat (or gavinostat (originally ITF2357)), resminostat (RAS2410), CBHA, 3-C1-UCHA, SB-623, SB-624, SB-639, SK-7041, a propenamide, an aroyl pyrrolyl hydroxyamide, a trichostatin, and/or any derivative thereof.

In some aspects, a propenamide can be, but is not limited to, MC 1293 and/or any derivative thereof, a aroyl pyrrolyl hydroxyamide can be, but is not limited to, APHA Compound 8 and/or any derivative thereof, as well as any combination thereof, and a trichostatin can be, but is not limited to, trichostatin A, trichostatin C, and/or any derivative thereof, as well as any combination thereof.

In some aspects, a cyclic tetrapeptide can be, but is not limited to, a trapoxin, romidepsin, HC-toxin, chlamydocin, diheteropeptin, WF-3161, Cyl-1, Cyl-2, apicidin, depsipeptide (FK228), FR225497, FR901375, a spiruchostatin, a salinamide, a cyclic-hydroxamic-acid-containing peptide, and/or any derivative thereof, as well as any combination thereof.

In some aspects, a spiruchostatin can be, but is not limited to, spiruchostatin A, spiruchostatin B, spiruchostatin C, and/or any derivative thereof; and a salinamide can be, but is not limited to, salinamide A, salinamide B and/or any derivative thereof, as well as any combination thereof.

In some aspects, a benzamide can be, but is not limited to, M344, MS-275, CI-994 (N-acetyldinaline), tacedinaline, sirtinol, and/or any derivative thereof, as well as any combination thereof.

In some aspects, an organosulfur compound can be, but is not limited to, diallyl disulfide, sulforaphane; and/or any derivative thereof, as well as any combination thereof.

In some aspects, an electrophilic ketone can be, but is not limited to, a-ketoamide, trifluoromethylketone and/or any derivative thereof, as well as any combination thereof.

In some aspects, the HDAC inhibitor can be, for example, SAHA, tributyrin, romidepsin, belinostat, pracinostat Valproic acid, valproate, Panobinostat, Trichostatin A, Mocetinostat (MGCD0103), Abexinostat (PC1-24781), Entinostat (MS-275), SB939, Resminostat (4SC-201) an oral pan-HDACi, Givinostat, Quisinostat, Kevetrin, CUDC-101, AR-42, CHR-2845, CHR-3996, 4SC-202, CG200745, ACY-1215, ME-344, and/or Sulforaphane, as well as any combination thereof.

D. Androgens or Non-Steroidal, Selective Androgen Receptor Modulators (SARM)

In various aspects, the disclosed androgen or SARM comprises the disclosed compound and/or its analog, derivative, isomer, metabolite, pharmaceutically acceptable salt, hydrate, N-oxide, prodrug, polymorph, crystal, or any combination thereof, in an amount effective to treat cancer cachexia in combination or co-administered with a Class I/II B HDAC inhibitor in the subject.

As contemplated herein, the SARMs which are useful in preventing and treating cancer cachexia are classified as androgen receptor agonists (AR agonists) or androgen receptor antagonists (AR antagonists). In various aspects, it is understood herein that selective androgen receptor modulators (SARMs) are a class of androgen receptor targeting agents (ARTA), which demonstrate androgenic and anabolic activity of a nonsteroidal ligand for the androgen receptor.

The AR is a ligand-activated transcriptional regulatory protein that mediates induction of male sexual development and function through its activity with endogenous androgens (male sex hormones). The androgenic hormones are steroids which are produced in the body by the testis and the cortex of the adrenal gland. Androgenic steroids play an important role in many physiologic processes, including the development and maintenance of male sexual characteristics such as muscle and bone mass, prostate growth, spermatogenesis, and the male hair pattern (Matsumoto, Endocrinol. Met. Clin. N. Am. 23:857-75 (1994)). The endogenous steroidal androgens include testosterone and dihydrotestosterone ("DHT"). Other steroidal androgens include esters of testosterone, such as the cypionate, propionate, phenylpropionate, cyclopentylpropionate, isocarporate, enanthate, and decanoate esters, and other synthetic androgens such as 7-Methyl-Nortestosterone ("MENT") and its acetate ester (Sundaram et al., "7 Alpha-Methyl-Nortestosterone (MENT): The Optimal Androgen For Male Contraception," Ann. Med., (1993) ("Sundaram")).

In various aspects, an intact androgen receptor (AR) signaling pathway is crucial for appropriate development of skeletal muscles. Furthermore, an intact AR-signalling pathway increases lean muscle mass, muscle strength and muscle protein synthesis. It is believed that appropriate activation of the AR signaling pathway can have positive effects such as increasing lean muscle mass, muscle strength and muscle protein synthesis. In particular, as disclosed herein, activation of the AR signaling pathway in the presence of a Class I/II B HDAC inhibitor can have particularly beneficial effects associated with increasing lean muscle mass, muscle strength and muscle protein synthesis, thereby preventing and treating cancer cachexia.

A receptor agonist is a substance which binds receptors and activates them. A receptor antagonist is a substance which binds receptors and inactivates them. In one aspect, the SARMs which are useful in treating and preventing cancer cachexia and which modulate leptin levels are AR agonists, and are, therefore, useful in binding to and activating the AR. In another aspect, the SARMs which are useful in treating and preventing cancer cachexia and which modulate leptin levels are AR antagonists, and are, therefore, useful in binding to and inactivating the AR. Assays to determine whether the compounds of the present disclosure are AR agonists or antagonists are well known to a person skilled in the art. For example, AR agonistic activity can be determined by monitoring the ability of the SARM compounds to maintain and/or stimulate the growth of AR containing tissue such as prostate and seminal vesicles, as measured by weight. AR antagonistic activity can be determined by monitoring the ability of the SARM compounds inhibit the growth of AR containing tissue.

In yet another aspect, the SARM compounds of the present disclosure can be classified as partial AR agonist/antagonists. The SARMs are AR agonists in some tissues, to cause increased transcription of AR-responsive genes (e.g. muscle anabolic effect). In other tissues, these compounds serve as competitive inhibitors of testosterone/DHT on the AR to prevent agonistic effects of the native androgens.

"Anabolic activity" refers, in one aspect, to increasing the mass of a connective tissue. In another aspect, "anabolic activity" refers to increasing the strength of a connective tissue. In one aspect, the connective tissue is cortical bone. In another aspect, the connective tissue is trabecular bone. In another aspect, the connective tissue is cancellous bone. In another aspect, the connective tissue is muscle. In another aspect, the connective tissue is cartilage. In another aspect, the connective tissue is any other type of connective tissue known in the art. Increases in the weight of the levator ani muscle were used in the present disclosure to demonstrate anabolic activity, and are accepted in the art as a reliable index of anabolic activity (Antonio J et al, "Effects of castration and androgen treatment on androgen-receptor levels in rat skeletal muscles," J Appl Physiol 87: 2016-2019, 1999). Anabolic activity in bone and muscle synergize, in one aspect, to decrease fracture rates in a subject.

The compounds of the present disclosure bind either reversibly or irreversibly to the androgen receptor. In one aspect, the SARM compounds bind reversibly to the androgen receptor. In another aspect, the SARM compounds bind irreversibly to the androgen receptor. The compounds of the present disclosure may contain a functional group (affinity label) that allows alkylation of the androgen receptor (i.e. covalent bond formation). Thus, in this case, the compounds bind irreversibly to the receptor and, accordingly, cannot be displaced by a steroid, such as the endogenous ligands DHT and testosterone.

As defined herein, "contacting" means that the SARM compound of the present disclosure is introduced into a sample containing the protein or enzyme in a test tube, flask, tissue culture, chip, array, plate, microplate, capillary, or the like, and incubated at a temperature and time sufficient to permit binding of the SARM to the enzyme. Methods for contacting the samples with the SARM or other specific binding components are known to those skilled in the art and may be selected depending on the type of assay protocol to be run. Incubation methods are also standard and are known to those skilled in the art.

In the methods and pharmaceutical compositions disclosed herein are not limited to any single class of compounds but rather include in the broadest scope, compounds that have affinity for the androgen receptor and can express at least some classic androgen activity, broadly thought of as AR agonists. One way to discern such activity preclinically, for example, is in a rat Herschberger assay where the effects of the prospective AR agonist are evaluated against a castrate background to determine if the compound has a stimulatory effect on androgen target tissues such as the levator ani, prostate and/or seminal vesicles. The AR agonists can be steroidal or non-steroidal, selective (e.g., a SARM) or not. In some aspects, the AR agonist is a steroidal AR agonist such as testosterone (and esters thereof), DHT (and esters thereof), fluoxymesterone, oxandrolone, stanzolol, methandrostenelone, methyltestosterone, oxymetholone, nandrolone (and esters thereof). In certain aspects, the AR agonists are SARMs (e.g., GTx-024). In certain aspects, SARMs demonstrate efficacy on tumor endpoints despite having reduced androgen drive on other tissues (e.g., prostate) or other expression profiles resulting in undesired outcomes such as virilization and hirsutism in females. In certain aspects, SARMs often present with reduced drive on liver enzymes elevations and/or possibly deleterious changes in cholesterol levels such as decreased HD1 and/or increased LDL. In certain aspects, SARMs are non-steroidal and do not present the potential class liability of 17alpha alkylated steroids though they still have good oral activity in general. In certain aspects, SARMs provide effective treatments that are less or non-virilizing. In certain aspects, SARMs are not likely to feedback stimulate the central hormonal axis.

In various aspects, a disclosed SARM includes, without limitation, GTx-024, 2-chloro-4-[[(1R,2R)-2-hydroxy-2-methyl-cyclopentyl]amino]-3-methyl-benzonitrile (J Med Chem 2016; 59(2) 750), tamoxifen, PF-06260414, enobosarm, AC-262,356, BMS-564929, LGD-2226, LGD-3303, LGD-4033, AC-262356, JNJ-28330835, GSK-2881078, RAD140, AZD-3514, MK4541, LG121071, GLPG0492, NEP28, YK11, MK0773, ACP-105, LY-2452473, S-101479, S-40542, S-40503, S-42, S-23, and the SARMs disclosed in U.S. Pat. Nos. 8,067,448; 9,133,182; and US Pat. Publ. No. 2016/0243224, each of which is incorporated herein by reference.

In some aspects, the SARM is a compound have a structure selected from:

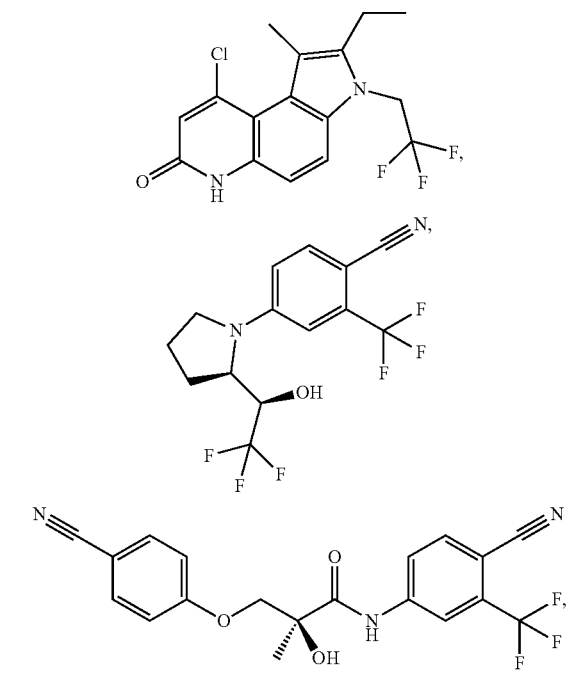

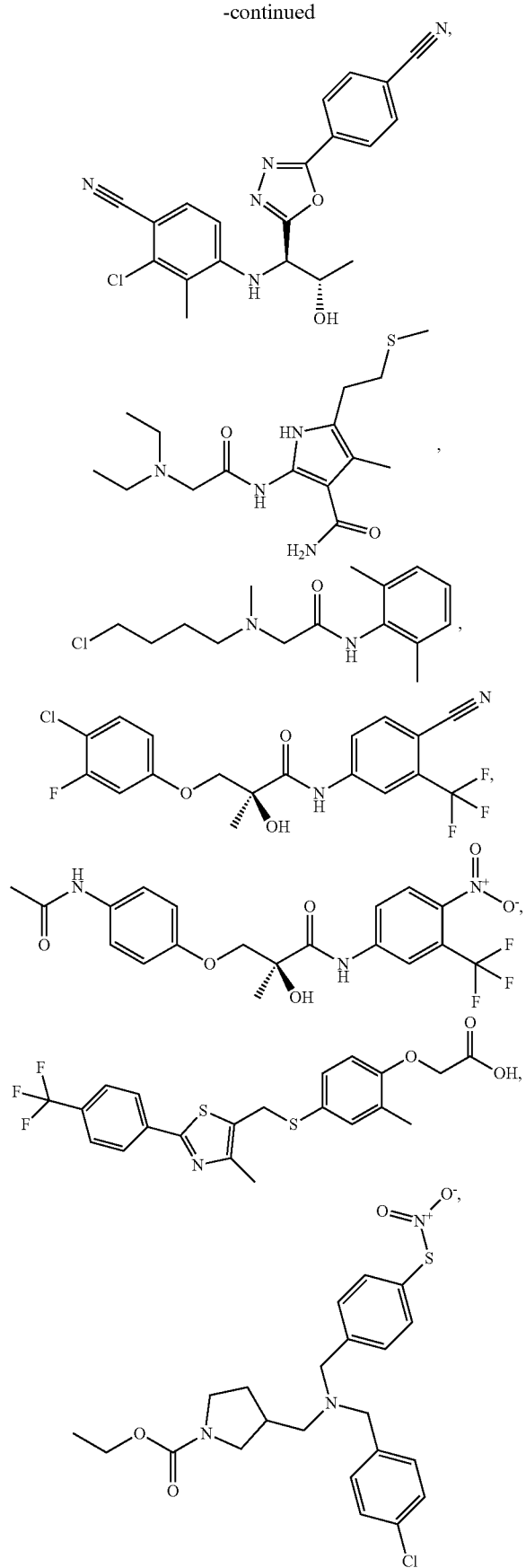

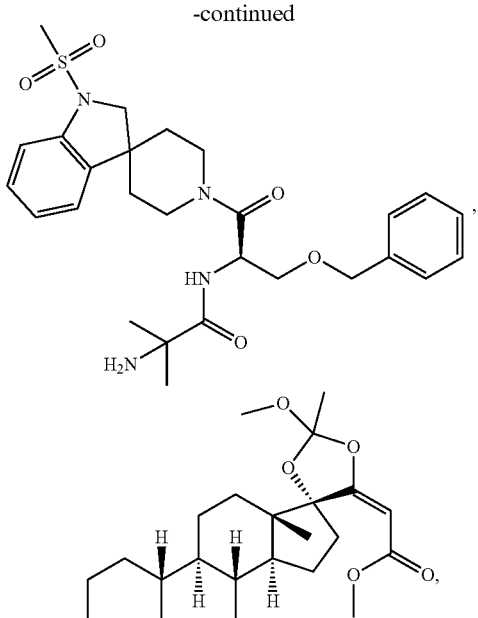

and combinations thereof.

In some aspects, the SARM is GTx-024 (also known as enobosarm, GTx 024 GTx-024, MK 2866, MK-2866, MK2866, and ostarine), with an IUPAC chemical name of (2S)-3-(4-cyanophenoxy)-N-(4-cyano-3-(trifluoromethyl) phenyl)-2-hydroxy-2-methylpropanamide, and represented by chemical structure of:

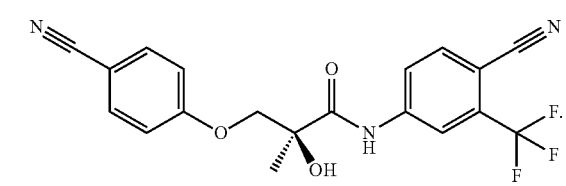 [SMILES: C[C@](O)(COc1ccc(C#N)cc1)C(=O)Nc1ccc(C#N)c(C(F)(F)F)c1]

In addition, the SARMs suitable for methods disclosed herein include compounds according to Formula I disclosed herein (e.g., Compound II and Compound III), and compounds according to Formula II disclosed herein, for the treatment of cancer cachexia when used in combination or co-administered with a Class I/IIB HDAC inhibitor compound.

Compounds according to Formula I include compounds having the structure of Formula I:

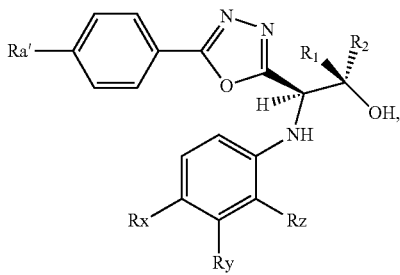

pharmaceutically acceptable salts thereof, and pharmaceutically acceptable solvates thereof, wherein:

$R_x$=CN;
$R_y$=CF$^3$ or Cl;
$R_z$=CH$_3$, CH$_2$CH$_3$ or Cl; or
$R_y$ and $R_z$ together form:

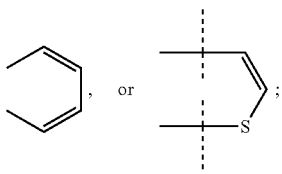

$R_{a'}$ is H, F, Cl, CN, OH or OSO$_3$; and
$R_1$ and $R_2$ are each independently selected from hydrogen and methyl.

In certain aspects, the compound according to Formula I is Compound II:

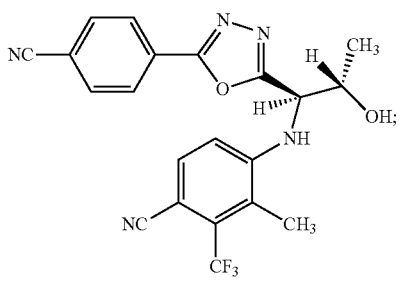 [SMILES: Cc1c(N[C@@H](c2nnc(-c3ccc(C#N)cc3)o2)[C@H](C)O)ccc(C#N)c1C(F)(F)F]

a pharmaceutically acceptable salt thereof, or pharmaceutically acceptable solvate thereof; or Compound III (RAD140):

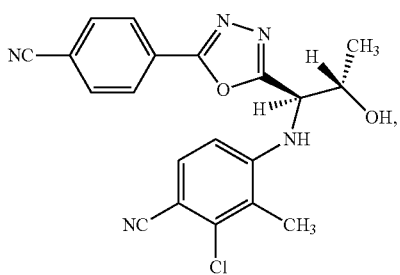 [SMILES: Cc1c(N[C@@H](c2nnc(-c3ccc(C#N)cc3)o2)[C@H](C)O)ccc(C#N)c1Cl]

a pharmaceutically acceptable salt thereof, or pharmaceutically acceptable solvate thereof.

In certain aspects, the compounds according to Formula II include:

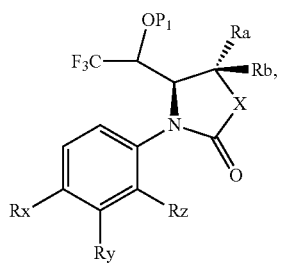

pharmaceutically acceptable salts thereof, and pharmaceutically acceptable solvates thereof, wherein:

Rx is CN, Cl, Br, or NO2;
Ry is CH3, CF3, or halogen;
Rz is hydrogen, optionally substituted C1-3 alkyl, optionally substituted C2-3 alkenyl, optionally substituted C1-3 hydroxyalkyl, optionally substituted C1-3 haloalkyl, NO2, NH2, OMe, halogen or OH;
P1 is hydrogen or a metabolically labile group;
Ra and Rb are each independently hydrogen or C1-3 alkyl; and
X is O.

Examples of optional substitution include, without limitation, 1-3 halogen atoms.

In certain aspects, the SARM is a compound according to Formula IV, a pharmaceutically acceptable salt thereof, or pharmaceutically acceptable solvate thereof, wherein Rx is CN.

In certain aspects, the SARM is a compound according to Formula IV, a pharmaceutically acceptable salt thereof, or pharmaceutically acceptable solvate thereof, wherein Rx is CN; Ry is Cl or CF3; Rz is hydrogen, Cl or CH3; P1 is (C=O)—C1-6 alkyl or hydrogen; and Ra and Rb are each independently hydrogen or —CH3.

In certain aspects, the SARM is a compound according to Formula IV, a pharmaceutically acceptable salt thereof, or pharmaceutically acceptable solvate thereof, wherein Rx is CN; Ry is Cl or CF3; Rz is hydrogen, Cl or CH3; P1 is (C=O)—C1-6 alkyl or hydrogen; and Ra and Rb are both hydrogen.

E. Pharmaceutical Compositions

In various aspects, the present disclosure relates to pharmaceutical compositions comprising a therapeutically effective amount of at least one disclosed Class I/IIB HDAC inhibitor, a pharmaceutically acceptable salt, a hydrate thereof, a solvate thereof, or a polymorph thereof; and/or at least one disclosed androgen or SARM, a pharmaceutically acceptable salt, a hydrate thereof, a solvate thereof, or a polymorph thereof. As used herein, "pharmaceutically-acceptable carriers" means one or more of a pharmaceutically acceptable diluents, preservatives, antioxidants, solubilizers, emulsifiers, coloring agents, releasing agents, coating agents, sweetening, flavoring and perfuming agents, and adjuvants. The disclosed pharmaceutical compositions can be conveniently presented in unit dosage form and prepared by any of the methods well known in the art of pharmacy and pharmaceutical sciences.

In a further aspect, the disclosed pharmaceutical compositions comprise a therapeutically effective amount of at least one disclosed Class I/IIB HDAC inhibitor, a pharmaceutically acceptable salt, a hydrate thereof, a solvate thereof, or a polymorph thereof; and/or at least one disclosed androgen or SARM, a pharmaceutically acceptable salt, a hydrate thereof, a solvate thereof, or a polymorph thereof, a pharmaceutically acceptable carrier, optionally one or more other therapeutic agent, and optionally one or more adjuvant. The disclosed pharmaceutical compositions include those suitable for oral, rectal, topical, pulmonary, nasal, and parenteral administration, although the most suitable route in any given case will depend on the particular host, and nature and severity of the conditions for which the active ingredient is being administered. In a further aspect, the disclosed pharmaceutical composition can be formulated to allow administration orally, nasally, via inhalation, parenterally, paracancerally, transmucosally, transdermally, intramuscularly, intravenously, intradermally, subcutaneously, intraperitonealy, intraventricularly, intracranially and intratumorally.

As used herein, "parenteral administration" includes administration by bolus injection or infusion, as well as administration by intravenous, intramuscular, intraarterial, intrathecal, intracapsular, intraorbital, intracardiac, intradermal, intraperitoneal, transtracheal, subcutaneous, subcuticular, intraarticular, subcapsular subarachnoid, intraspinal, epidural and intrasternal injection and infusion.

In various aspects, the present disclosure also relates to a pharmaceutical composition comprising a pharmaceutically acceptable carrier or diluent and, as active ingredient, a therapeutically effective amount of at least one disclosed Class I/II B HDAC inhibitor, a pharmaceutically acceptable salt, a hydrate thereof, a solvate thereof, or a polymorph thereof; and/or at least one disclosed androgen or SARM, a pharmaceutically acceptable salt, a hydrate thereof, a solvate thereof, or a polymorph thereof. In a further aspect, at least one disclosed Class I/II B HDAC inhibitor, a pharmaceutically acceptable salt, a hydrate thereof, a solvate thereof, or a polymorph thereof; and/or at least one disclosed androgen or SARM, a pharmaceutically acceptable salt, a hydrate thereof, a solvate thereof, or a polymorph thereof may be formulated into various pharmaceutical forms for administration purposes.

Pharmaceutically acceptable salts can be prepared from pharmaceutically acceptable non-toxic bases or acids. For therapeutic use, salts of the disclosed compounds are those wherein the counter ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are contemplated by the present disclosure. Pharmaceutically acceptable acid and base addition salts are meant to comprise the therapeutically active non-toxic acid and base addition salt forms which the disclosed compounds are able to form.

In various aspects, a disclosed compound comprising an acidic group or moiety, e.g., a carboxylic acid group, can be used to prepare a pharmaceutically acceptable salt. For example, such a disclosed compound may comprise an isolation step comprising treatment with a suitable inorganic or organic base. In some cases, it may be desirable in practice to initially isolate a compound from the reaction mixture as a pharmaceutically unacceptable salt and then simply convert the latter back to the free acid compound by treatment with an acidic reagent, and subsequently convert the free acid to a pharmaceutically acceptable base addition salt. These base addition salts can be readily prepared using conventional techniques, e.g., by treating the corresponding acidic compounds with an aqueous solution containing the desired pharmacologically acceptable cations and then evaporating the resulting solution to dryness, preferably under reduced pressure. Alternatively, they also can be prepared by mixing lower alkanolic solutions of the acidic compounds and the desired alkali metal alkoxide together, and then evaporating the resulting solution to dryness in the same manner as before.

Bases which can be used to prepare the pharmaceutically acceptable base-addition salts of the base compounds are those which can form non-toxic base-addition salts, i.e., salts containing pharmacologically acceptable cations such as, alkali metal cations (e.g., lithium, potassium and sodium), alkaline earth metal cations (e.g., calcium and magnesium), ammonium or other water-soluble amine addition salts such as N-methylglucamine-(meglumine), lower alkanolammonium and other such bases of organic amines. In a further aspect, derived from pharmaceutically acceptable organic non-toxic bases include primary, secondary, and tertiary amines, as well as cyclic amines and substituted amines such as naturally occurring and synthesized substituted amines. In various aspects, such pharmaceutically acceptable organic non-toxic bases include, but are not limited to, ammonia, methylamine, ethylamine, propylamine, isopropylamine, any of the four butylamine isomers, betaine, caffeine, choline, dimethylamine, diethylamine, diethanolamine, dipropylamine, diisopropylamine, di-n-butylamine, N,N'-dibenzylethylenediamine, pyrrolidine, piperidine, morpholine, trimethylamine, triethylamine, tripropylamine, tromethamine, 2-diethylaminoethanol, 2-dimethylaminoethanol, ethanolamine, quinuclidine, pyridine, quinoline and isoquinoline; benzathine, N-methyl-D-glucamine, ethylenediamine, N-ethylmorpholine, N-ethylpiperidine, glucamine, glucosamine, methylglucamine, morpholine, piperazine, piperidine, polyamine resins, procaine, purines, theobromine, hydrabamine salts, and salts with amino acids such as, for example, histidine, arginine, lysine and the like. The foregoing salt forms can be converted by treatment with acid back into the free acid form.

In various aspects, a disclosed compound comprising a protonatable group or moiety, e.g., an amino group, can be used to prepare a pharmaceutically acceptable salt. For example, such a disclosed compound may comprise an isolation step comprising treatment with a suitable inorganic or organic acid. In some cases, it may be desirable in practice to initially isolate a compound from the reaction mixture as a pharmaceutically unacceptable salt and then simply convert the latter back to the free base compound by treatment with a basic reagent, and subsequently convert the free base to a pharmaceutically acceptable acid addition salt. These acid addition salts can be readily prepared using conventional techniques, e.g., by treating the corresponding basic compounds with an aqueous solution containing the desired pharmacologically acceptable anions and then evaporating the resulting solution to dryness, preferably under reduced pressure. Alternatively, they also can be prepared by treating the free base form of the disclosed compound with a suitable pharmaceutically acceptable non-toxic inorganic or organic acid.

Acids which can be used to prepare the pharmaceutically acceptable acid-addition salts of the base compounds are those which can form non-toxic acid-addition salts, i.e., salts containing pharmacologically acceptable anions formed from their corresponding inorganic and organic acids. Exemplary, but non-limiting, inorganic acids include hydrochloric hydrobromic, sulfuric, nitric, phosphoric and the like. Exemplary, but non-limiting, organic acids include acetic, benzenesulfonic, benzoic, camphorsulfonic, citric, ethanesulfonic, fumaric, gluconic, glutamic, isethionic, lactic, maleic, malic, mandelicmethanesulfonic, mucic, pamoic, pantothenic, succinic, tartaric, p-toluenesulfonic acid and the like. In a further aspect, the acid-addition salt comprises an anion formed from hydrobromic, hydrochloric, maleic, phosphoric, sulfuric, and tartaric acids.

In practice, the compounds of the present disclosure, or pharmaceutically acceptable salts thereof, of the present disclosure can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present disclosure can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the present disclosure, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

It is especially advantageous to formulate the aforementioned pharmaceutical compositions in unit dosage form for ease of administration and uniformity of dosage. The term "unit dosage form," as used herein, refers to physically discrete units suitable as unitary dosages, each unit containing a predetermined quantity of active ingredient calculated to produce the desired therapeutic effect in association with the required pharmaceutical carrier. That is, a "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets (including scored or coated tablets), capsules or pills for oral administration; single dose vials for injectable solutions or suspension; suppositories for rectal administration; powder packets; wafers; and segregated multiples thereof. This list of unit dosage forms is not intended to be limiting in any way, but merely to represent typical examples of unit dosage forms.

The pharmaceutical compositions disclosed herein comprise a compound of the present disclosure (or pharmaceutically acceptable salts thereof) as an active ingredient, a pharmaceutically acceptable carrier, and optionally one or more additional therapeutic agents. In various aspects, the disclosed pharmaceutical compositions can include a pharmaceutically acceptable carrier and a disclosed compound, or a pharmaceutically acceptable salt thereof. In a further aspect, a disclosed compound, or pharmaceutically acceptable salt thereof, can also be included in a pharmaceutical composition in combination with one or more other therapeutically active compounds. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Techniques and compositions for making dosage forms useful for materials and methods described herein are described, for example, in the following references: Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

The compounds described herein are typically to be administered in admixture with suitable pharmaceutical diluents, excipients, extenders, or carriers (termed herein as a pharmaceutically acceptable carrier, or a carrier) suitably selected with respect to the intended form of administration and as consistent with conventional pharmaceutical practices. The deliverable compound will be in a form suitable for oral, rectal, topical, intravenous injection or parenteral administration. Carriers include solids or liquids, and the type of carrier is chosen based on the type of administration being used. The compounds may be administered as a dosage that has a known quantity of the compound.

Because of the ease in administration, oral administration can be a preferred dosage form, and tablets and capsules represent the most advantageous oral dosage unit forms in which case solid pharmaceutical carriers are obviously employed. However, other dosage forms may be suitable depending upon clinical population (e.g., age and severity of clinical condition), solubility properties of the specific disclosed compound used, and the like. Accordingly, the disclosed compounds can be used in oral dosage forms such as pills, powders, granules, elixirs, tinctures, suspensions, syrups, and emulsions. In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

The disclosed pharmaceutical compositions in an oral dosage form can comprise one or more pharmaceutical excipient and/or additive. Non-limiting examples of suitable excipients and additives include gelatin, natural sugars such as raw sugar or lactose, lecithin, pectin, starches (for example corn starch or amylose), dextran, polyvinyl pyrrolidone, polyvinyl acetate, gum arabic, alginic acid, tylose, talcum, lycopodium, silica gel (for example colloidal), cellulose, cellulose derivatives (for example cellulose ethers in which the cellulose hydroxy groups are partially etherified with lower saturated aliphatic alcohols and/or lower saturated, aliphatic oxyalcohols, for example methyl oxypropyl cellulose, methyl cellulose, hydroxypropyl methyl cellulose, hydroxypropyl methyl cellulose phthalate), fatty acids as well as magnesium, calcium or aluminum salts of fatty acids with 12 to 22 carbon atoms, in particular saturated (for example stearates), emulsifiers, oils and fats, in particular vegetable (for example, peanut oil, castor oil, olive oil, sesame oil, cottonseed oil, corn oil, wheat germ oil, sunflower seed oil, cod liver oil, in each case also optionally hydrated); glycerol esters and polyglycerol esters of saturated fatty acids $C_{12}H_{24}O_2$ to $C_{18}H_{36}O_2$ and their mixtures, it being possible for the glycerol hydroxy groups to be totally or also only partly esterified (for example mono-, di- and triglycerides); pharmaceutically acceptable mono- or multivalent alcohols and polyglycols such as polyethylene glycol and derivatives thereof, esters of aliphatic saturated or unsaturated fatty acids (2 to 22 carbon atoms, in particular 10-18 carbon atoms) with monovalent aliphatic alcohols (1 to 20 carbon atoms) or multivalent alcohols such as glycols, glycerol, diethylene glycol, pentacrythritol, sorbitol, mannitol and the like, which may optionally also be etherified, esters of citric acid with primary alcohols, acetic acid, urea, benzyl benzoate, dioxolanes, glyceroformals, tetrahydrofurfuryl alcohol, polyglycol ethers with C1-C12-alcohols, dimethylacetamide, lactamides, lactates, ethylcarbonates, silicones (in particular medium-viscous polydimethyl siloxanes), calcium carbonate, sodium carbonate, calcium phosphate, sodium phosphate, magnesium carbonate and the like.

Other auxiliary substances useful in preparing an oral dosage form are those which cause disintegration (so-called disintegrants), such as: cross-linked polyvinyl pyrrolidone, sodium carboxymethyl starch, sodium carboxymethyl cellulose or microcrystalline cellulose. Conventional coating substances may also be used to produce the oral dosage form. Those that may for example be considered are: polymerizates as well as copolymerizates of acrylic acid and/or methacrylic acid and/or their esters; copolymerizates of acrylic and methacrylic acid esters with a lower ammonium group content (for example EudragitR RS), copolymerizates of acrylic and methacrylic acid esters and trimethyl ammonium methacrylate (for example EudragitR RL); polyvinyl acetate; fats, oils, waxes, fatty alcohols; hydroxypropyl methyl cellulose phthalate or acetate succinate; cellulose acetate phthalate, starch acetate phthalate as well as polyvinyl acetate phthalate, carboxy methyl cellulose; methyl cellulose phthalate, methyl cellulose succinate, -phthalate succinate as well as methyl cellulose phthalic acid half ester; zein; ethyl cellulose as well as ethyl cellulose succinate; shellac, gluten; ethylcarboxyethyl cellulose; ethacrylate-maleic acid anhydride copolymer; maleic acid anhydride-vinyl methyl ether copolymer; styrol-maleic acid copolymerizate; 2-ethyl-hexyl-acrylate maleic acid anhydride; crotonic acid-vinyl acetate copolymer; glutaminic acid/glutamic acid ester copolymer; carboxymethylethylcellulose glycerol monooctanoate; cellulose acetate succinate; polyarginine.

Plasticizing agents that may be considered as coating substances in the disclosed oral dosage forms are: citric and tartaric acid esters (acetyl-triethyl citrate, acetyl tributyl-, tributyl-, triethyl-citrate); glycerol and glycerol esters (glycerol diacetate, -triacetate, acetylated monoglycerides, castor oil); phthalic acid esters (dibutyl-, diamyl-, diethyl-, dimethyl-, dipropyl-phthalate), di-(2-methoxy- or 2-ethoxyethyl)-phthalate, ethylphthalyl glycolate, butylphthalylethyl glycolate and butylglycolate; alcohols (propylene glycol, polyethylene glycol of various chain lengths), adipates (diethyladipate, di-(2-methoxy- or 2-ethoxyethyl)-adipate; benzophenone; diethyl- and diburylsebacate, dibutylsuccinate, dibutyltartrate; diethylene glycol dipropionate; ethyleneglycol diacetate, -dibutyrate, -dipropionate; tributyl phosphate, tributyrin; polyethylene glycol sorbitan monooleate (polysorbates such as Polysorbar 50); sorbitan monooleate.

Moreover, suitable binders, lubricants, disintegrating agents, coloring agents, flavoring agents, flow-inducing agents, and melting agents may be included as carriers. The pharmaceutical carrier employed can be, for example, a solid, liquid, or gas. Examples of solid carriers include, but are not limited to, lactose, terra alba, sucrose, glucose, methylcellulose, dicalcium phosphate, calcium sulfate, mannitol, sorbitol talc, starch, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In various aspects, a binder can include, for example, starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. In a further aspect, a disintegrator can include, for example, starch, methyl cellulose, agar, bentonite, xanthan gum, and the like.

In various aspects, an oral dosage form, such as a solid dosage form, can comprise a disclosed compound that is attached to polymers as targetable drug carriers or as a prodrug. Suitable biodegradable polymers useful in achieving controlled release of a drug include, for example, polylactic acid, polyglycolic acid, copolymers of polylactic and polyglycolic acid, caprolactones, polyhydroxy butyric acid, polyorthoesters, polyacetals, polydihydropyrans, polycyanoacylates, and hydrogels, preferably covalently crosslinked hydrogels.

Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing a disclosed compound can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

In various aspects, a solid oral dosage form, such as a tablet, can be coated with an enteric coating to prevent ready decomposition in the stomach. In various aspects, enteric coating agents include, but are not limited to, hydroxypropylmethylcellulose phthalate, methacrylic acid-methacrylic acid ester copolymer, polyvinyl acetate-phthalate and cellulose acetate phthalate. Akihiko Hasegawa "Application of solid dispersions of Nifedipine with enteric coating agent to prepare a sustained-release dosage form" Chem. Pharm. Bull. 33:1615-1619 (1985). Various enteric coating materials may be selected on the basis of testing to achieve an enteric coated dosage form designed ab initio to have a preferable combination of dissolution time, coating thicknesses and diametral crushing strength (e.g., see S. C. Porter et al. "The Properties of Enteric Tablet Coatings Made From Polyvinyl Acetate-phthalate and Cellulose acetate Phthalate", J. Pharm. Pharmacol. 22:42p (1970)). In a further aspect, the enteric coating may comprise hydroxypropylmethylcellulose phthalate, methacrylic acid-methacrylic acid ester copolymer, polyvinyl acetate-phthalate and cellulose acetate phthalate.

In various aspects, an oral dosage form can be a solid dispersion with a water soluble or a water insoluble carrier. Examples of water soluble or water insoluble carrier include, but are not limited to, polyethylene glycol, polyvinylpyrrolidone, hydroxypropylmethyl-cellulose, phosphatidylcholine, polyoxyethylene hydrogenated castor oil, hydroxypropylmethylcellulose phthalate, carboxymethylethylcellulose, or hydroxypropylmethylcellulose, ethyl cellulose, or stearic acid.

In various aspects, an oral dosage form can be in a liquid dosage form, including those that are ingested, or alternatively, administered as a mouth wash or gargle. For example, a liquid dosage form can include aqueous suspensions, which contain the active materials in admixture with excipients suitable for the manufacture of aqueous suspensions. In addition, oily suspensions may be formulated by suspending the active ingredient in a vegetable oil, for example *arachis* oil, olive oil, sesame oil or coconut oil, or in a mineral oil such as liquid paraffin. Oily suspensions may also contain various excipients. The pharmaceutical compositions of the present disclosure may also be in the form of oil-in-water emulsions, which may also contain excipients such as sweetening and flavoring agents.

For the preparation of solutions or suspensions it is, for example, possible to use water, particularly sterile water, or physiologically acceptable organic solvents, such as alcohols (ethanol, propanol, isopropanol, 1,2-propylene glycol, polyglycols and their derivatives, fatty alcohols, partial esters of glycerol), oils (for example peanut oil, olive oil, sesame oil, almond oil, sunflower oil, soya bean oil, castor oil, bovine hoof oil), paraffins, dimethyl sulphoxide, triglycerides and the like.

In the case of a liquid dosage form such as a drinkable solutions, the following substances may be used as stabilizers or solubilizers: lower aliphatic mono- and multivalent alcohols with 2-4 carbon atoms, such as ethanol, n-propanol, glycerol, polyethylene glycols with molecular weights between 200-600 (for example 1 to 40% aqueous solution), diethylene glycol monoethyl ether, 1,2-propylene glycol, organic amides, for example amides of aliphatic C1-C6-carboxylic acids with ammonia or primary, secondary or tertiary C1-C4-amines or C1-C4-hydroxy amines such as urea, urethane, acetamide, N-methyl acetamide, N,N-diethyl acetamide, N,N-dimethyl acetamide, lower aliphatic amines and diamines with 2-6 carbon atoms, such as ethylene diamine, hydroxyethyl theophylline, tromethamine (for example as to 20% aqueous solution), aliphatic amino acids.

In preparing the disclosed liquid dosage form can comprise solubilizers and emulsifiers such as the following non-limiting examples can be used: polyvinyl pyrrolidone, sorbitan fatty acid esters such as sorbitan trioleate, phosphatides such as lecithin, acacia, tragacanth, polyoxyethylated sorbitan monooleate and other ethoxylated fatty acid esters of sorbitan, polyoxyethylated fats, polyoxyethylated oleotriglycerides, linolizated oleotriglycerides, polyethylene oxide condensation products of fatty alcohols, alkylphenols or fatty acids or also 1-methyl-3-(2-hydroxyethyl)imidazolidone-(2). In this context, polyoxyethylated means that the substances in question contain polyoxyethylene chains, the degree of polymerization of which generally lies between 2 and 40 and in particular between 10 and 20. Polyoxyethylated substances of this kind may for example be obtained by reaction of hydroxyl group-containing compounds (for example mono- or diglycerides or unsaturated compounds such as those containing oleic acid radicals) with ethylene oxide (for example 40 Mol ethylene oxide per 1 Mol glyceride). Examples of oleotriglycerides are olive oil, peanut oil, castor oil, sesame oil, cottonseed oil, corn oil. See also Dr. H. P. Fiedler "Lexikon der Hillsstoffe für Pharmazie, Kostnetik and angrenzende Gebiete" 1971, pages 191-195.

In various aspects, a liquid dosage form can further comprise preservatives, stabilizers, buffer substances, flavor correcting agents, sweeteners, colorants, antioxidants and complex formers and the like. Complex formers which may be for example be considered are: chelate formers such as ethylene diamine retrascetic acid, nitrilotriacetic acid, diethylene triamine pentacetic acid and their salts.

It may optionally be necessary to stabilize a liquid dosage form with physiologically acceptable bases or buffers to a pH range of approximately 6 to 9. Preference may be given to as neutral or weakly basic a pH value as possible (up to pH 8).

In order to enhance the solubility and/or the stability of a disclosed compound in a disclosed liquid dosage form, a parenteral injection form, or an intravenous injectable form, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the present disclosure in pharmaceutical compositions.

In various aspects, a disclosed liquid dosage form, a parenteral injection form, or an intravenous injectable form can further comprise liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Pharmaceutical compositions of the present disclosure suitable injection, such as parenteral administration, such as intravenous, intramuscular, or subcutaneous administration. Pharmaceutical compositions for injection can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present disclosure suitable for parenteral administration can include sterile aqueous or oleaginous solutions, suspensions, or dispersions. Furthermore, the compositions can be in the form of sterile powders for the extemporaneous preparation of such sterile injectable solutions or dispersions. In some aspects, the final injectable form is sterile and must be effectively fluid for use in a syringe. The pharmaceutical compositions should be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Injectable solutions, for example, can be prepared in which the carrier comprises saline solution, glucose solution or a mixture of saline and glucose solution. Injectable suspensions may also be prepared in which case appropriate liquid carriers, suspending agents and the like may be employed. In some aspects, a disclosed parenteral formulation can comprise about 0.01-0.1 M, e.g. about 0.05 M, phosphate buffer. In a further aspect, a disclosed parenteral formulation can comprise about 0.9% saline.

In various aspects, a disclosed parenteral pharmaceutical composition can comprise pharmaceutically acceptable carriers such as aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include but not limited to water, alcoholic/aqueous solutions, emulsions or suspensions, including saline and buffered media. Parenteral vehicles can include mannitol, normal serum albumin, sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like. In a further aspect, a disclosed parenteral pharmaceutical composition can comprise may contain minor amounts of additives such as substances that enhance isotonicity and chemical stability, e.g., buffers and preservatives. Also contemplated for injectable pharmaceutical compositions are solid form preparations that are intended to be converted, shortly before use, to liquid form preparations. Furthermore, other adjuvants can be included to render the formulation isotonic with the blood of the subject or patient.

In addition to the pharmaceutical compositions described herein above, the disclosed compounds can also be formulated as a depot preparation. Such long acting formulations can be administered by implantation (e.g., subcutaneously or intramuscularly) or by intramuscular injection. Thus, for example, the compounds can be formulated with suitable polymeric or hydrophobic materials (e.g., as an emulsion in an acceptable oil) or ion exchange resins, or as sparingly soluble derivatives, e.g., as a sparingly soluble salt.

Pharmaceutical compositions of the present disclosure can be in a form suitable for topical administration. As used herein, the phrase "topical application" means administration onto a biological surface, whereby the biological surface includes, for example, a skin area (e.g., hands, forearms, elbows, legs, face, nails, anus and genital areas) or a mucosal membrane. By selecting the appropriate carrier and optionally other ingredients that can be included in the composition, as is detailed herein below, the compositions of the present disclosure may be formulated into any form typically employed for topical application. A topical pharmaceutical composition can be in a form of a cream, an ointment, a paste, a gel, a lotion, milk, a suspension, an aerosol, a spray, foam, a dusting powder, a pad, and a patch. Further, the compositions can be in a form suitable for use in transdermal devices.

These formulations can be prepared, utilizing a compound of the present disclosure, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

Ointments are semisolid preparations, typically based on petrolatum or petroleum derivatives. The specific ointment base to be used is one that provides for optimum delivery for the active agent chosen for a given formulation, and, preferably, provides for other desired characteristics as well (e.g., emollience). As with other carriers or vehicles, an ointment base should be inert, stable, nonirritating and nonsensitizing. As explained in Remington: The Science and Practice of Pharmacy, 19th Ed., Easton, Pa.: Mack Publishing Co. (1995), pp. 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight.

Lotions are preparations that are to be applied to the skin surface without friction. Lotions are typically liquid or semiliquid preparations in which solid particles, including the active agent, are present in a water or alcohol base. Lotions are typically preferred for treating large body areas, due to the ease of applying a more fluid composition. Lotions are typically suspensions of solids, and oftentimes comprise a liquid oily emulsion of the oil-in-water type. It is generally necessary that the insoluble matter in a lotion be finely divided. Lotions typically contain suspending agents to produce better dispersions as well as compounds useful for localizing and holding the active agent in contact with the skin, such as methylcellulose, sodium carboxymethylcellulose, and the like.

Creams are viscous liquids or semisolid emulsions, either oil-in-water or water-in-oil. Cream bases are typically water-washable, and contain an oil phase, an emulsifier and an aqueous phase. The oil phase, also called the "internal" phase, is generally comprised of petrolatum and/or a fatty alcohol such as cetyl or stearyl alcohol. The aqueous phase typically, although not necessarily, exceeds the oil phase in volume, and generally contains a humectant. The emulsifier in a cream formulation is generally a nonionic, anionic, cationic or amphoteric surfactant. Reference may be made to Remington: The Science and Practice of Pharmacy, supra, for further information.

Pastes are semisolid dosage forms in which the bioactive agent is suspended in a suitable base. Depending on the nature of the base, pastes are divided between fatty pastes or those made from a single-phase aqueous gel. The base in a fatty paste is generally petrolatum, hydrophilic petrolatum and the like. The pastes made from single-phase aqueous gels generally incorporate carboxymethylcellulose or the like as a base. Additional reference may be made to Remington: The Science and Practice of Pharmacy, for further information.

Gel formulations are semisolid, suspension-type systems. Single-phase gels contain organic macromolecules distributed substantially uniformly throughout the carrier liquid, which is typically aqueous, but also, preferably, contain an alcohol and, optionally, an oil. Preferred organic macromolecules, i.e., gelling agents, are crosslinked acrylic acid polymers such as the family of carbomer polymers, e.g., carboxypolyalkylenes that may be obtained commercially under the trademark Carbopol™. Other types of preferred polymers in this context are hydrophilic polymers such as polyethylene oxides, polyoxyethylene-polyoxypropylene copolymers and polyvinylalcohol; modified cellulose, such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Sprays generally provide the active agent in an aqueous and/or alcoholic solution which can be misted onto the skin for delivery. Such sprays include those formulated to provide for concentration of the active agent solution at the site of administration following delivery, e.g., the spray solution can be primarily composed of alcohol or other like volatile liquid in which the active agent can be dissolved. Upon delivery to the skin, the carrier evaporates, leaving concentrated active agent at the site of administration.

Foam compositions are typically formulated in a single or multiple phase liquid form and housed in a suitable container, optionally together with a propellant which facilitates the expulsion of the composition from the container, thus transforming it into a foam upon application. Other foam forming techniques include, for example the "Bag-in-a-can" formulation technique. Compositions thus formulated typically contain a low-boiling hydrocarbon, e.g., isopropane. Application and agitation of such a composition at the body temperature cause the isopropane to vaporize and generate the foam, in a manner similar to a pressurized aerosol foaming system. Foams can be water-based or aqueous alkanolic, but are typically formulated with high alcohol content which, upon application to the skin of a user, quickly evaporates, driving the active ingredient through the upper skin layers to the site of treatment.

Skin patches typically comprise a backing, to which a reservoir containing the active agent is attached. The reservoir can be, for example, a pad in which the active agent or composition is dispersed or soaked, or a liquid reservoir. Patches typically further include a frontal water permeable adhesive, which adheres and secures the device to the treated region. Silicone rubbers with self-adhesiveness can alternatively be used. In both cases, a protective permeable layer can be used to protect the adhesive side of the patch prior to its use. Skin patches may further comprise a removable cover, which serves for protecting it upon storage.

Examples of patch configuration which can be utilized with the present disclosure include a single-layer or multi-layer drug-in-adhesive systems which are characterized by the inclusion of the drug directly within the skin-contacting adhesive. In such a transdermal patch design, the adhesive not only serves to affix the patch to the skin, but also serves as the formulation foundation, containing the drug and all the excipients under a single backing film. In the multi-layer drug-in-adhesive patch a membrane is disposed between two distinct drug-in-adhesive layers or multiple drug-in-adhesive layers are incorporated under a single backing film.

Examples of pharmaceutically acceptable carriers that are suitable for pharmaceutical compositions for topical applications include carrier materials that are well-known for use in the cosmetic and medical arts as bases for e.g., emulsions, creams, aqueous solutions, oils, ointments, pastes, gels, lotions, milks, foams, suspensions, aerosols and the like, depending on the final form of the composition. Representative examples of suitable carriers according to the present disclosure therefore include, without limitation, water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials commonly employed in cosmetic and medicinal compositions. Other suitable carriers according to the present disclosure include, without limitation, alcohols, such as, for example, monohydric and polyhydric alcohols, e.g., ethanol, isopropanol, glycerol, sorbitol, 2-methoxyethanol, diethyleneglycol, ethylene glycol, hexyleneglycol, mannitol, and propylene glycol; ethers such as diethyl or dipropyl ether; polyethylene glycols and methoxypolyoxyethylenes (carbowaxes having molecular weight ranging from 200 to 20,000); polyoxyethylene glycerols, polyoxyethylene sorbitols, stearoyl diacetin, and the like.

Topical compositions of the present disclosure can, if desired, be presented in a pack or dispenser device, such as an FDA-approved kit, which may contain one or more unit dosage forms containing the active ingredient. The dispenser device may, for example, comprise a tube. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising the topical composition of the disclosure formulated in a pharmaceutically acceptable carrier may also be prepared, placed in an appropriate container, and labeled for treatment of an indicated condition.

Another patch system configuration which can be used by the present disclosure is a reservoir transdermal system design which is characterized by the inclusion of a liquid compartment containing a drug solution or suspension separated from the release liner by a semi-permeable membrane and adhesive. The adhesive component of this patch system can either be incorporated as a continuous layer between the membrane and the release liner or in a concentric configuration around the membrane. Yet another patch system configuration which can be utilized by the present disclosure is a matrix system design which is characterized by the inclusion of a semisolid matrix containing a drug solution or suspension which is in direct contact with the release liner. The component responsible for skin adhesion is incorporated in an overlay and forms a concentric configuration around the semisolid matrix.

Pharmaceutical compositions of the present disclosure can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

Pharmaceutical compositions containing a compound of the present disclosure, and/or pharmaceutically acceptable salts thereof, can also be prepared in powder or liquid concentrate form.

The pharmaceutical composition (or formulation) may be packaged in a variety of ways. Generally, an article for distribution includes a container that contains the pharmaceutical composition in an appropriate form. Suitable containers are well known to those skilled in the art and include materials such as bottles (plastic and glass), sachets, foil blister packs, and the like. The container may also include a tamper proof assemblage to prevent indiscreet access to the contents of the package. In addition, the container typically has deposited thereon a label that describes the contents of the container and any appropriate warnings or instructions.

The disclosed pharmaceutical compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Pharmaceutical compositions comprising a disclosed compound formulated in a compatible pharmaceutical carrier may also be prepared, placed in an appropriate container, and labeled for treatment of an indicated condition.

The exact dosage and frequency of administration depends on the particular disclosed compound, a product of a disclosed method of making, a pharmaceutically acceptable salt, solvate, or polymorph thereof, a hydrate thereof, a solvate thereof, a polymorph thereof, or a stereochemically isomeric form thereof; the particular condition being treated and the severity of the condition being treated; various factors specific to the medical history of the subject to whom the dosage is administered such as the age; weight, sex, extent of disorder and general physical condition of the particular subject, as well as other medication the individual may be taking; as is well known to those skilled in the art. Furthermore, it is evident that said effective daily amount may be lowered or increased depending on the response of the treated subject and/or depending on the evaluation of the physician prescribing the compounds of the present disclosure.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

In the treatment conditions which require of treatment of cancer cachexia using at least one disclosed Class I/II B HDAC inhibitor and at least one disclosed androgen or SARM, an appropriate dosage level can generally be about 0.01 to 1000 mg per kg patient body weight per day and can be administered in single or multiple doses. In various aspects, the dosage level will be about 0.1 to about 500 mg/kg per day, about 0.1 to 250 mg/kg per day, or about 0.5 to 100 mg/kg per day. A suitable dosage level can be about 0.01 to 1000 mg/kg per day, about 0.01 to 500 mg/kg per day, about 0.01 to 250 mg/kg per day, about 0.05 to 100 mg/kg per day, or about 0.1 to 50 mg/kg per day. Within this range the dosage can be 0.05 to 0.5, 0.5 to 5.0 or to 50 mg/kg per day. For oral administration, the compositions are preferably provided in the form of tablets containing 1.0 to 1000 mg of the active ingredient, particularly 1.0, 5.0, 10, 15, 20, 25, 50, 75, 100, 150, 200, 250, 300, 400, 500, 600, 750, 800, 900 and 1000 mg of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

Such unit doses as described hereinabove and hereinafter can be administered more than once a day, for example, 2, 3, 4, 5 or 6 times a day. In various aspects, such unit doses can be administered 1 or 2 times per day, so that the total dosage for a 70 kg adult is in the range of 0.001 to about 15 mg per kg weight of subject per administration. In a further aspect, dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

The present disclosure is further directed to a method for the manufacture of a medicament for modulating cancer cachexia in mammals (e.g., humans) comprising combining one or more disclosed compounds, products, or compositions with a pharmaceutically acceptable carrier or diluent. Thus, in one aspect, the present disclosure further relates to a method for manufacturing a medicament comprising combining at least one disclosed Class I/II B HDAC inhibitor and at least one disclosed androgen or SARM with a pharmaceutically acceptable carrier or diluent.

The disclosed pharmaceutical compositions can further comprise other therapeutically active compounds, which are usually applied in the treatment of the above mentioned pathological or clinical conditions.

It is understood that the disclosed compositions can be prepared from the disclosed compounds. It is also understood that the disclosed compositions can be employed in the disclosed methods of using.

As already mentioned, the present disclosure relates to a pharmaceutical composition comprising a therapeutically effective amount of a disclosed Class I/II B HDAC inhibitor, a pharmaceutically acceptable salt, a hydrate thereof, a solvate thereof, or a polymorph thereof; a disclosed androgen or SARM, a pharmaceutically acceptable salt, a hydrate thereof, a solvate thereof, or a polymorph thereof and a pharmaceutically acceptable carrier. Additionally, the present disclosure relates to a process for preparing such a pharmaceutical composition, characterized in that a pharmaceutically acceptable carrier is intimately mixed with a therapeutically effective amount of a compound according to the present disclosure.

As already mentioned, the present disclosure also relates to a pharmaceutical composition comprising a disclosed compound, a product of a disclosed method of making, a pharmaceutically acceptable salt, a hydrate thereof, a solvate thereof, a polymorph thereof, and one or more other drugs in the treatment, prevention, control, amelioration, or reduction of risk of diseases or conditions for a disclosed compound or the other drugs may have utility as well as to the use of such a composition for the manufacture of a medicament. The present disclosure also relates to a combination of a disclosed Class I/II B HDAC inhibitor, a pharmaceutically acceptable salt, a hydrate thereof, a solvate thereof, or a polymorph thereof; and a disclosed androgen or SARM, a pharmaceutically acceptable salt, a hydrate thereof, a solvate thereof, or a polymorph thereof. The present disclosure also relates to such a combination for use as a medicine. The present disclosure also relates to a product comprising (a) a disclosed Class I/II B HDAC inhibitor, a pharmaceutically acceptable salt, a hydrate thereof, a solvate thereof, or a polymorph thereof; and (b) a disclosed androgen or SARM, a pharmaceutically acceptable salt, a hydrate thereof, a solvate thereof, or a polymorph thereof, as a combined preparation for simultaneous, separate or sequential use in the treatment or prevention of cancer cachexia in a mammal, including a human, the treatment or prevention of which is affected or facilitated by the modulatory effect of the disclosed Class I/II B HDAC inhibitor and the androgen or SARM. The different drugs of such a combination or product may be combined in a single preparation together with pharmaceutically acceptable carriers or diluents, or they may each be present in a separate preparation together with pharmaceutically acceptable carriers or diluents.

F. Methods of Treating Cancer Cachexia

In one aspect, the present disclosure relates to a method for treating a subject comprising the step of co-administering an effective amount of a combination of two or more therapeutic agents to the subject; wherein the subject has been diagnosed with a need for treatment of a muscle wasting disease or disorder prior to the administering step; and wherein the combination of two or more therapeutic agents comprises: a) one or more Class I/IIB HDAC inhibitor; and b) one or more therapeutic agents selected from: i) an androgen; and ii) a SARM.

In one aspect, the present disclosure relates to a method of suppressing muscle wasting disease or disorder by administering: a) one or more Class I/IIB HDAC inhibitor; and b) one or more therapeutic agents selected from: i) an androgen; and ii) a SARM; is in an amount effective to substantially maintain the mammal's weight compared to a mammal that does not receive the Class I/II B HDAC inhibitor and an androgen or SARM. In another aspect, the HDAC inhibitor is AR-42.

In one aspect, the present disclosure relates to a method for treating a subject comprising the step of co-administering an effective amount of a combination of two or more therapeutic agents to the subject; wherein the subject has been diagnosed with a need for treatment of cancer cachexia prior to the administering step; and wherein the combination of two or more therapeutic agents comprises: a) one or more Class I/IIB HDAC inhibitor; and b) one or more therapeutic agents selected from: i) an androgen; and ii) a SARM.

In one aspect, the present disclosure relates to a method of suppressing cachexia in a mammal with cancer by administering: a) one or more Class I/IIB HDAC inhibitor; and b) one or more therapeutic agents selected from: i) an androgen; and ii) a SARM; is in an amount effective to substantially maintain the mammal's weight compared to a mammal that does not receive the Class I/IIB HDAC inhibitor and an androgen or SARM. In another aspect, the HDAC inhibitor is AR-42.

In yet another aspect, the mammal's weight is not reduced by more than about 6% after about the first 15 days following treatment with AR-42.

In a further aspect, an effective amount is a therapeutically effective amount. In a still further aspect, an effective amount is a prophylactically effective amount.

In a further aspect, the subject is a mammal. In a still further aspect, the mammal is selected from a human, a swine, a horse, a cat, and a dog. In a yet further aspect, the mammal is a human. In an even further aspect, the subject is a bird.

In various aspects, an HDAC inhibitor and an androgen or SARM, that have therapeutic or clinical utility when combined or co-administered can be used to treat a muscle wasting disorder or disease. In one aspect, the muscle wasting disorder is due to a pathology, illness, disease or condition. In a further aspect, the pathology, illness, disease or condition associated with a cancer or disorder of uncontrolled cellular proliferation. In another aspect, the pathology, illness, disease or condition is chronic. In another aspect, the pathology, illness, disease or condition is genetic. In another aspect, the pathology, illness, disease or condition is neurological. In another aspect, the pathology, illness, disease or condition is infectious.

In another aspect, the pathology, illness, disease or condition is a Cancer, Muscular Dystrophy, a Muscular Atrophy, X-linked spinal-bulbar Muscular Atrophy (SBMA), a Cachexia, malnutrition, Leprosy, Diabetes, Renal Disease, Chronic Obstructive Pulmonary Disease (COPD), end stage Renal failure, Sarcopenia, Emphysema, Osteomalacia, HIV Infection, AIDS, or Cardiomyopathy.

In another aspect, the muscle wasting disorder is an age-associated muscle wasting disorder, a disuse deconditioning associated muscle wasting disorder, or the muscle wasting disorder occurs due to chronic lower back pain, burns, central nervous system (CNS) injury or damage, peripheral nerve injury or damage, spinal cord injury or damage, chemical injury or damage, or alcoholism. In another aspect, the muscle wasting disorder is a chronic muscle wasting disorder.

A muscle is a tissue of the body that primarily functions as a source of power. There are three types of muscles in the body: a) skeletal muscle—the muscle responsible for moving extremities and external areas of the bodies; b) cardiac muscle—the heart muscle; and c) smooth muscle—the muscle that is in the walls of arteries and bowel.

A wasting condition or disorder is defined herein as a condition or disorder that is characterized, at least in part, by an abnormal, progressive loss of body, organ or tissue mass. A wasting condition can occur as a result of a pathology such as, for example, cancer, or it can be due to a physiologic or metabolic state, such as disuse deconditioning that can occur, for example, due to prolonged bed rest or when a limb is immobilized, such as in a cast. A wasting condition can also be age associated. The loss of body mass that occurs during a wasting condition can be characterized by a loss of total body weight, or a loss of organ weight such as a loss of bone or muscle mass due to a decrease in tissue protein.

In one aspect, "muscle wasting" or "muscular wasting", used herein interchangeably, refer to the progressive loss of muscle mass and/or to the progressive weakening and degeneration of muscles, including the skeletal or voluntary muscles which control movement, cardiac muscles which control the heart, and smooth muscles. In one aspect, the muscle wasting condition or disorder is a chronic muscle wasting condition or disorder. "Chronic muscle wasting" is defined herein as the chronic (i.e. persisting over a long period of time) progressive loss of muscle mass and/or to the chronic progressive weakening and degeneration of muscle.

The loss of muscle mass that occurs during muscle wasting can be characterized by a muscle protein breakdown or degradation, by muscle protein catabolism. Protein catabolism occurs because of an unusually high rate of protein degradation, an unusually low rate of protein synthesis, or a combination of both. Protein catabolism or depletion, whether caused by a high degree of protein degradation or a low degree of protein synthesis, leads to a decrease in muscle mass and to muscle wasting. The term "catabolism" has its commonly known meaning in the art, specifically an energy burning form of metabolism.

Muscle wasting can occur as a result of a pathology, disease, condition or disorder. In one aspect, the pathology, illness, disease or condition is a cancer or disorder of uncontrolled cellular proliferation. In one aspect, the pathology, illness, disease or condition is chronic. In another aspect, the pathology, illness, disease or condition is genetic. In another aspect, the pathology, illness, disease or condition is neurological. In another aspect, the pathology, illness, disease or condition is infectious. As described herein, the pathologies, diseases, conditions or disorders for which the compounds and compositions of the present disclosure are administered are those that directly or indirectly produce a wasting (i.e. loss) of muscle mass, that is a muscle wasting disorder.

In various aspects, the muscle wasting disease or disorder is a cachexia. Cachexia is weakness and a loss of weight caused by a disease or as a side effect of illness. Cancer cachexia is a syndrome that occurs in patients with solid tumors and hematological malignancies and is manifested by weight loss with massive depletion of both adipose tissue and lean muscle mass. Cardiac cachexia, i.e. a muscle protein wasting of both the cardiac and skeletal muscle, is a characteristic of congestive heart failure. Acquired Immunodeficiency Syndrome (AIDS). Cachexia is a Human Immunodeficiency Virus (HIV) associated myopathy and/or muscle weakness/wasting that is a relatively common clinical manifestation of AIDS. Individuals with HIV-associated myopathy or muscle weakness or wasting typically experience significant weight loss, generalized or proximal muscle weakness, tenderness, and muscle atrophy.

These include but are not limited to Muscular Dystrophies; Muscle Atrophies; Cachexias; malnutrition, Leprosy, Diabetes, Renal Disease, Chronic Obstructive Pulmonary Disease (COPD), Cancer, end stage Renal failure, Sarcopenia, Emphysema, Osteomalacia, HIV Infection, AIDS, or Cardiomyopathy.

In another aspect, the muscle wasting disorder is due to an infectious disease such as enterovirus, Epstein-Barr virus, herpes zoster, HIV, trypanosomiasis, influenze, coxsacke, infectious mononucleosis, *Rickettsia, Trichinella*, or Schistosomiasis.

The muscular dystrophies are genetic diseases characterized by progressive weakness and degeneration of the skeletal or voluntary muscles that control movement. The muscles of the heart and some other involuntary muscles are also affected in some forms of muscular dystrophy. The major forms of Muscular Dystrophy are: Duchenne Muscular Dystrophy, Myotonic Dystrophy, Duchenne Muscular Dystrophy, Becker Muscular Dystrophy, Limbgirdle Muscular Dystrophy, Facioscapulhumeral Muscular Dystrophy, Congenital Muscular Dystrophy, Oculopharyngeal Muscular Dystrophy, Distal Muscular Dystrophy and Emery-Dreifuss Muscular Dystrophy.

Muscular Dystrophy can affect people of all ages. Although some forms first become apparent in infancy or childhood, others may not appear until middle age or later. Duchenne Muscular Dystrophy is the most common kind of Muscular Dystrophy affecting children. Myotonic Dystrophy is the most common of these diseases in adults.

Muscle Atrophy is characterized by wasting away or diminution of muscle and a decrease in muscle mass. For example, Post-Polio Muscular Atrophy is a muscle wasting that occurs as part of the Post-Polio Syndrome (PPS). The Atrophy includes weakness, muscle fatigue, and pain.

Another type of Muscular Atrophy is X-linked spinal-bulbar Muscular Atrophy (SBMA—also known as Kennedy's Disease). This disease arises from a defect in the androgen receptor gene on the X chromosome, affects only males, and its onset is in adulthood. Because the primary disease cause is an androgen receptor mutation, androgen replacement is nota current therapeutic strategy. There are some investigational studies where exogenous testosterone propionate is being given to boost the levels of androgen with hopes of overcoming androgen insensitivity and perhaps provide an anabolic effect. Still, use of supraphysiological levels of testosterone for supplementation will have limitations and other potentially serious complications.

Sarcopenia is a debilitating disease that afflicts the elderly and chronically ill patients and is characterized by loss of muscle mass and function. Further, increased lean body mass is associated with decreased morbidity and mortality for certain muscle-wasting disorders. In addition, other circumstances and conditions are linked to, and can cause muscle wasting disorders. For example, studies have shown that in severe cases of chronic lower back pain, there is paraspinal muscle wasting.

Muscle wasting is also associated with advanced age. It is believed that general weakness in old age is due to muscle wasting. As the body ages, an increasing proportion of skeletal muscle is replaced by fibrous tissue. The result is a significant reduction in muscle power, performance and endurance.

Long term hospitalization due to illness or injury, or disuse deconditioning that occurs, for example, when a limb is immobilized, can also lead to muscle wasting. Studies have shown that in patients suffering injuries, chronic illnesses, burns, trauma or cancer, who are hospitalized for long periods of time, there is a long-lasting unilateral muscle wasting, with a consequent decrease in body mass.

Injuries or damage to the Central Nervous System (CNS) are also associated with muscle wasting disorders. Injuries or damage to the CNS can be, for example, caused by diseases, trauma or chemicals. Examples are central nerve injury or damage, peripheral nerve injury or damage and spinal cord injury or damage.

Finally, alcoholism has been shown to be associated with muscle wasting disorders.

In a further aspect, the co-administration is administration in a substantially simultaneous manner. In a still further aspect, the simultaneous administration comprises a single dose form containing a fixed ratio of the Class I/IIB HDAC inhibitor compound and the androgen or SARM. In a yet further aspect, the single dose form containing a fixed ratio of the Class I/IIB HDAC inhibitor compound and the androgen or SARM is a capsule or a tablet. In an even further aspect, the single dose form containing a fixed ratio of the Class I/IIB HDAC inhibitor compound and the androgen or SARM is an ampule for a single intravenous administration. In a still further aspect, the simultaneous administration comprises a single dose forms for each of the Class I/IIB HDAC inhibitor compound and the androgen or SARM. In a yet further aspect, the single dose form for each of the Class I/IIB HDAC inhibitor compound and the androgen or SARM is a capsule or a tablet. In an even further aspect, the single dose form for each of the Class I/IIB HDAC inhibitor compound and the androgen or SARM an ampule for a single intravenous administration.

In a further aspect, the co-administration is administration in a substantially sequential manner.

The combination or co-administration of a disclosed Class I/IIB HDAC inhibitor and an androgen or SARM, can be administered to a cell, a tissue, or a subject to provide a therapeutic effect. Methods for the safe and effective administration of the compounds of the disclosure are known to those skilled in the art. For instance, the administration of HDACs inhibitors is described in the literature.

Dosages of a disclosed Class I/IIB HDAC inhibitor or an androgen or SARM of the disclosure can independently range from about 0.1 µg/day to 10,000 mg/day, from about 1 µg/day to 1000 mg/day, and from about 10 µg/day to 100 mg/day, and any and all whole or partial increments there between.

Stated in terms of subject body weight, dosages of a disclosed Class I/IIB HDAC inhibitor or an androgen or SARM of the disclosure can independently from about 0.1 µg/kg/day to about 1000 mg/kg/day, from about 10 µg/kg/day to about 500 mg/kg/day, from about 20 µg/kg/day to about 100 mg/kg/day, from about 50 µg/kg/day to about 50 mg/kg/day, and from about 0.10 mg/kg/day to about 5 mg/kg/day, and any and all whole or partial increments there between.

Oral dosages of a disclosed Class I/IIB HDAC inhibitor or an androgen or SARM of the disclosure can independently range from about 0.1 µg/day to about 10,000 mg/day, from about 1 µg/day to about 1000 mg/day, from about 10 µg/day to about 100 mg/day, and from about 8 mg/day to about 80 mg/day, and any and all whole or partial increments there between.

Stated in terms of subject body weight, oral dosages of a disclosed Class I/IIB HDAC inhibitor or an androgen or SARM of the disclosure can independently range from about 0.1 µg/kg/day to about 1000 mg/kg/day, from about 10 µg/kg/day to about 500 mg/kg/day, from about 20 µg/kg/day to about 100 mg/kg/day, from about 50 µg/kg/day to about 50 mg/kg/day, and from about 0.10 mg/kg/day to about 5 mg/kg/day, and any and all whole or partial increments there between.

A disclosed Class I/IIB HDAC inhibitor or an androgen or SARM of the disclosure\for administration can be administered in a dose independently ranging of from about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 µg to about 3,500 mg, about 5 µg to about 3,000 mg, about 10 µg to about 2,600 mg, about 20 µg to about 2,575 mg, about 30 µg to about 2,550 mg, about 40 µg to about 2,500 mg, about 50 µg to about 2,475 mg, about 100 µg to about 2,450 mg, about 200 µg to about 2,425 mg, about 300 µg to about 2,000, about 400 µg to about 1,175 mg, about 500 µg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg, and any and all whole or partial increments there between.

In some aspects, a disclosed Class I/IIB HDAC inhibitor or an androgen or

SARM of the disclosure can independently have a dose of from about 0.0001 mg to about 25 mg. In some aspects, a disclosed Class I/IIB HDAC inhibitor or an androgen or SARM of the disclosure can independently have a dose of less than about 1000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments there between.

G. Kits

The disclosed compounds and/or pharmaceutical compositions comprising the disclosed compounds, i.e., one or more Class I/II B HDAC inhibitor and one or more androgen or SARM, can conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient. In further aspects, a kit can include optional components that aid in the administration of the unit dose to patients, such as vials for reconstituting powder forms, syringes for injection, customized IV delivery systems, inhalers, etc. Additionally, a kit can contain instructions for preparation and administration of the compositions. The kit can be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

In various aspects, the kit can be packaged with one or more therapeutic agents known to cause cancer cachexia.

In a further aspect, the one or more Class I/II B HDAC inhibitor and one or more androgen or SARM are co-formulated. In a still further aspect, one or more Class I/IIB HDAC inhibitor and one or more androgen or SARM are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of using or treatment.

In a further aspect, the disclosed kits can be packaged in a daily dosing regimen (e.g., packaged on cards, packaged with dosing cards, packaged on blisters or blow-molded plastics, etc.). Such packaging promotes products and increases patient compliance with drug regimens. Such packaging can also reduce patient confusion. The present disclosure also features such kits further containing instructions for use.

In a further aspect, the present disclosure also provides a pharmaceutical pack or kit comprising one or more containers filled with one or more of the ingredients of the pharmaceutical compositions of the disclosure. Associated with such container(s) can be a notice in the form prescribed by a governmental agency regulating the manufacture, use or sale of pharmaceuticals or biological products, which notice reflects approval by the agency of manufacture, use or sale for human administration.

In various aspects, the disclosed kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using or treating, and/or the disclosed compositions.

In various aspects, a disclosed kit can comprise one or more Class I/II B HDAC inhibitor and one or more androgen or SARM, and instructions for the timing of administration of each of the one or more Class I/IIB HDAC inhibitor and the one or more androgen or SARM.

H. Research Tools

The disclosed compounds and pharmaceutical compositions have activity useful as research tools for the study of cancer cachexia in model systems, e.g., a research animal used to study cancer cachexia. As such, the disclosed compounds are also useful as research tools. Accordingly, one aspect of the present disclosure relates to a method of using one or more disclosed Class I/II B HDAC inhibitor and one or more disclosed androgen or SARM of the disclosure as a research tool, the method comprising conducting a biological assay using a disclosed one or more Class I/IIB HDAC inhibitor and one or more androgen or SARM. Compounds of the disclosure can also be used to evaluate new chemical compounds. Thus another aspect of the disclosure relates to a method of evaluating a test compound in a biological assay, comprising: (a) conducting a biological assay with a test compound to provide a first assay value; (b) conducting the biological assay with a disclosed one or more Class I/II B HDAC inhibitor and one or more androgen or SARM to provide a second assay value; wherein step (a) is conducted either before, after or concurrently with step (b); and (c) comparing the first assay value from step (a) with the second assay value from step (b). Exemplary biological assays include the mouse cancer cachexia model system, e.g., the colon 26 (C-26) tumor model of cancer cachexia, a fragment of the C26 tumor is grafted in isogenic BALB/c mice and the mice develop an undifferentiated carcinoma. In various aspects, a mouse cancer cachexia model system can use CD2F1 mice instead of BALB/c mice. In such an assay system, skeletal muscle atrophy (measured by muscle force and resistance to fatigue) can be correlated with the observed biochemical changes and the model was described as a "well standardized experimental model for research on cancer cachexia." BMC Cancer. 2010 Jul. 8; 10:363. Still another aspect of the disclosure relates to a method of studying a biological system, e.g., a model animal for a clinical condition, the method comprising: (a) contacting the biological system or sample with a disclosed one or more Class I/II B HDAC inhibitor and one or more androgen or SARM; and (b) determining the effects caused by the disclosed one or more Class I/II B HDAC inhibitor and one or more androgen or SARM on the biological system or sample.

Now having described the aspects of the present disclosure, in general, the following Examples describe some additional aspects of the present disclosure. While aspects of the present disclosure are described in connection with the following examples and the corresponding text and figures, there is no intent to limit 30 aspects of the present disclosure to this description. On the contrary, the intent is to cover all alternatives, modifications, and equivalents included within the spirit and scope of the present disclosure.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Overcoming Resistance to Anabolic Selective Androgen Receptor Modulator (SARM) Therapy in Experimental Cancer Cachexia with Histone Deacetylase Inhibitor AR-42

Materials and Methods

Animal studies using the C-26 colon adenocarcinoma cachexia model: These studies were performed as previously described (Tseng Y C, et al. J Natl Cancer Inst. 2015 107(12):djv274) with modifications. Tumors were established in the right flank by subcutaneous injection of C-26 cells (0.5×10 6 cells in 0.1 mL). AR-42, GTx-024 and their vehicles were administered orally by gavage. TFM-4AS-1 (a potent experimental SARM), dihydrotestosterone (DHT) and vehicles were administered by subcutaneous injection.

AR-42 dose-response study: Male CD2F1 mice were stratified by body weight and then randomly assigned into 5 groups of 6 animals each. C-26 tumors were established in four of the groups, while those in the fifth group, serving as tumor-free controls, were injected with sterile saline. Six days later, animals with palpable tumors were treated with AR-42 once daily at 10 (n=5) and 20 mg/kg (n=6), and every other day at 50 mg/kg (n=5), or vehicle control (n=4) for 13 days. Upon sacrifice on study day 18, when the majority of tumor-bearing control mice met euthanasia criteria, the left gastrocnemius muscle was excised and flash frozen in liquid nitrogen and stored at −80° C. for subsequent analyses. Carcass weights were corrected for tumor weight by assuming a tumor density equivalent to water (1 g/cm$^3$).

Initial AR-42/GTx-024 Combination Study (Study 1): Male CD2F1 mice were stratified by body weight and then randomly assigned into 6 groups of 6 animals each. Historically, 6 animals per group provided sufficient power to detect treatment-mediated differences in tumor-bearing treated animals compared to controls. Tumors were established in four of the groups, while the fifth and sixth groups served as tumor-free controls. Six days later, animals with palpable tumors were treated twice daily for 13 days. AR-42 and its vehicle were administered in the mornings, and GTx-024 and its vehicle in the afternoons. Treatments included vehicles for AR-42 and GTx-024 (n=5), GTx-024 (15 mg/kg; AR-42 vehicle; n=5), AR-42 (10 mg/kg; GTx-024 vehicle; n=5), or the AR-42+GTx-024 combination (10 and 15 mg/kg, respectively; n=5). The remaining tumor-free groups received either vehicles (n=6) or GTx-024 (15 mg/kg; AR-42 vehicle; n=6). Body weight, tumor volume, and feed consumption were monitored every other day. Upon sacrifice on day 18, sera were collected and hind limb skeletal muscles, heart, spleen and epididymal adipose tissues were harvested, weighed, flash frozen, and stored for subsequent analyses.

Confirmatory AR-42/GTx-024 Combination Study (Study 2): This confirmatory study was performed exactly as Study 1 with expanded animal numbers. Tumor-free control groups were maintained at 6 animals each, whereas 10 animals were included in each of the tumor-bearing groups. Six days after cell injection, animals with palpable tumors were treated as in Study 1 with vehicles (n=7), GTx-024 (n=10), AR-42 (n=9), or the combination (n=9). Grip strength was measured on study days 0 (baseline) and 16. Due to rapid model progression, this study was terminated after only 12 days of treatment.

Combined Androgen and AR-42 Study (Study 3): Similar to Study 2, the tumor-free control group was maintained at 6 animals, whereas 10 animals were included in each of the 6 tumor-bearing groups. Six days after cell injection, animals with palpable tumors were treated once daily for 13 days with vehicles for AR-42 and TFM-4AS-1/DHT (n=9), AR-42 (10 mg/kg; TFM-4AS-1/DHT vehicle; n=10), TFM-4AS-1 (10 mg/kg; AR-42 vehicle; n=9), DHT (3 mg/kg; AR-42 vehicle; n=10), the combination of AR-42 and TFM-4AS-1 (10 mg/kg each; n=9), or the combination of AR-42 (10 mg/kg) and DHT (3 mg/kg)(n=10). Grip strength was measured and tissues collected as in the previous studies.

AR-42 Plasma and Tissue Pharmacokinetics: Pharmacokinetic studies were performed as previously described (Cheng H et. al.. AAPS J. 2016 18(3):737-45).

Statistical Methodology: Plotting and statistical analyses were performed using GraphPad Prism Version 7 (GraphPad Software, La Jolla, CA). The specific statistical tests employed are outlined in detail within the figure legends.

Reagents and chemicals: GTx-024 [(S)—N-(4-cyano-3-(trifluoromethyl)phenyl)-3-(4-cyanophenoxy)-2-hydroxy-2-methylpropanamide] was synthesized as previously described (Kim J, et al. J Pharmacol Exp Ther. 2005 315(1):230-9) and its purity (99.26%) confirmed internally by LC-MS. AR-42 was generously provided by Arno Therapeutics, Inc. (Fairfield, NJ) and TFM-4-AS-1 (Sigma Aldrich, Saint Louis, MO) and dihydrotestosterone (DHT; Steraloids, Newport, RI) were purchased from commercial sources.

Vehicle components included: Captex (Abitec, Columbus, OH), Tween 20 (Sigma Aldrich, Saint Louis, MO), benzyl alcohol (Sigma Aldrich, Saint Louis, MO) and sesame oil (Sigma Aldrich, Saint Louis, MO). AR-42 was formulated in 0.5% methylcellulose [w/v] and 0.1% Tween-80 [v/v] in sterile water. GTx-024 (Narayanan R, et al. PloS one. 2014 9(7):e103202), DHT and TFM-4AS-1 (von Haehling S, et al. Int J Cardiol. 2015 184:736-42) were formulated as previously described. Remaining reagents were all purchased from Sigma-Aldrich (Saint Louis, MO) unless otherwise mentioned.

Cells: Cultured murine colon-26 (C-26) adenocarcinoma cells were maintained in fetal bovine serum (FBS)-supplemented (10%) RPMI 1640 medium (Invitrogen, Carlsbad, CA) at 37° C. in a humidified incubator with 5% $CO_2$. For injection into mice, cells were harvested by trypsinization, pelleted in FBS-supplemented culture medium, and then resuspended in sterile PBS at a concentration of 5×10$^6$ cells/ml.

Animals: Male CD2F1 mice (6-7 weeks of age; Harlan Laboratories, Indianapolis, IN) were group-housed under conditions of constant photoperiod (12-hour light/12-hour dark), temperature and humidity with ad libitum access to water and standard pelleted chow. Mice were briefly anesthetized (isoflurane) during administration of drugs (AR-42, GTx-024, vehicles) by oral gavage. In experiments in which food consumption was determined, the food in each cage was weighed daily and the daily decrease in food weight was divided by the number of mice in the cage. Tumor volumes were calculated from caliper measurements using a standard formula (length×width$^2$×π/6). Mice were euthanized by $CO_2$ inhalation.

Confirmation of Anabolic Activity of 15 mg/kg GTx-024: Eight week-old, male, tumor-free CD2F1 mice were surgically castrated under isoflurane anesthesia. Three weeks later, the mice were assigned to groups treated with GTx-024 (15 mg/kg; n=12) or vehicle (n=13) by oral gavage once daily for 4 weeks. A sham-castrated group was treated identically with vehicle (n=14). Body weights were measured twice weekly. Forelimb grip strength was measured one day prior to first treatment (baseline) and at end of study. At terminal sacrifice, hind limb muscles were removed and weighed.

Grip strength measurement: Forelimb grip strength was measured using Bio-GS3 Grip Strength Test Meter (Forceleader DBA Bioseb, Pinellas Park, FL). Each mouse was held by the base of its tail and lowered over the apparatus until its forepaws grasped the metal pull bar. The mouse was then gently pulled horizontally in a straight line away from the grip strength meter until the mouse released the bar. The force applied to the bar at the moment of release was recorded as the peak force. Five measurements were taken from each mouse, the average of which was designated as the mouse's grip strength.

AR-42 Plasma and Tissue Pharmacokinetics: Pharmacokinetic studies were performed as previously described (Cheng H, et al. AAPS J. 2016 18(3):737-45) with the following modifications. Seven week-old, male, tumor-free CD2F1 mice (n=3 per dose and time point) were administered single oral doses of 10, 20 and 50 mg/kg AR-42 and then sacrificed 0.25, 4 and 24 hours later. Fifty mg of gastrocnemius muscle tissue was flash frozen in 2 mL Beadblaster™ 24 (MI DSCI; St. Louis, MO) tubes and stored at −80° C. Samples were homogenized for 6-cycles using a Beadblaster 24 with analytical standards in 1 mL methanol and then centrifuged at 13,000 rpm (4° C.) for 10 min. Supernatants were transferred to glass tubes, dried under nitrogen, then reconstituted in 200 µL 40% methanol/0.1% formic acid. Plasma preparation and LC-MS/MS analyses were performed as previously described (Sborov D W, et al. Leuk Lymphoma 2017 58(10):2310-8). Mouse plasma and muscle pharmacokinetic parameters were estimated as previously described with the exception of $C_{avg}$ which was calculated as $AUC_{all}$/[Dosing Interval(h)].

In vitro HDAC inhibition assays: HDAC activity was measured by a commercial vendor using human recombinant HDAC enzymes and fluorogenic HDAC substrates (Eurofins Cerep SA, Celle L'Evescault, France). Substrate concentrations ranged from 20-400 µmol/L and incubation conditions ranged from 10-90 min (RT or 37° C.), depending on isoform. Results are expressed as percent inhibition of control specific activity in the presence of 1 µmol/L AR-42.

Cytokine Analyses: Serum cytokine panel analyses were performed by a commercial vendor (Eve Technologies, Calgary, Canada) as previously described [6]. Serum interleukin-6 (IL-6) was measured using a commercial ELISA kit (R&D Systems, Minneapolis, MN, USA) according to the manufacturer's instructions.

Luteinizing hormone analyses: Luteinizing hormone (LH) was measured in serum by a two-site sandwich radioimmunoassay performed by the Ligand Assay and Analysis Core at the Center for Research in Reproduction, University of Virginia School of Medicine (Charlottesville, VA). Serum was isolated by centrifugation (2000×g, 15 minutes) from whole blood samples collected from mice immediately post-mortem, and then stored at −80° C. until shipment on dry ice.

Gene Expression Analyses—qRT-PCR: To generate muscle tissue RNA, 15 mg of gastrocnemius muscle tissue was lysed in 10 volumes of lysis buffer per tissue mass in prefilled 2.0 ml tubes with 3.0 mm zirconium beads (MIDSCI; St. Louis, MO). Tubes were loaded into Beadblaster™ 24 (MIDSCI; St. Louis, MO) and centrifuged for 5 cycles of 5 seconds with a 30 second pause between cycles. Lysate was collected and RNA was isolated using the mirVana™ miRNA Isolation Kit, with phenol (ThermoFisher; Waltham, MA). Samples were treated with DNA-free DNA Removal Kit to eliminate any DNA contamination (Invitrogen, Carlsbad, CA). Total RNA (0.5 µg) was reverse-transcribed using high-capacity cDNA reverse transcription kit (Applied Biosystems, Foster City, CA) for 10 min at 25° C., 120 min at 37° C. and 5 min at 85° C. (T100™ Thermal Cycler, Bio Rad). Real-time qPCR was performed on the QuantStudio 7 system (Applied Biosystems, Foster City, CA) using the powerup SYBR green master mix (Applied Biosystems, Foster City, CA). Cycling was performed using the QuantStudio 7 real-time PCR software—2 min at 50° C. and 10 min at 95° C. —followed by 40 cycles of 15 s at 95° C. and 1 min at 60° C. All real-time qPCR assays were carried out using technical duplicates using β-actin or GAPDH as the internal control genes. Reaction specificity was supported by the detection of a single amplified product in all reactions by a post-cycling melt curve, the absence of non-template control signal for 40 cycles, and confirmation of amplicon size using agarose electrophoresis. Primers for analyses are listed in Table 2. Data are presented as per group geometric mean±geometric standard deviation (STD) and individual $2^{-deltaCt}$ values [deltaCt=(target gene−internal control)]. All values are normalized to the geometric mean tumor-free control values. As transformed expression data are not normally distributed, statistical differences between treatment groups were determined by one-way ANOVA followed by Dunnett's test on raw delta Ct values.

Pathway Enrichment Analyses: Overlap between the gene sets in Tseng et al. (Tseng Y C, et al. J Natl Cancer Inst. 2015 107(12):djv274) and Bonetto et al. (Bonetto A, et al. PloS one. 2011 6(7):e22538) were determined and plotted using the Venn Diagram web tool in the Bioinformatics and Evolutionary Genomics Suite (Ghent University, Ghent, Belgium). The lists of AR-42-regulated genes from Tseng et al., as well as genes regulated in common between Tseng et al. and Bonetto et al. were tested for significant overlap with Canonical Pathway gene sets using the 'Compute Overlaps' function from the Molecular Signatures Database (Broad Institute, Cambridge, MA). Redundant results were collapsed to show only the gene set with the largest number of genes.

Gene Expression Analyses—RNA-seq: For each sample, 600 ng total RNA (Bioanalyzer RIN values >7) was used to generate polyA enriched RNA-seq libraries with the NEBNext Ultra II Directional RNA Library Prep Kit (New England Biolabs, Inc., catolog number E7760) and sequenced as PE-150 reads on HiSeq 4000 (Illumina Inc, San Diego, CA). Raw fastq files were adaptor trimmed using Trimmomatic (Bolger, A. M., et al. Bioinformatics 2014 30(15):2114-2120), aligned to the mm10 genome with Subread (Liao Y, et al. Nucleic Acids Res. 2013 41(10):e108), and marked for duplicate reads with Picard v2.3.0. Samtools (Li H., et al. Bioinformatics 2014 25:2078-9) was used to calculate post-alignment quality control metrics (Table 3). A gene-based counts matrix was generated with the summarizeOverlaps function of GenomicAlignments (Lawrence M, et al. PLoS Comput Biol 9(8):e1003118) and analyzed with DESeq2 (Love, M. I., et al. Genome biology 15(12):550) for genes differentially expressed among groups. GSEAPreranked analyses (Subramanian A, et al. Proc Natl Acad Sci USA. 2005 102:15545-15550) were performed using the signed log 10 p-values for each gene to test for significant enrichment of gene sets in the 'TF Targets' file downloaded from ge-lab.org/#/data. Any duplication in signed log 10 p-values was removed prior to running the GSEAPreranked analyses by adding a small value sampled at random from a normal distribution with mean zero and standard deviation 0.00001 to each duplicated value. GSEAPreranked analyses were performed in classic mode on gene sets with a minimum and maximum of 5 and 5000 genes in the gene set, respectively, and were followed by leading-edge analyses for selected comparison and gene set combinations. Heatmaps for RNA-seq data were generated with pheatmap using z-scores calculated from log count-per-million values obtained with the 'cpm' function in EdgeR (Robinson, M. D., et al. Bioinformatics 2010 26:139-140).

Western Blot Analyses: Western blots from all studies were performed on gastrocnemius muscle from representative animals lysed by Nonidet P-40 isotonic lysis buffer [50 mM Tris-HCl, pH 7.5, 120 mM NaCl, 1% (v/v) Nonidet P-40, 1 mM EDTA, 50 mM NaF, 40 mM glycerophosphate, and 1 g/ml each of protease inhibitors (aprotinin, pepstatin, and leupeptin)]. Equivalent amounts of protein from each sample, as determined by Bradford assay (Bio-Rad), was resolved by SDS-PAGE and then transferred (semi-dry) onto immobilon-nitrocellulose membranes (Millipore, Billerica, MA). Membranes were washed twice with TBST [Tris-buffered saline (TBS) containing 0.1% Tween 20], blocked with 5% nonfat milk in TBST for 1 hour, and then washed an additional 3 times. Membranes were incubated with specific primary antibody in TBST (1:1000) at 4° C. overnight, washed 3 times (TBST) and then incubated with appropriate goat anti-rabbit or anti-mouse IgG-horseradish peroxidase conjugates secondary antibodies (1:5000) at room temperature (1 hour). Following additional washes (TBST), immunoblots were visualized by ECL chemiluminescence (Amersham Biosciences, Little Chalfont, United Kingdom). Primary antibodies: phospho-STAT3 (Tyr705) (D3A7) XP® Rabbit mAb #9145, STAT3 (124H6) Mouse mAb #9139, (Cell Signaling Technology, Danvers, MA); a-tubulin (B-7), sc-5286, (Santa Cruz Biotechnologies, Santa Cruz, CA); androgen receptor (EP670Y), ab52615 (Abcam, Cambridge, MA) and GAPDH (6C5), sc-32233 (Santa Cruz Biotechnologies, Santa Cruz, CA).

Phospho-STAT3/STAT3 Analysis: Expression of phospho-STAT3 and total STAT3 in C-26 tumor tissues was measured using commercial sandwich ELISA kits according to the manufacturer's instructions (PathScan® Phospho-Stat3, #7300, and Total Stat3, #7305, Cell Signaling Technology, Danvers, MA).

Results

Figure 1A:
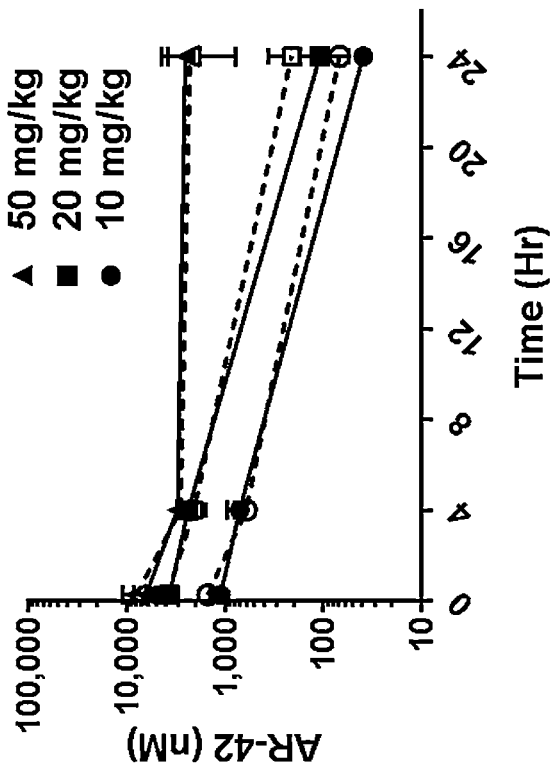
FIG. 1A is a graph showing results of a single dose AR-42 plasma and tissue pharmacokinetic study. Tumor-free 057BL/6 mice were administered a single dose of mg/kg, 20 mg/kg or 50 mg/kg AR-42 (n=3) and plasma (dashed) and gastrocnemius (solid) tissue analyzed for AR-42 content at different times using LC-MS/MS analyses according to Materials and Methods (Mean±SD).
Figures 1C, 1D:
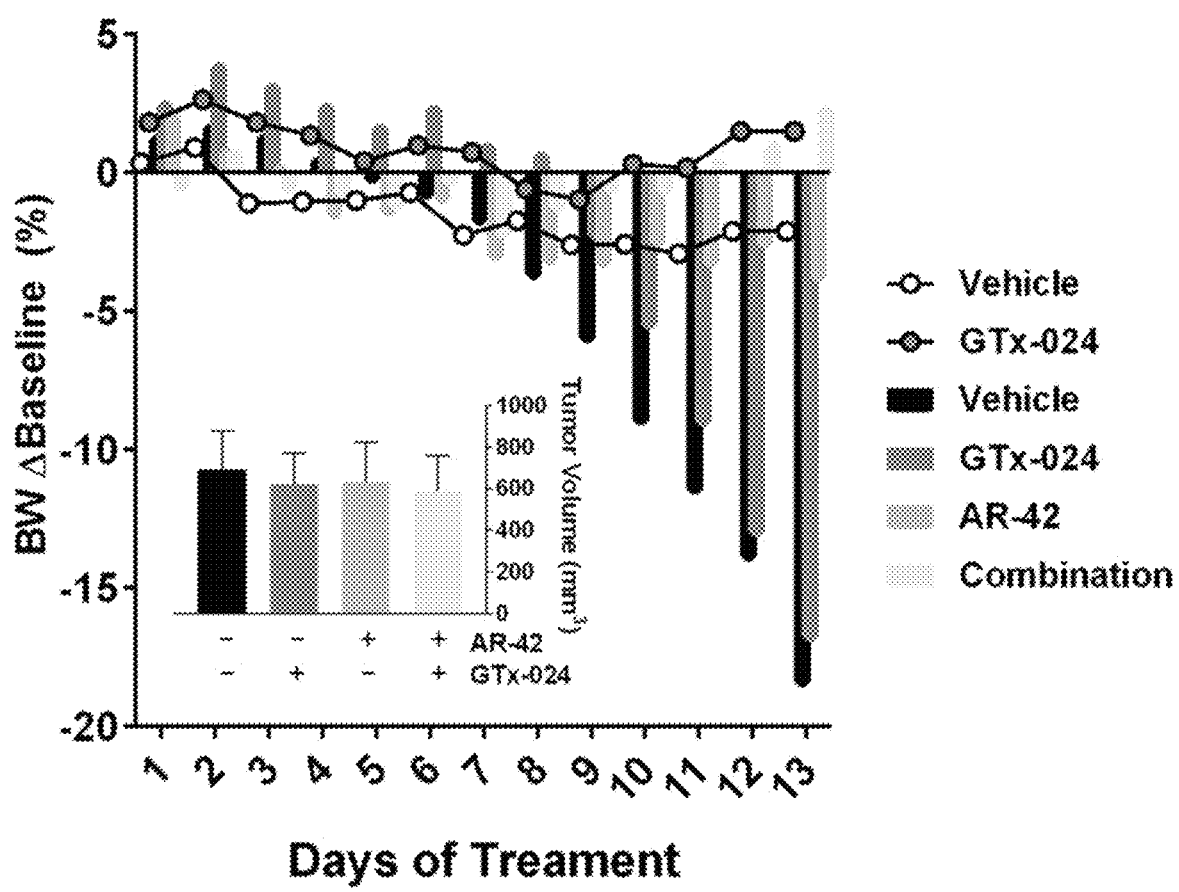
FIG. 1C is a table showing AR-42's in vitro human HDAC inhibition profile determined using recombinant enzymatic assays.
FIG. 1D shows results of Study 1, where animals receiving GTx-024 (15 mg/kg), AR-42 (10 mg/kg), Combination (15 mg/kg GTx-024 and 10 mg/kg AR-42) or Vehicle were treated daily by oral gavage for 13 days starting 6 days post-injection of C-26 cells. Longitudinal mean bodyweights per treatment group are presented as a percent change from pre-study body weights. Tumor-free animals (circles), tumor-bearing animals (bars). Inset: terminal tumor volumes (mean+SD, n=5-6 per group).

AR-42 Administration Demonstrates Anti-Cachectic Effects at a Reduced 10 Mg/Kg Dose Level The anti-cachectic effects of AR-42 (50 mg/kg via oral gavage every other day) were characterized in C-26 tumor-bearing mice (Tseng Y C, et al. J Natl Cancer Inst. 2015 107(12):djv274). This dose represented the maximally tolerated dose in mice, which was used to observe its anti-tumor effects in different xenograft tumor models. To better understand the disposition of AR-42 following oral administration in mice, a limited pharmacokinetic study of single oral doses of 50, 20 and 10 mg/kg of AR-42 was performed (FIG. 1A). Plasma exposure following oral administration of 50 mg/kg was 74.3 µM*h (FIG. 7), which exceeded the well tolerated plasma exposure in humans of 8.5 µM*h by 8.7-fold (Sborov D W, et al. Leuk Lymphoma. 2017 58(10):2310-8). Consequently, the anti-cachectic effects of lower doses of AR-42 was evaluated in a dose-response study in the C-26 model. Similar to six total 50 mg/kg doses (administered q2d), thirteen daily oral doses of 20 or 10 mg/kg AR-42 reversed C-26 tumor-mediated reductions in tumor-corrected body weight (FIG. 1B). AR-42 readily distributed into gastrocnemius muscle tissue (FIG. 1A) and, at the lowest efficacious dose of 10 mg/kg, muscle concentrations remained above 700 nM for 4 hours consistent with the ability of AR-42 at this dose to inhibit Class I and IIb HDACs for a portion of the dosing interval in muscle tissue based on its in vitro HDAC inhibition profile (FIG. 1C). The plasma exposure resulting from the 10 mg/kg dose (10.9 µM*h, FIG. 7) compares more favorably to well-tolerated exposures in patients while providing anti-cachectic efficacy and was therefore utilized in subsequent combination studies.

Figure 2A:
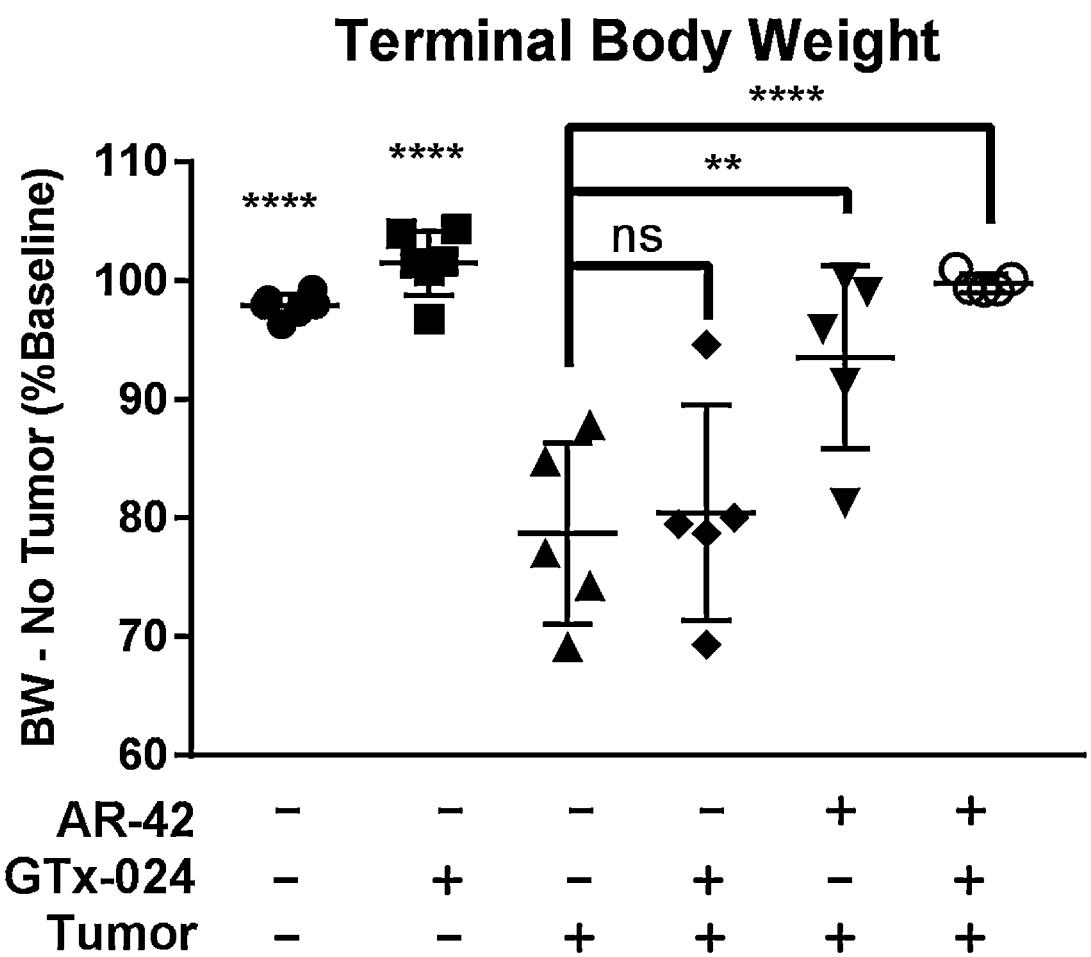
FIGS. 2A-2B show results of Study 1 where animals receiving GTx-024 (15 mg/kg), AR-42 (10 mg/kg), combination (15 mg/kg GTx-024 and 10 mg/kg AR-42) or vehicle were treated daily by oral gavage for 13 days starting 6 days post-injection of C-26 cells (n=5-6 per group).
Figure 2B:
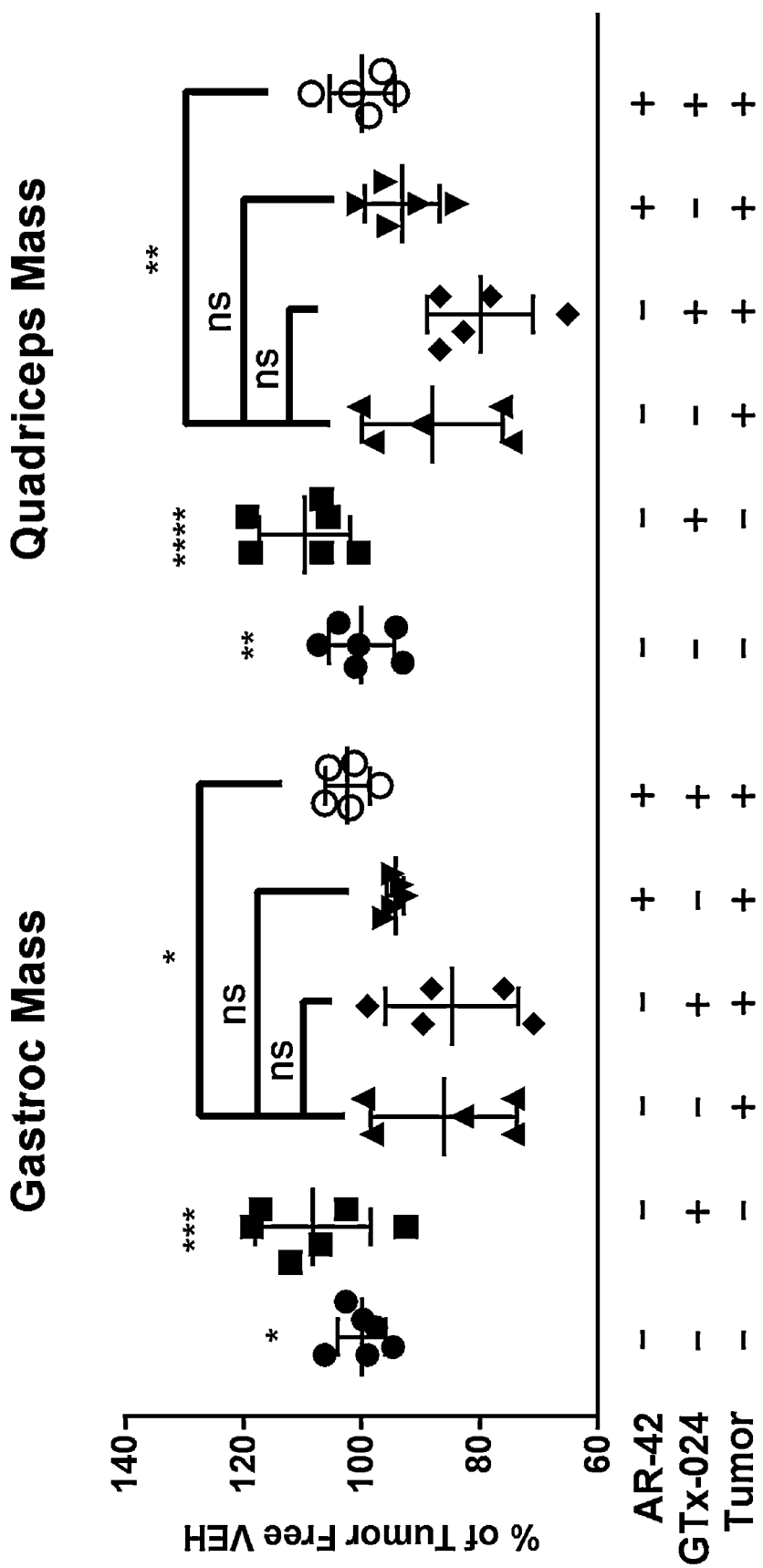
Figure 2C:
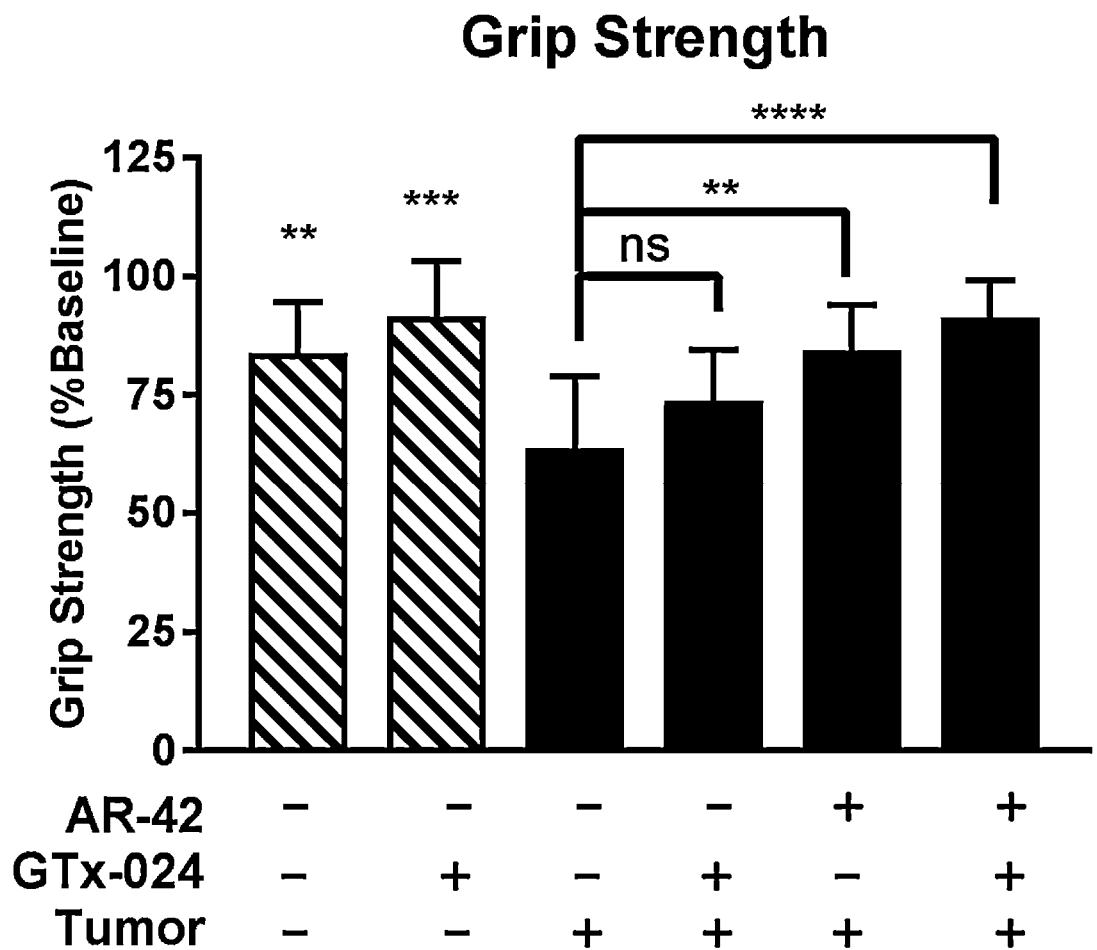
FIG. 2C is a bar graph showing day 16 grip strength per treatment group from Study 2 representing 5 repeat assessments per animal, (n=6-10 per group).
Figure 8B:
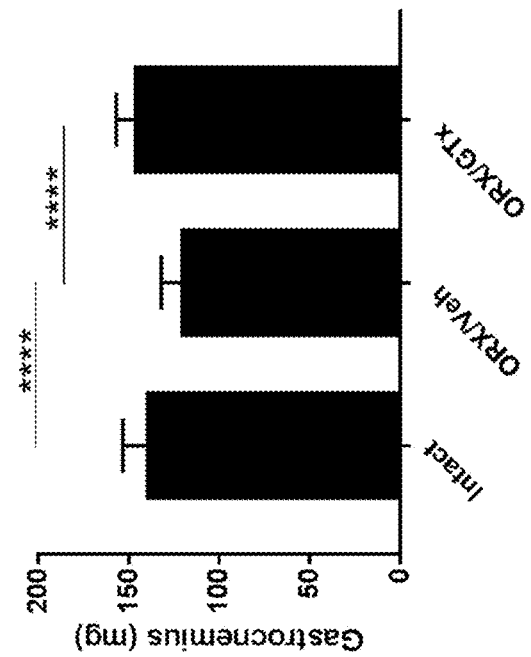
FIGS. 8A-8D are bar graphs showing the anabolic activity of GTx-024. Orchiectomized (ORX) male CD2F1 mice were treated with GTx-024 (GTx; 15 mg/kg; n=12) or vehicle (Veh; n=13) once daily by oral gavage for 28 days. Sham-orchiectomized (Intact) mice (n=14) were treated identically with vehicle.
Figure 8A:
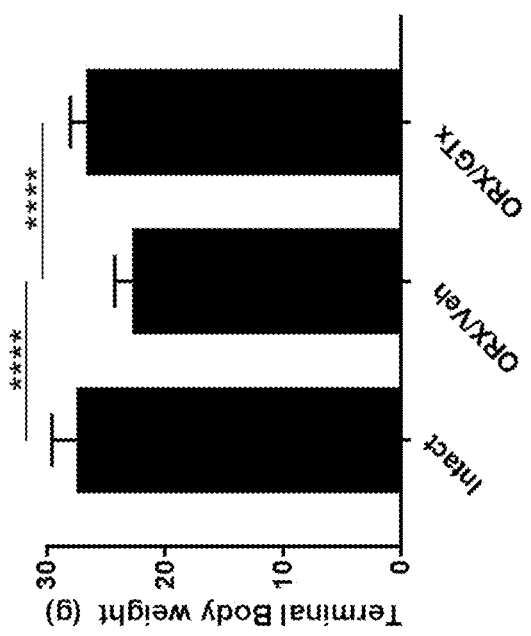
Figure 8C:
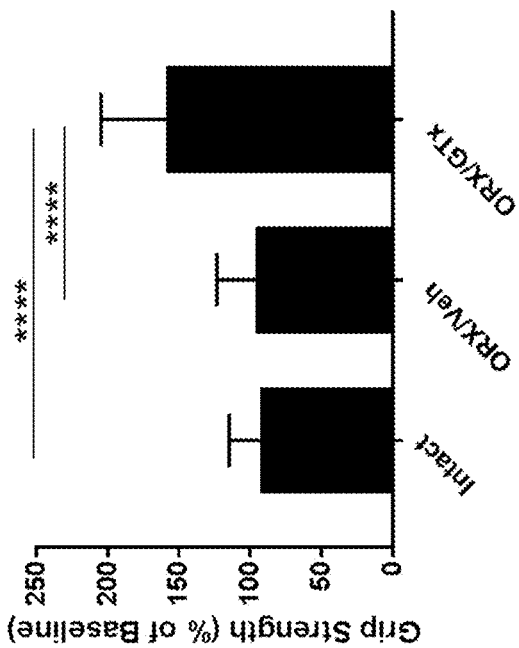
Figure 8D:
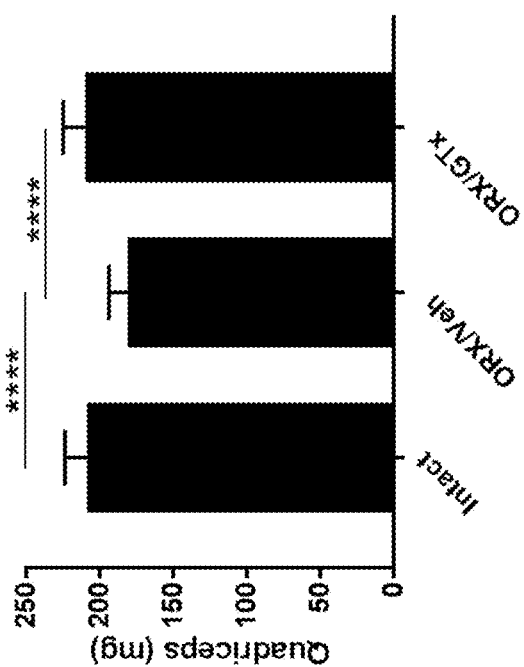
Figure 9A:
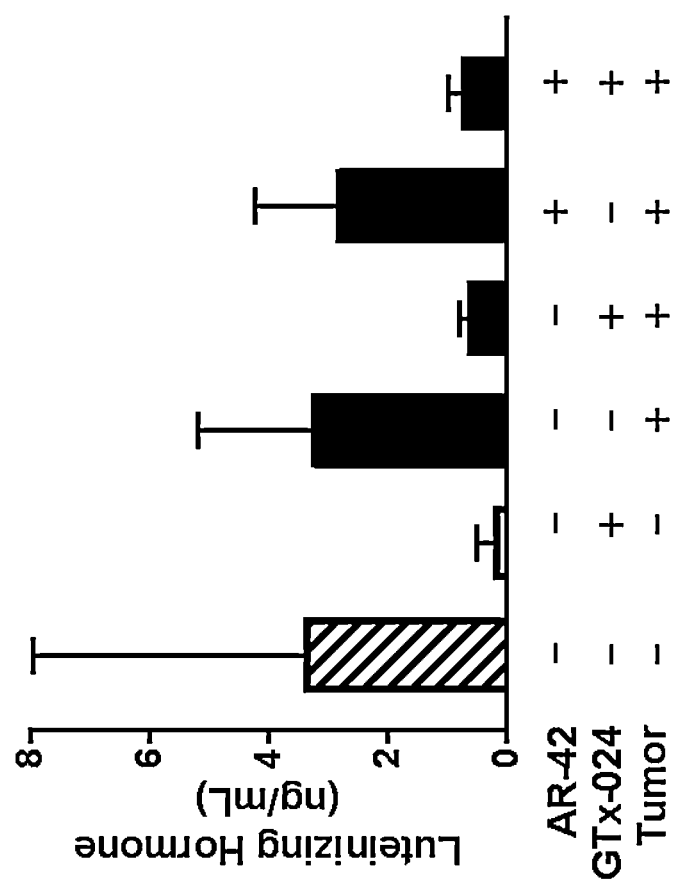
FIGS. 9A-9C show results of Study 1, where animals receiving GTx-024 (15 mg/kg), AR-42 (10 mg/kg), Combination (15 mg/kg GTx-024 and 10 mg/kg AR-42) or Vehicle were treated daily by oral gavage for 13 days starting 6 days post-injection of C-26 cells (n=5-6 per group).

Combination GTx-024 and AR-42 Administration Results in Improved Anti-Cachectic Efficacy To evaluate whether combining HDAC inhibition with SARM administration would improve anti-cachectic activity, a series of three studies combining AR-42 with androgen/SARM in the C-26 model were designed. In Study 1, vehicle-treated tumor-bearing animals lost approximately 20% of their body weight prior to meeting euthanasia criteria (FIG. 1D). This severe tumor-induced weight loss (FIG. 2A, of baseline) was accompanied by parallel reductions in gastrocnemius and quadriceps masses (FIG. 2B, 86±12.4 and 88±12.0%, relative to tumor-free controls, respectively). SARM monotherapy had no apparent anti-cachectic efficacy in C-26 tumor-bearing mice. GTx-024 at 15 mg/kg did not spare body weight (FIG. 1D, 2A) or the mass of gastrocnemius and quadriceps muscles (FIG. 2B). At this dose, GTx-024 was well tolerated in previously xenografted mice (Narayanan R, et al. PloS one. 2014 9(7):e103202) and, in this study, did not cause body weight loss in tumor-free controls (FIG. 1D, 2A). Furthermore, GTx-024 was reported to be fully anabolic at doses as low as 0.5 mg/kg/day in rodents (reported as S-22 in Kim J, et al. J Pharmacol Exp Ther. 2005 315(1):230-9) and compared favorably to the less potent structural analog S-23 (Jones A, et al. Endocrinology. 2009 150(1):385-95), which reversed orchiectomy- and glucocorticoid-mediated wasting (Jones A, et al. Endocrinology. 2010 151(8):3706-19). A separate control study in tumor free CDF1 mice confirmed that in our hands, 15 mg/kg GTx-024 was capable of increasing body-weight, gastrocnemius and quadriceps mass, and grip strength relative to orchiectomized (ORX) controls (FIG. 8). Importantly, GTx-024-mediated suppression of serum luteinizing hormone, a very well characterized pharmacological effect of potent androgen administration, demonstrates that GTx-024 administered to C-26 tumor bearing mice was active (FIG. 9A).

Consistent with the preliminary dose-response study, 10 mg/kg AR-42 alone significantly spared body weight (FIGS. 1D and 2A, 93.6±7.7% of baseline) relative to tumor-bearing vehicle treated controls. However, these changes were not translated into significant improvements in gastrocnemius and quadriceps mass (FIG. 2B). In contrast to monotherapy, C-26 tumor-bearing mice receiving both GTx-024 and AR-42 started to gain body weight relative to baseline after nearly two weeks of treatment, whereas all other treated tumor-bearing groups lost body weight (FIG. 1D). This combination exhibited a striking ability to consistently protect body weight (99.9±0.8% of baseline, corrected for tumor weight) relative to either agent alone (FIG. 2A). Furthermore, the effects of combined therapy completely spared gastrocnemius (102.4±3.8%) and quadriceps (99.9±5.5%) mass relative to tumor-free controls (FIG. 2B).

Figure 9B:
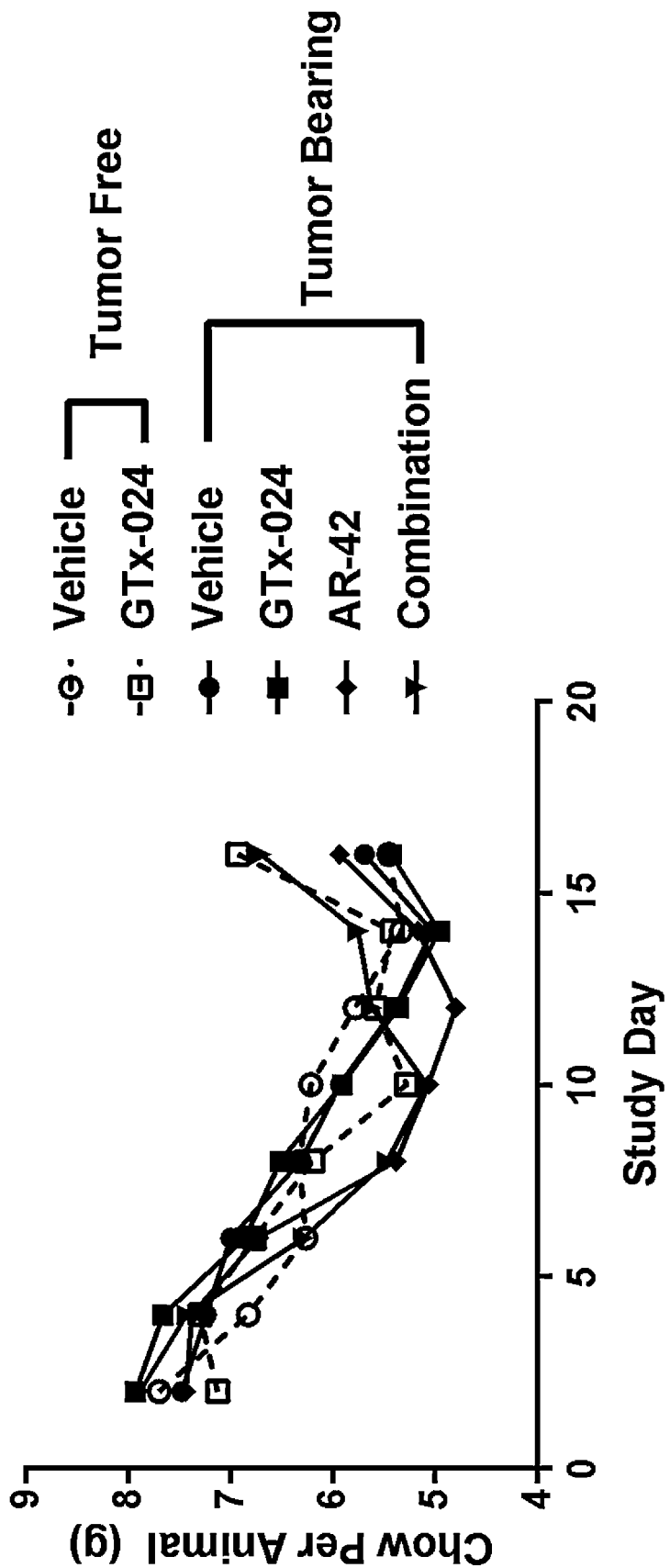

The effects of combined therapy on total body weight or amelioration of cachectic symptoms were not due to any overt impact on tumor burden as no significant differences in tumor volumes were apparent at the end of the study (FIG. 1D, inset). Food consumption was monitored to account for potential anti-anorexic effects of treatment on the cachectic sequela following C-26 cell inoculation. GTx-024-treated tumor-free control animals, as well as the combination-treated group, demonstrated small increases in per animal food consumption relative to other groups between day 14 and 16 (FIG. 9B), which are unlikely to account for differences in body weight apparent by study day 14 (treatment day 9), as well as end of study differences in skeletal muscle masses (FIG. 2B).

Figure 9C:
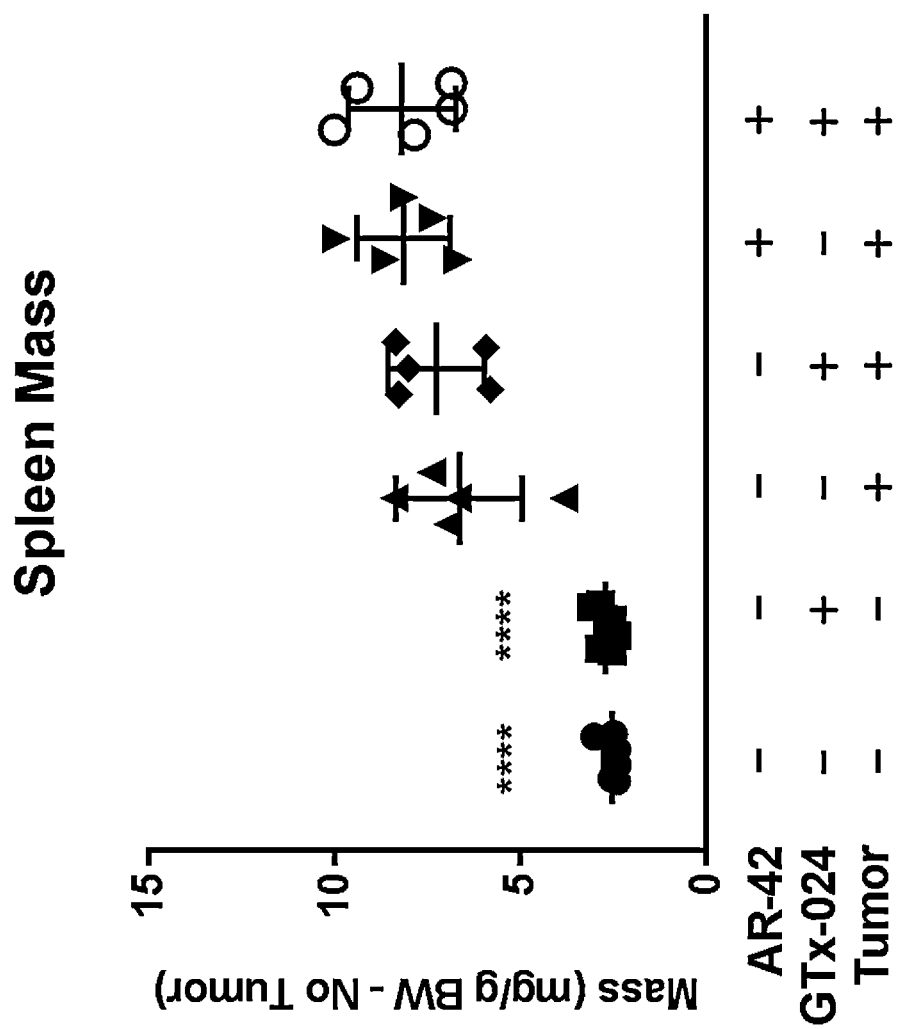
Figure 10A:
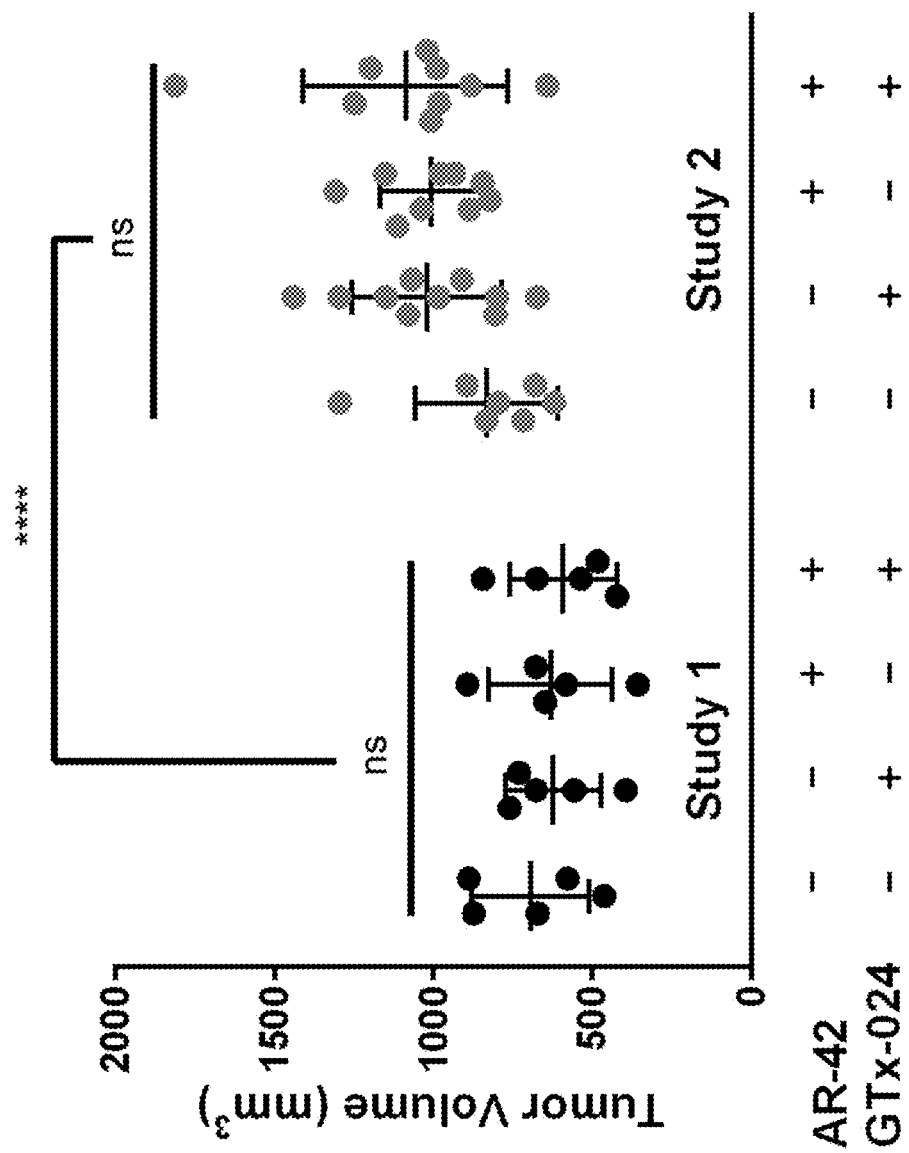
FIGS. 10A-10D show results of Study 2, wherein animals receiving GTx-024 (15 mg/kg), AR-42 (10 mg/kg), Combination (15 mg/kg GTx-024 and 10 mg/kg AR-42) or Vehicle were treated daily by oral gavage for 12 days starting 6 days post-injection of C-26 cells (n=6-10 per group).
Figure 10B:
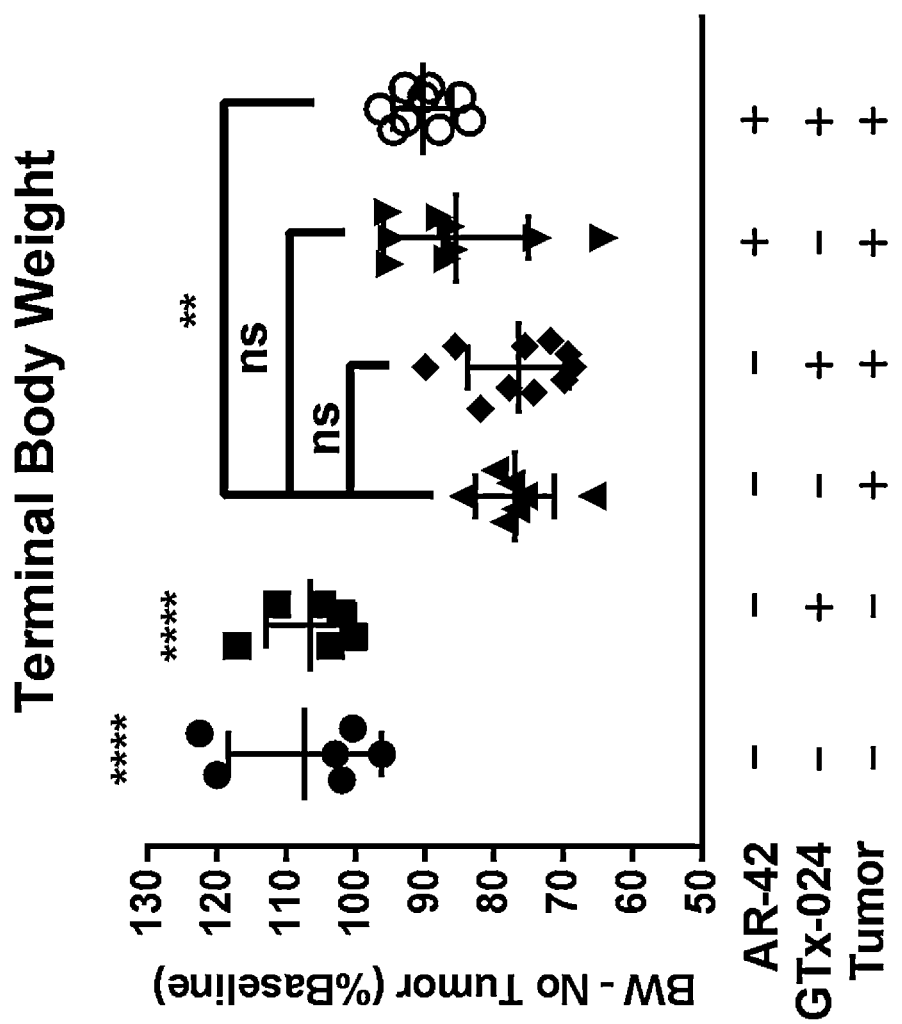
Figure 10C:
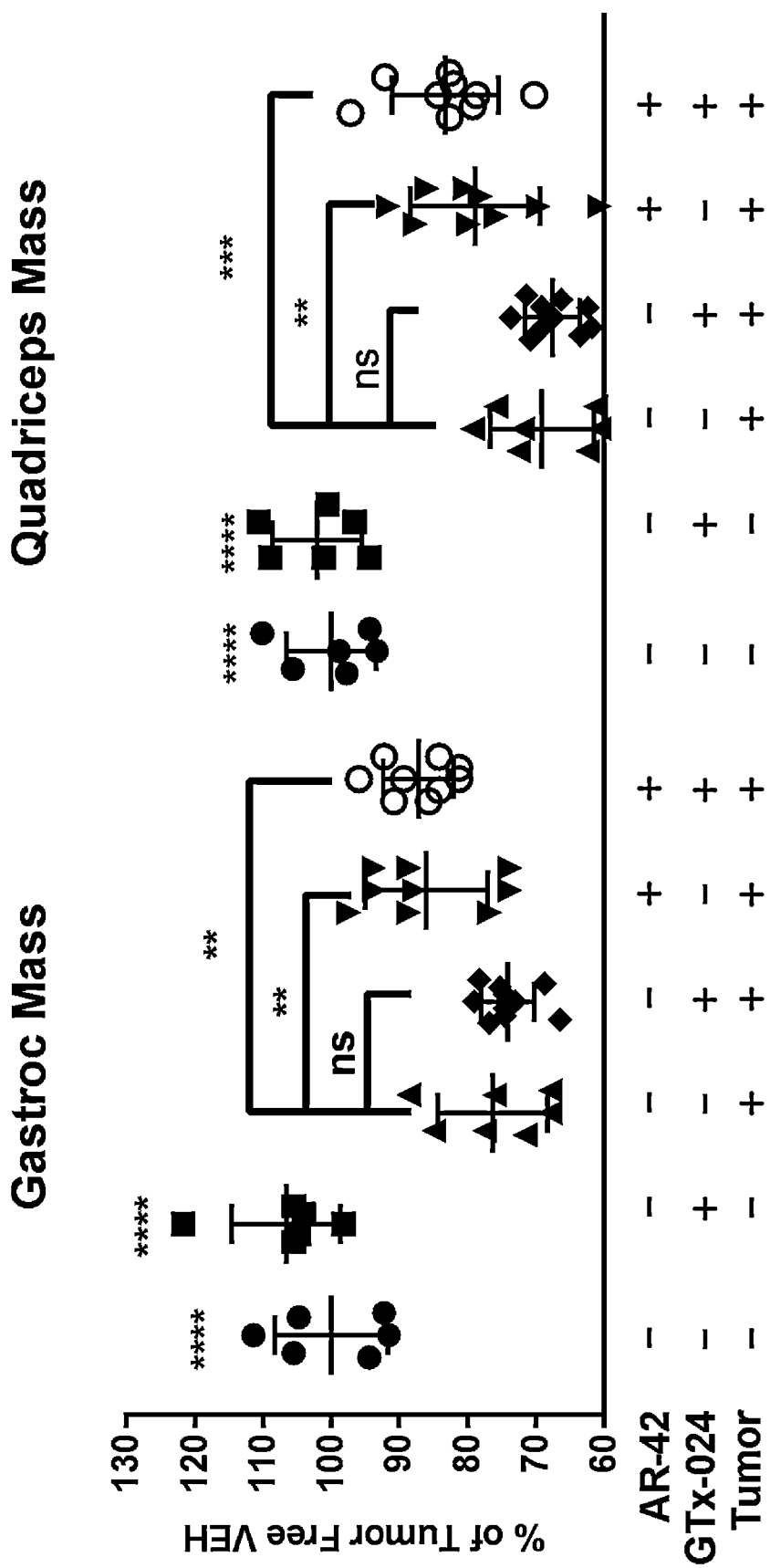
Figure 10D:
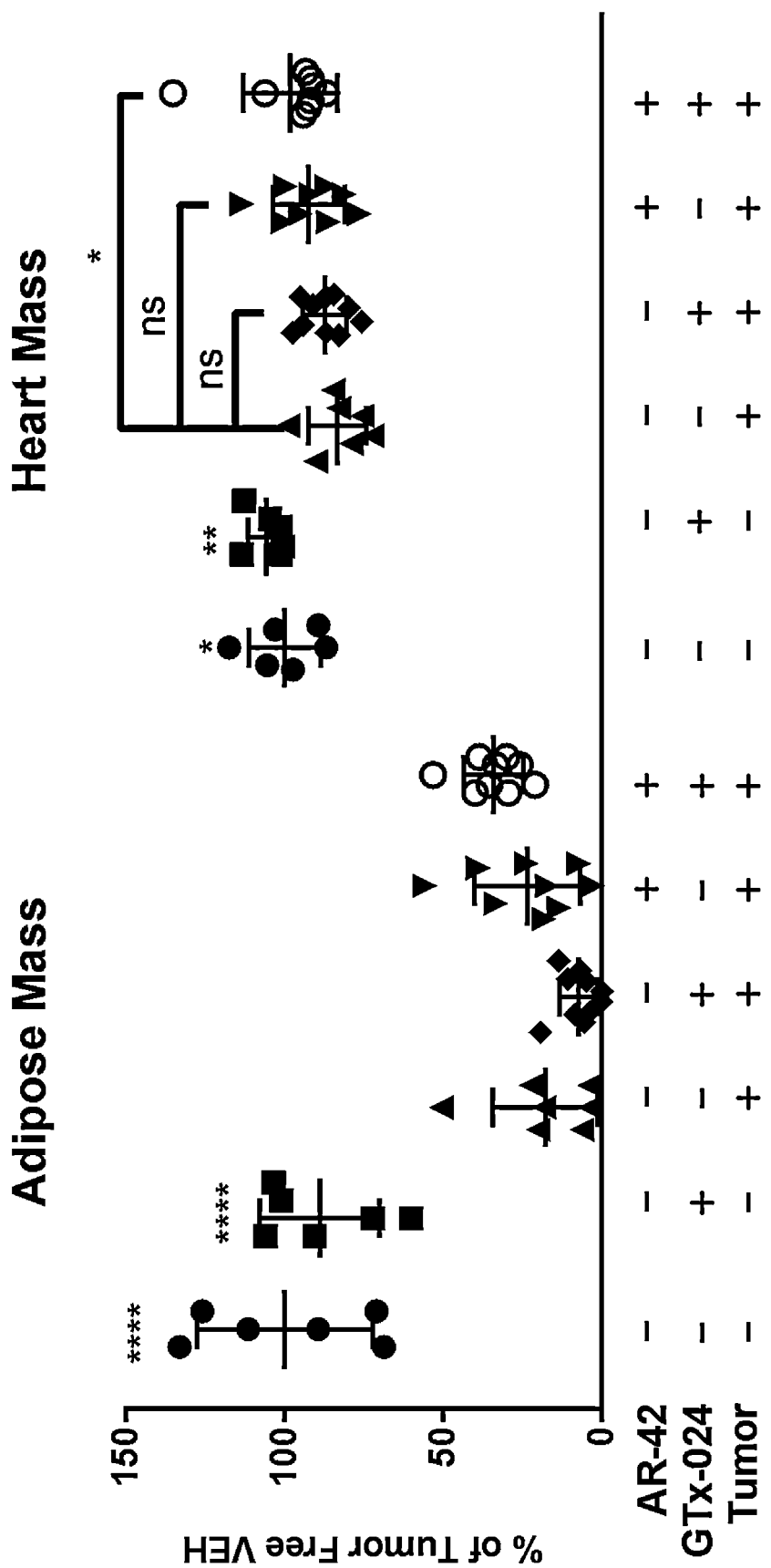

These promising results prompted a repeat of the experiment with expanded animal numbers and the use of forelimb grip dynamometry as a measure of muscle function. In this confirmatory study (Study 2), the model was more aggressive resulting from significantly larger tumors relative to Study 1, though no differences within treatment groups were apparent (FIG. 10A). As a result, the study was terminated early, after only 12 days of treatment. In accordance with this increased tumor burden, tumor-corrected body weights were more consistently reduced and to a larger degree in tumor-bearing controls ($77.0\pm5.7\%$ and $80.4\pm9.1\%$ of baseline in the second and first studies, respectively; FIG. 10B), and larger losses in gastrocnemius ($76.3\pm8.1\%$) and quadriceps ($69.1\pm7.6\%$) mass relative to tumor-free controls were noted (FIG. 10C). In the face of this more severe cachexia, only combined AR-42 and GTx-024 administration significantly spared body weight ($90.3\pm4.3$ of baseline), though not to the degree realized in the first study (FIG. 10B vs FIG. 2A), while both AR-42 alone and the combination significantly spared gastrocnemius and quadriceps mass (FIG. 9C). C-26 tumors were accompanied by large reductions in forelimb grip strength (FIG. 4C, $63.8\pm15.3\%$ versus $83.8\pm10.7\%$ of baseline in tumor-bearing and tumor-free controls, respectively), but, consistent with the improvements in hind limb skeletal muscle mass, AR-42 alone and in combination with GTx-024 improved grip strength over vehicle-treated tumor-bearing controls. Unlike the adipose-sparing effect of the higher 50 mg/kg dose of AR-42 (Tseng Y C, et al. J Natl Cancer Inst. 2015 107(12):djv274), the lower dose of mg/kg had no impact on adipose or heart mass (FIG. 10D). As androgens are thought to actively prevent adipogenesis (Singh R, et al. Endocrinology. 2003 144(11): 5081-8), SARM administration was not expected to protect against C-26 tumor-mediated fat losses. Indeed, no treatment mediated effects on abdominal adipose were apparent (FIG. 10D). The data show heart mass was significantly improved by combination therapy, but this result is likely due to the effects of a single outlier animal.

Multiple Androgens Demonstrate Improved Anti-Cachectic Efficacy when Combined with AR-42

Figure 2D:
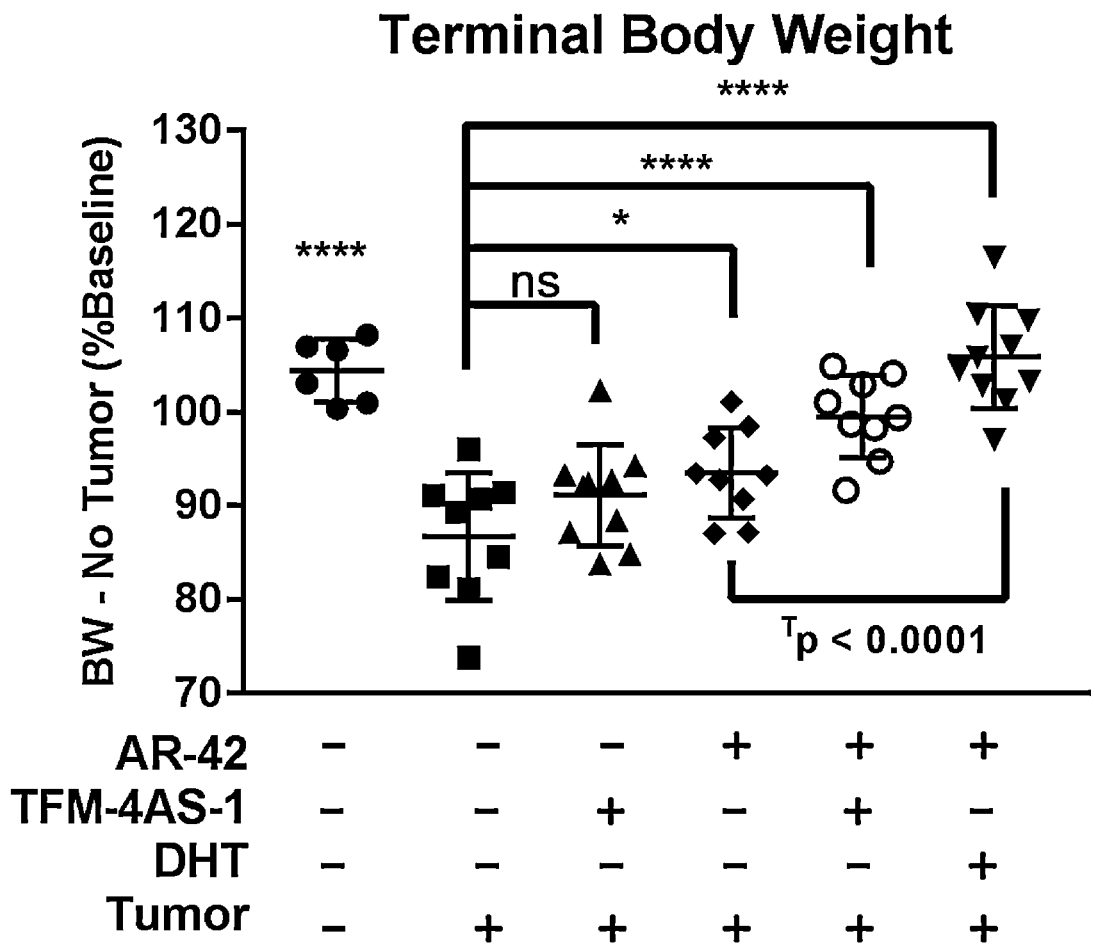
FIGS. 2D-2F show results from Study 3, where animals receiving AR-42 (10 mg/kg, oral gavage), TFM-4AS-1 (10 mg/kg, subcutaneous), Combination AR-42 and DHT (10 mg/kg oral gavage and 3 mg/kg subcutaneous, respectively), Combination AR-42 and TFM-4AS-1 (10 mg/kg, both) or Vehicle were treated daily for 12 days starting 6 days after cell injection (6-per group).
Figure 2E:
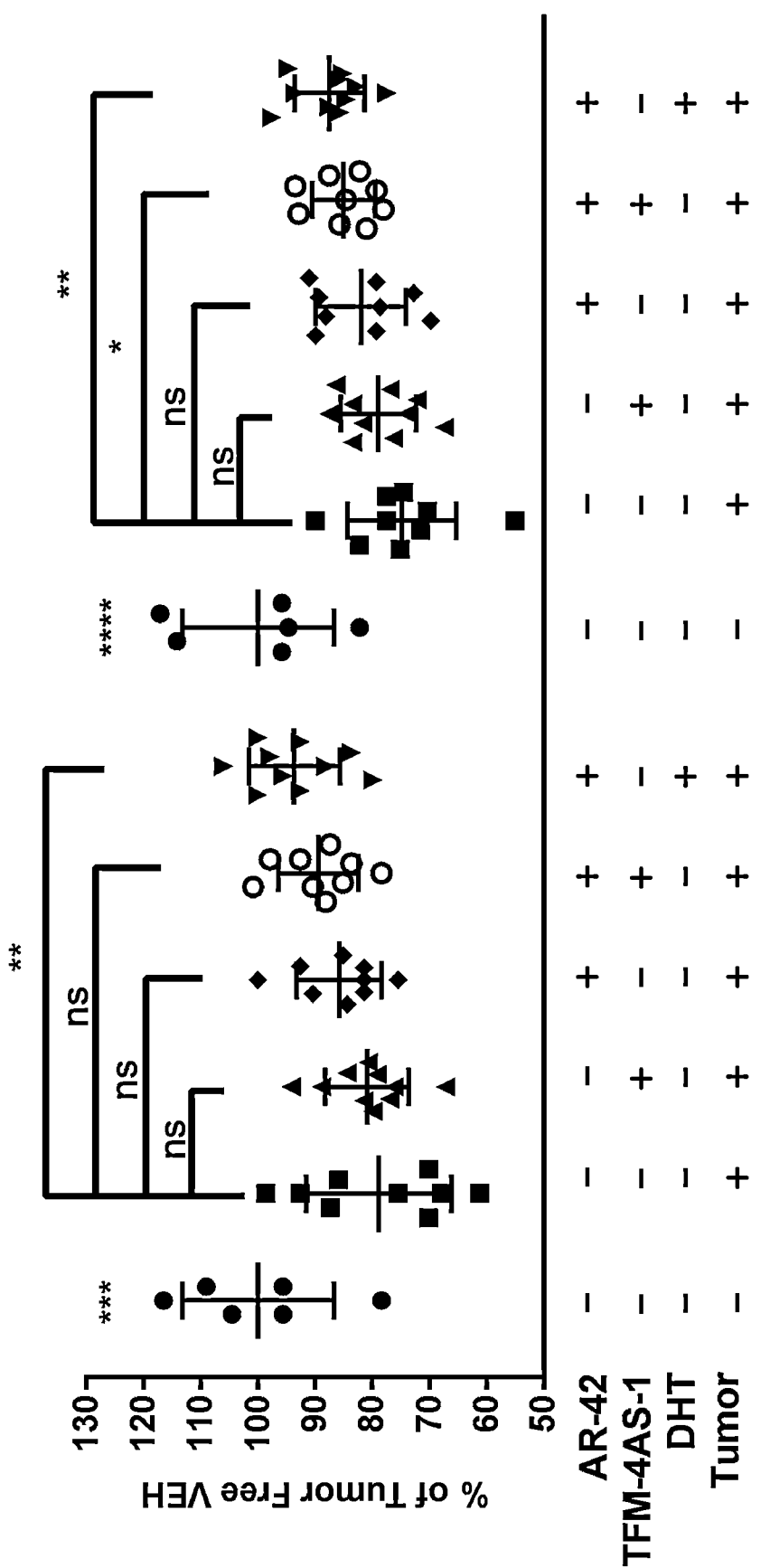

To confirm that the improvement of GTx-024's anti-cachectic efficacy in the C-26 model by co-administration with AR-42 was not a drug-specific phenomenon, tumor-bearing animals were treated with the SARM TFM-4AS-1 (Schmidt A, et al. J Biol Chem. 2010 285(22):17054-64) and the potent endogenous androgen DHT alone and in combination with AR-42 (Study 3). Similar to the 15 mg/kg dose of GTx-024, TFM-4AS-1 was administered at a previously characterized fully anabolic dose (10 mg/kg), but, as a monotherapy, did not spare body weight (FIG. 2D) or mass of gastrocnemius or quadriceps (FIG. 2E).

Figure 11A:
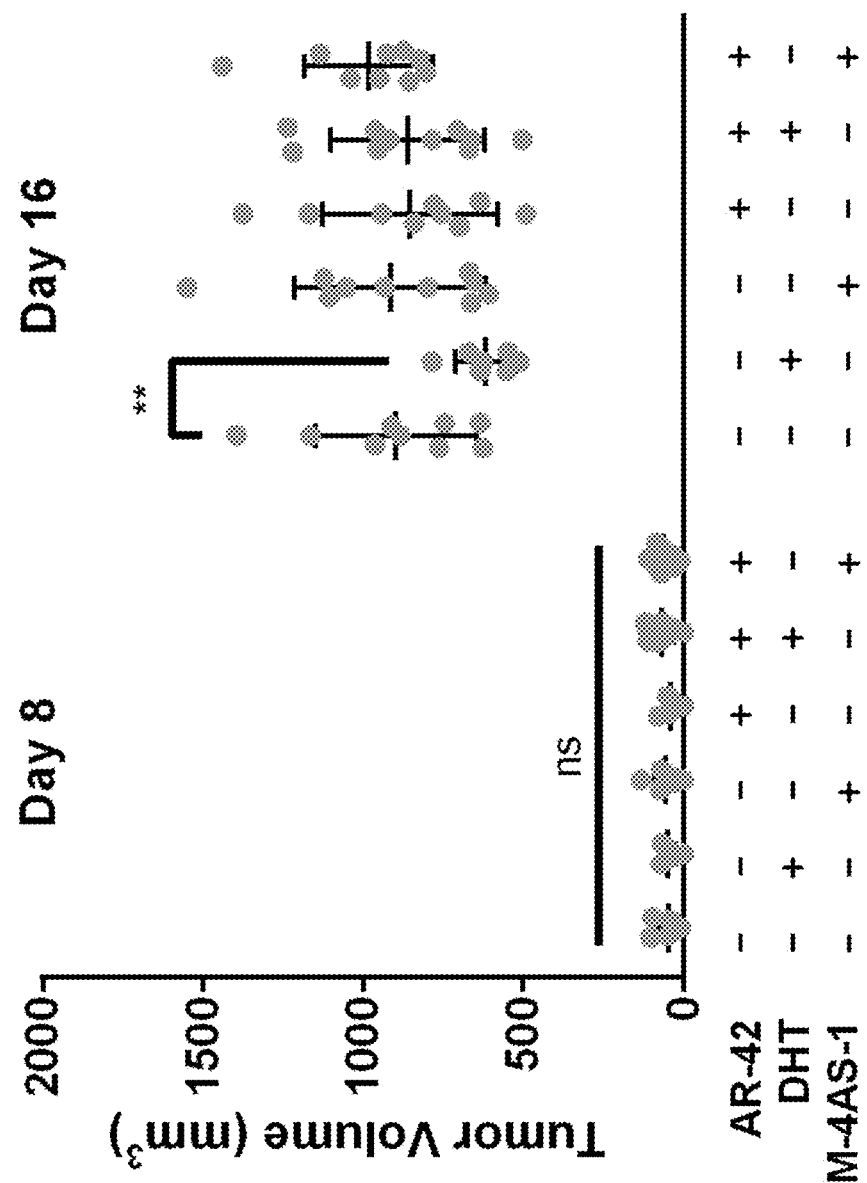
FIGS. 11A-11B show results of Study 3, where animals receiving AR-42 (10 mg/kg, oral gavage), TFM-4AS-1 (10 mg/kg, subcutaneous injection), Combination AR-42 and DHT (10 mg/kg oral gavage and 3 mg/kg subcutaneous injection, respectively), Combination AR-42 and TFM-4AS-1 (10 mg/kg, both) or Vehicle were treated daily for 12 days starting 6 days post-injection of C-26 cells.
Figure 11B:
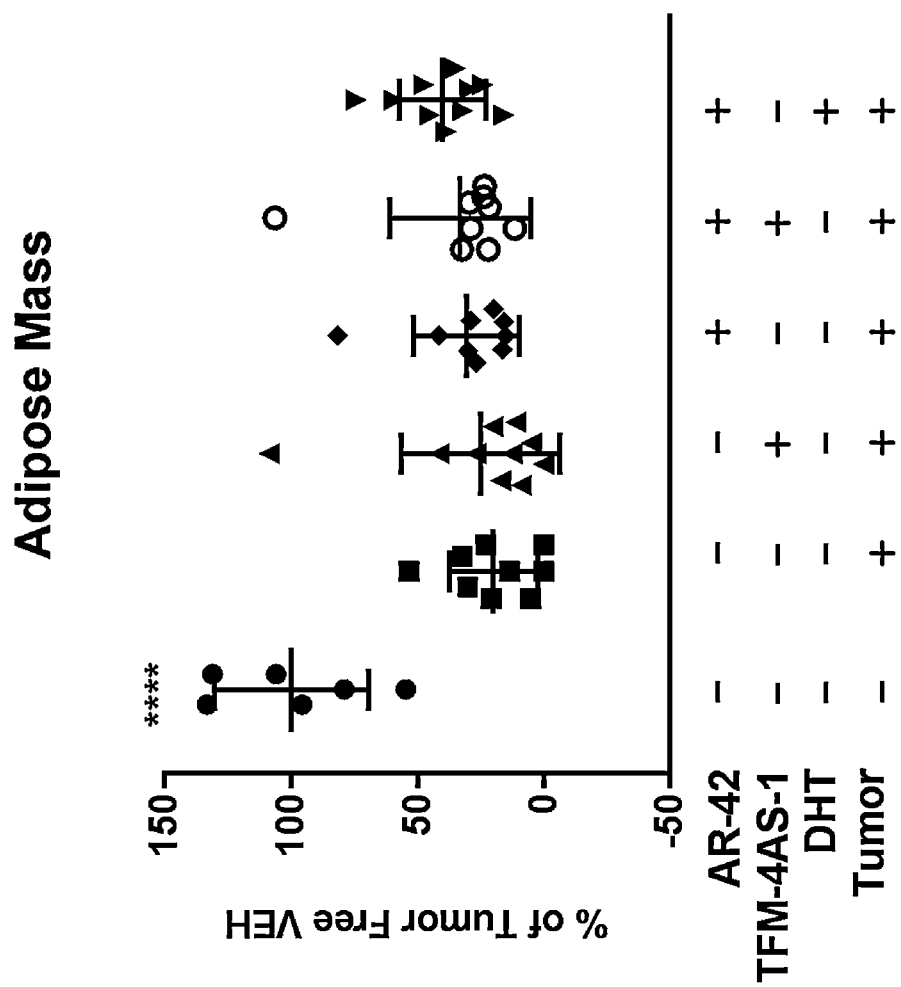

AR-42 alone resulted in significant attenuation of body weight loss ($93.5\pm4.8$ of baseline), but was less effective than in combination with TFM-4AS-1 ($99.5\pm4.4$ of baseline) or DHT ($106.0\pm5.4$ of baseline). The DHT/AR-42 combination significantly improved bodyweights ($p<0.0001$) compared to AR-42 treatment alone (FIG. 2D). Of note, tumor-bearing animals treated with DHT alone did not differ in initial tumor volumes (Day 8), but after 8 days of DHT administration, tumor growth was significantly suppressed resulting in the exclusion of DHT alone treated animals from further analyses (FIG. 11A). Consistent with both Studies 1 and 2, improvements in body weight were not due to sparing adipose tissue as no treatment-mediated effects on adipose were apparent (FIG. 11B).

Figure 2F:
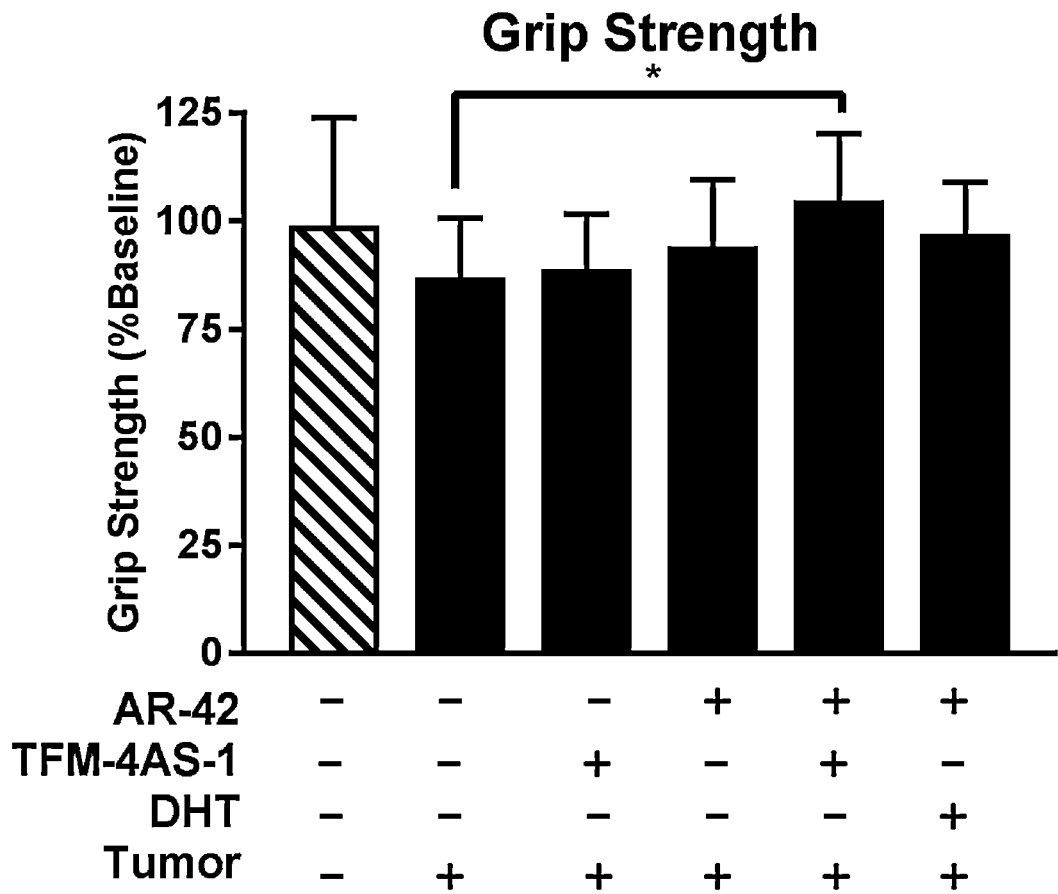

Similar to the first study, AR-42 monotherapy did not significantly impact skeletal muscle masses despite positive effects on body weight. However, combination treatment-mediated improvements in body weight were again translated to increased skeletal muscle masses where DHT/AR-42 combination significantly spared both gastrocnemius and quadriceps mass ($93.7\pm8.0$ and $87.5\pm6.1\%$ versus tumor-free controls, respectively), while the TFM-4AS-1/AR-42 combination attenuated atrophy of the quadriceps only ($85\pm5.5\%$ of tumor-free controls, FIG. 2E). Congruent with the lesser impact of the C-26 tumors on lower limb skeletal muscle mass in Study 3, smaller deficits in grip strength were apparent in tumor-bearing controls relative to Study 2 (86.5% and 63.8% of baseline, respectively; FIG. 2F vs 2C). The only treatment resulting in significantly improved grip strength was the combination of TFM-4AS-1 and AR-42, which increased muscle function over baseline (104.2%) despite the presence of C-26 tumors.

Figure 3A:
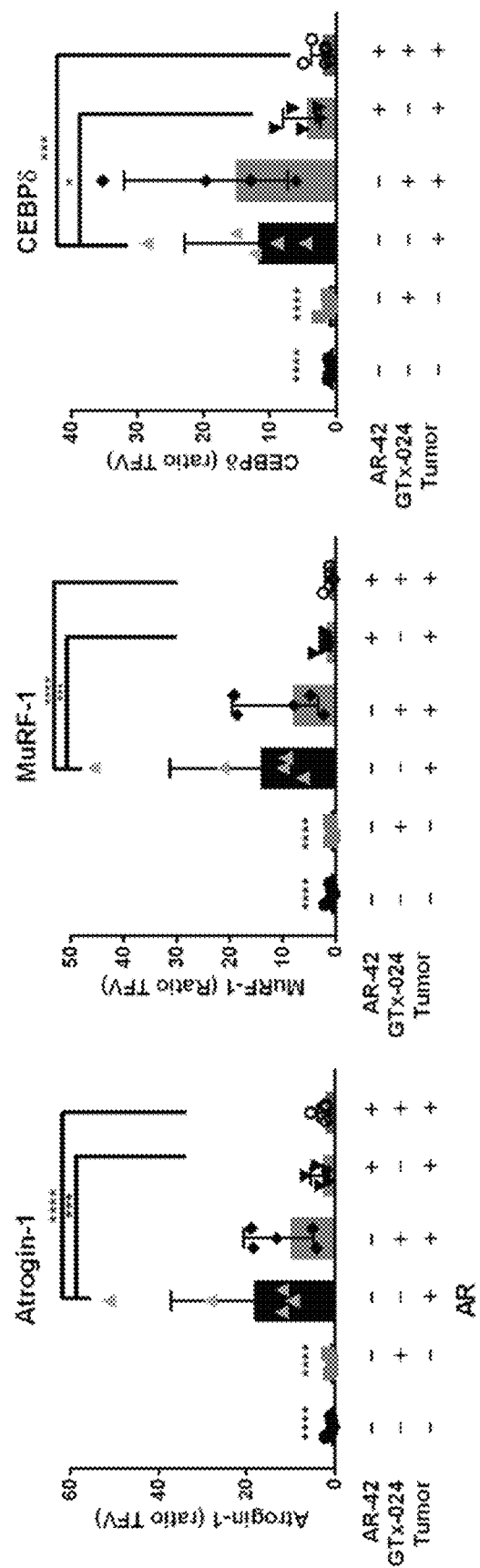
FIGS. 3A-B show gene expression of multiple cachexia-associated markers in gastrocnemius muscles of individual animals from Study 1 (n=5-6 per group). Expression was determined by qRT-PCR (Geometric Mean±Geometric STD).

Effects of Tumor Burden and GTx-024/AR-42 Treatment on the Expression of AR and Atrophy-Related Genes in Skeletal Muscle Candidate gene expression analyses were performed on gastrocnemius tissue from Study 1 to characterize the effects of C-26 tumors and treatment with GTx-024, AR-42 or both agents on genes whose function has been previously associated with C-26 tumor-mediated wasting (FIG. 3A). As expected for this model, the muscle-specific E3 ligases atrogin-1 (FBXO32) and MuRF-1(TRIM63) were induced in skeletal muscles of tumor-bearing animals (Tseng Y C, et al. J Natl Cancer Inst. 2015 107(12):djv274; Bonetto A, et al. PloS one. 2011 6(7):e22538) as was the STAT3 target gene and regulator of atrogin-1 and MuRF-1, CEBPδ (CEBPD) (Silva K A, et al. J Biol Chem. 2015 290(17):11177-87). Consistent with the absence of any anti-cachectic effects of GTx-024 monotherapy, this treatment had no significant impact on atrogin-1, MuRF-1, or CEBPδ expression. Ten mg/kg AR-42 alone and in combination with GTx-024 significantly reduced the expression of each atrogene relative to tumor-bearing controls, returning them to near baseline levels. AR-42's effects on E3 ligase expression were consistent with results from animals receiving the higher dose of 50 mg/kg (Tseng Y C, et al. J Natl Cancer Inst. 2015 107(12):djv274) further supporting the importance of AR-42's ability to reverse induction of these key enzymes to its overall anti-cachectic efficacy.

A Potential Contributor to Androgen Therapy Resistance

Figure 3B:
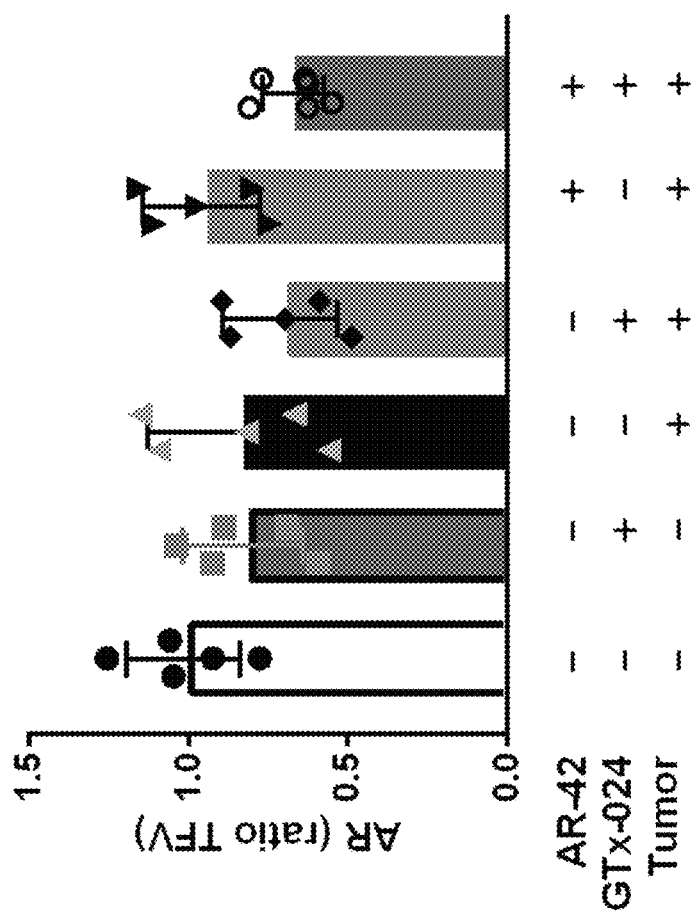
Figure 3C:
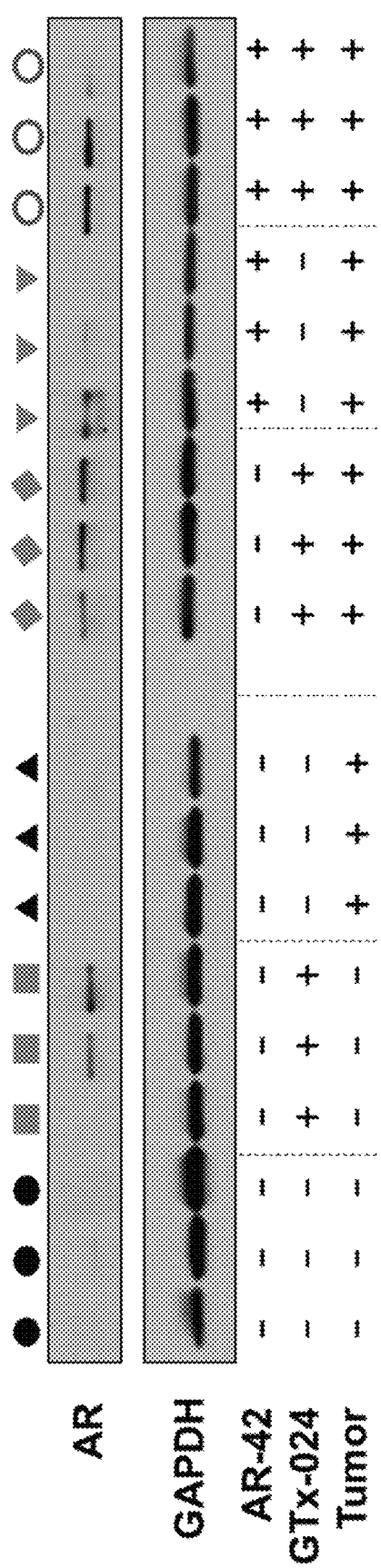
FIG. 3C shows western blot analysis of AR in gastrocnemius muscles from representative mice in Study 1. Statistics all panels: *p<0.05, *p<0.001, **p<0.0001 versus tumor-bearing vehicle-treated controls, Dunnett's multiple comparison test. CEBPδ, n=4, insufficient sample to analyze all tumor-bearing GTx-024-treated animals.

To determine the effect of tumor burden on androgen receptor (AR) levels in skeletal muscle, gastrocnemius AR levels were characterized. Neither tumor nor treatment had a significant impact on AR mRNA (FIG. 3B). AR protein expression in gastrocnemius was low in tumor-free controls and increased in response to GTx-024 administration irrespective of tumor burden (FIG. 3C) consistent with androgen agonist binding and stabilization of the AR (Kemppainen J A, et al. J Biol Chem. 1992 267(2):968-74). In contrast, AR-42 treatment did not have a marked impact on AR expression.

Figure 12A:
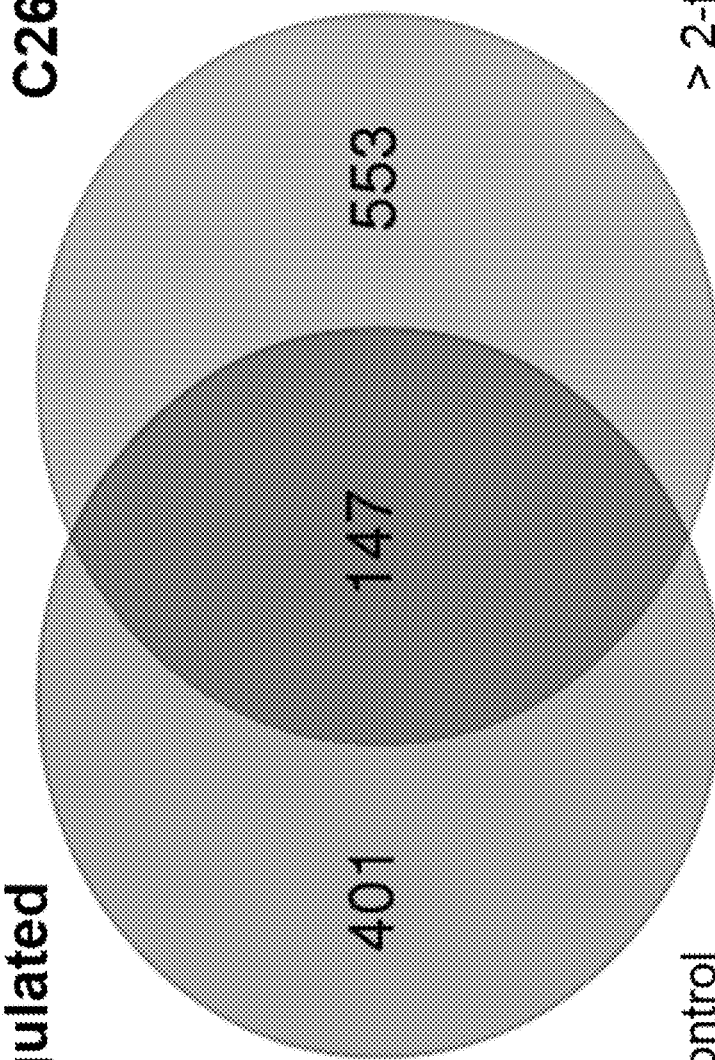
FIG. 12A shows genes differentially regulated in gastrocnemius muscle by 50 mg/kg AR-42 treatment relative to C-26 tumor-bearing vehicle-treated controls from Tseng et al. (Tseng Y C, et al. J Natl Cancer Inst. 2015 107(12): djv274) intersected with genes differentially regulated in quadriceps muscle from both severe and moderately wasting C-26 tumor-bearing mice relative to tumor-free control from Bonetto et al. (Bonetto A, et al. PloS one. 2011 6(7):e22538).
Figure 12B:
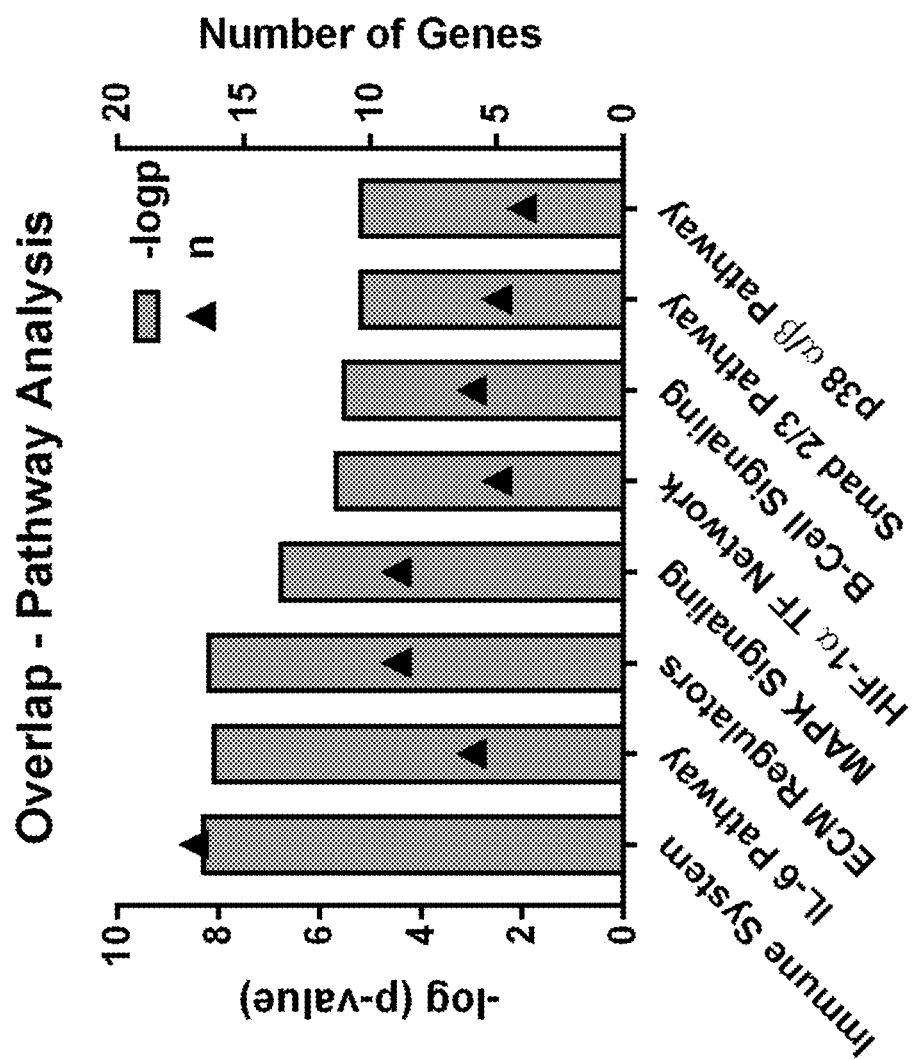
FIG. 12B is a bar graph sowing canonical pathway analysis using GSEA of 147 overlapping genes from FIG. 12A.

Anti-Cachectic Efficacy of AR-42 Associated with STAT3 Inhibition but not General Immune Suppression Previously reported ingenuity pathway analyses of AR-42-regulated genes in gastrocnemius muscle revealed that 66 genes associated with muscle disease or function were significantly regulated by AR-42 relative to C-26 tumor-bearing vehicle-treated controls (Tseng Y C, et al. J Natl Cancer Inst. 2015 107(12):djv274). In an effort to enrich previously reported differentially regulated genes (n=548) for transcripts critical to the anti-cachectic efficacy of AR-42, these data were intersected with previously published differentially regulated genes from the quadriceps of moderate and severely wasted C-26 tumor-bearing mice (Bonetto A, et al. PloS one. 2011 6(7):e22538) (n=700, FIG. 12A). Using this approach, the likely biological relevance of the 147 overlapping genes is increased when it is considered that these transcripts represent genes regulated by AR-42 that are associated with C-26-induced wasting from two different muscles (gastrocnemius and quadriceps), detected by two different technologies (RNA-seq and microarray) and reported by two different research laboratories. Pathway analyses performed on this pool of 147 genes revealed IL-6 signaling and immune system pathways, along with other gene sets regulated subsequent to cytokine stimulation, implicating AR-42's effects on cytokine and immune signaling in its anti-cachectic efficacy (FIG. 12B).

Figure 4C:
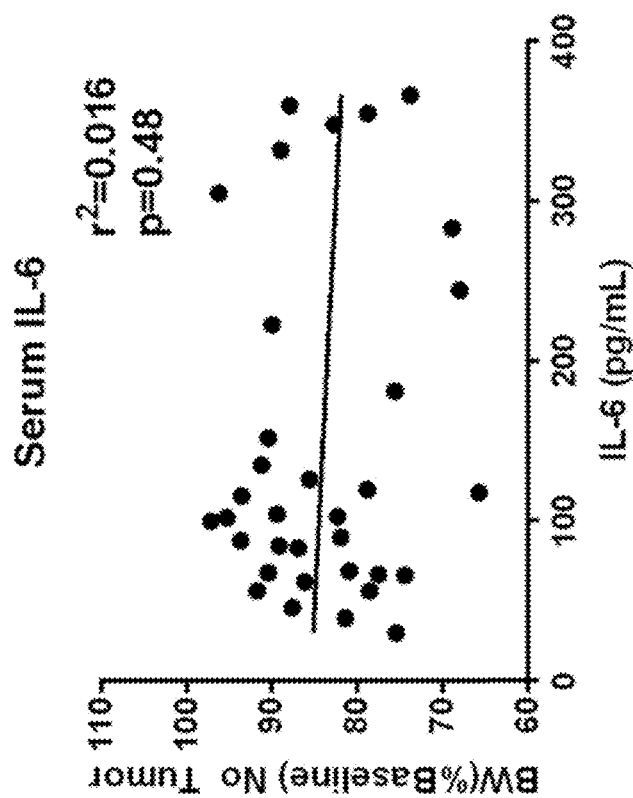
FIG. 4C is a plot showing individual animal serum IL-6 values as determined in A plotted against tumor-corrected terminal bodyweights from Study 2 (Pearson's Correlation).
Figure 4B:
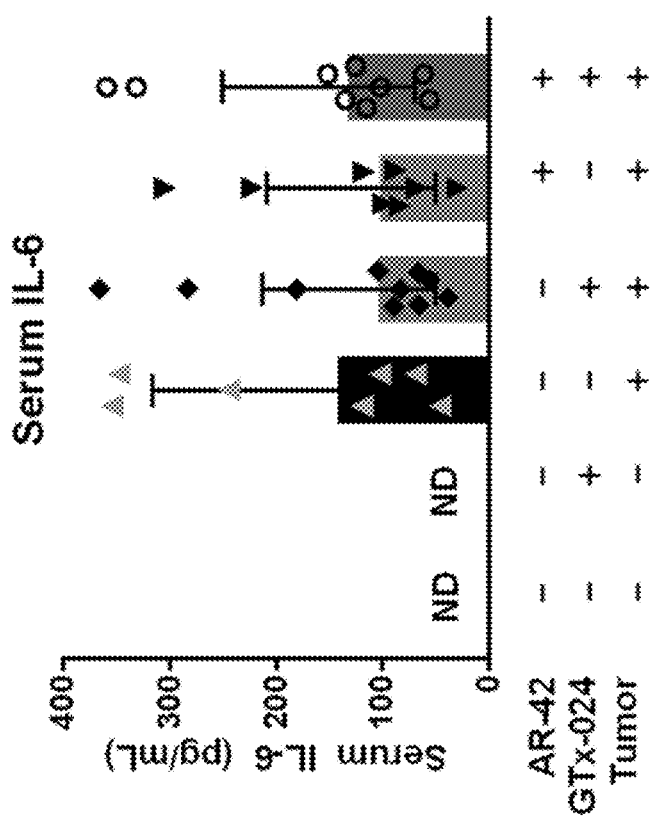
FIG. 4B is a bar graph show in ELISA analysis of serum IL-6 levels in terminal samples from Study 2. ND, not detected.

In agreement with the present pathway analyses, the higher 50 mg/kg dose of AR-42 reduced serum IL-6 levels, as well as gastrocnemius IL-6 receptor mRNA abundance in tumor-bearing mice suggesting AR-42's efficacy may be related to its suppression of systemic IL-6 activation which is thought to drive muscle wasting in the C-26 model (Tseng Y C, et al. J Natl Cancer Inst. 2015 107(12):djv274). In this study, the impact of C-26 tumor burden and treatment with AR-42, GTx-024 or combination therapy on a panel of circulating cytokines, including IL-6, was assessed (FIG. 4A, Table 1). Multiple pro-cachectic factors, including G-CSF, IL-6, and LIF, were significantly elevated by the presence of C-26 tumors (Tseng Y C, et al. J Natl Cancer Inst. 2015 107(12):djv274). Unlike the 50 mg/kg dose, 10 mg/kg AR-42 did not significantly impact IL-6 family cytokine levels (i.e. IL-6 or LIF) alone or in combination with GTx-024. Furthermore, 10 mg/kg AR-42 monotherapy did not significantly reduce circulating levels of any evaluated cytokine, despite demonstrating clear anti-cachectic effects across the multiple studies presented here (FIG. 1D, FIG. 2, FIG. 10). An ELISA analysis confirmed our findings that AR-42 treatment did not affect circulating IL-6 levels (FIG. 4B), and demonstrated serum IL-6 levels were not associated with terminal body weight in treated, C-26 tumor-bearing mice at sacrifice (FIG. 4C).

Figure 4D:
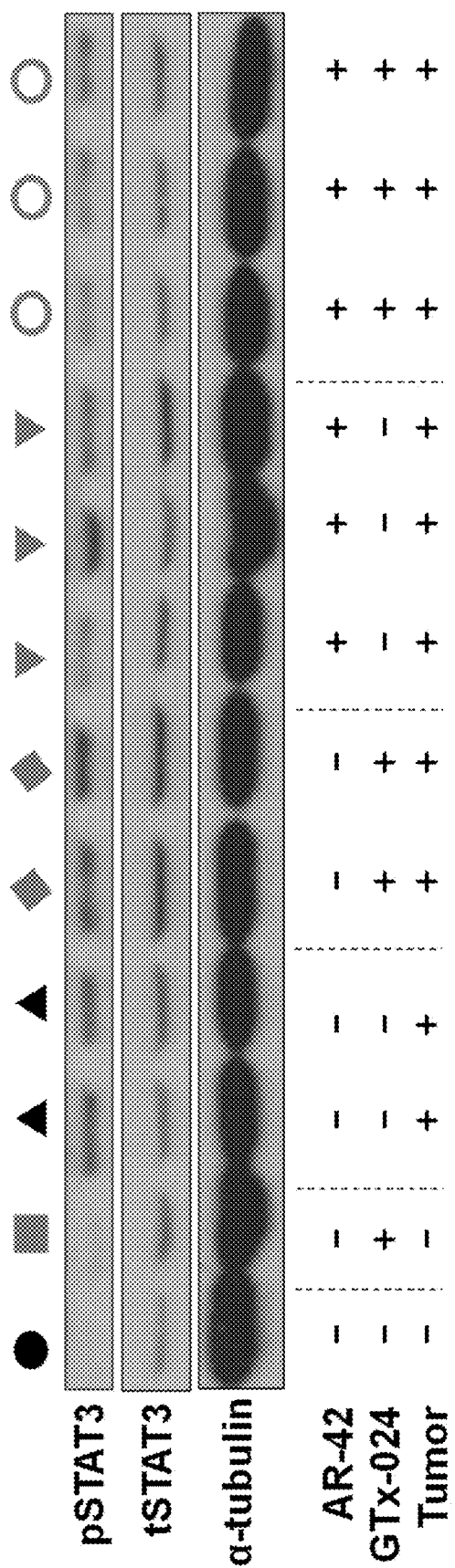
FIG. 4D shows STAT3 western blot analysis of gastrocnemius tissues from representative animals treated in Study 1.
Figure 13:
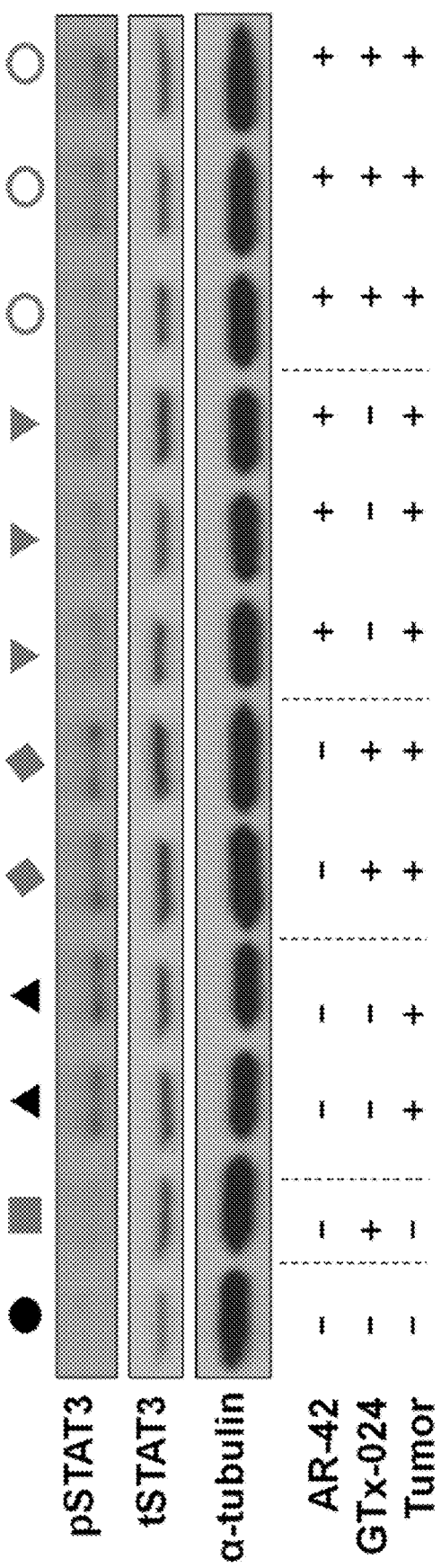
FIG. 13 shows western blot analysis of phosphoSTAT3 (pSTAT3) in gastrocnemius muscles from representative mice treated in Study 1. This data is a replicate blot from the samples used in FIG. 4D.

When significant effects on circulating cytokines were not apparent, AR-42 might be acting downstream of the IL-6 receptor on critical mediators of cytokine signaling. One well characterized effector of cytokine-induced signaling shown to be central to tumor-induced wasting in a number of models is signal transducer and activator of transcription (STAT)3 (White J P, et al. Biol Open. 2013 2(12):1346-53; Bonetto A, et al. PloS one. 2011 6(7):e22538). Notably, STAT3 activation is associated with the severity of wasting in both the C-26 and APC/min models of cancer cachexia, and AR-42 was previously shown to suppress the IL-6/GP130/STAT3 signaling axis in multiple myeloma cells (Zhang S, et al. Int J Cancer. 2011 129(1):204-13). Thus, AR-42's effects on phospho-STAT3 (pSTAT3) were evaluated in gastrocnemius muscle from C-26 tumor-bearing animals (FIG. 4D, FIG. 13). As expected, the presence of the C-26 tumor resulted in increased pSTAT3 abundance. GTx-024 treatment had no apparent effect on pSTAT3, consistent with its inability to spare body weight or lower limb skeletal muscle mass as a monotherapy. AR-42 monotherapy reduced pSTAT3 but not equally in all animals, whereas the combination treatment exhibited the most consistent suppression, concordant with its marked anti-cachectic efficacy. Furthermore, treatment-mediated effects on the well characterized STAT3 target gene CEBPδ (Silva K A, et al. J Biol Chem. 2015 290(17):11177-87) closely paralleled those on STAT3 activation (FIG. 3A).

Figure 4F:
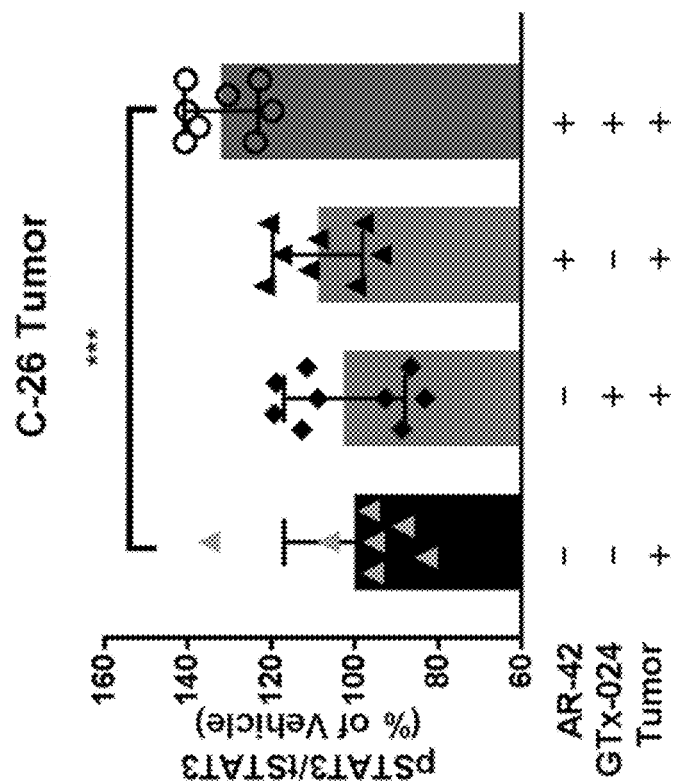
FIG. 4F is a bar graph showing ELISA analysis of STAT3 within C-26 tumors from Study 2. Statistics for all panels: Mean±SD, *p<0.05, p<0.01, *p<0.001, ****p<0.0001 versus tumor-bearing vehicle-treated controls, Dunnett's multiple comparison test.
Figure 4E:
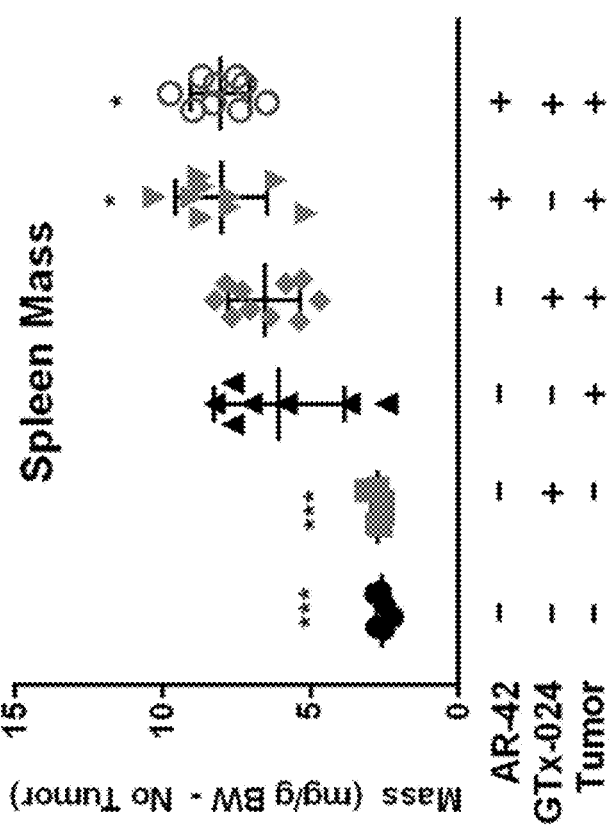
FIG. 4E is a plot showing spleen weights normalized to tumor-corrected terminal body weights of mice from Study 2.

In addition to skeletal muscle STAT3 activation, C-26 tumor-bearing mice exhibit splenomegaly as a result of increased systemic inflammation (Aulino P, et al. BMC cancer. 2010 10:363). Consistent with increased circulating cytokine levels, C-26 tumor-bearing animals in both Study 1 and 2 demonstrated large increases in spleen mass across all treatment groups relative to tumor-free controls (FIG. 9C and FIG. 4E, respectively). Similar to findings with 50 mg/kg AR-42 (Tseng Y C, et al. J Natl Cancer Inst. 2015 107(12):djv274), spleen mass was either unchanged or slightly increased by AR-42 alone or in combination with GTx-024. As a gross measure of the systemic effects of treatment on immune function, these spleen mass results suggest AR-42 is not generally immunosuppressive and its activity is distinct from inhibitors of the JAK/STAT pathway in this context (Mesa R A, et al. Nat Rev Drug Discov. 2012 11(2):103-4). Unlike in gastrocnemius tissue, AR-42 treatment did not significantly suppress pSTAT3 signaling within the C-26 tumors (FIG. 4F). Taken together, these multiple lines of evidence suggest that the anti-cachectic efficacy of AR-42 involves the inhibition of the IL-6/GP130/STAT3 axis in skeletal muscle tissue, but not systemic suppression of IL-6 or general immune signaling.

Transcriptomic Analyses of AR-42's Anti-Cachectic Effects in Skeletal Muscle

Figure 5A:
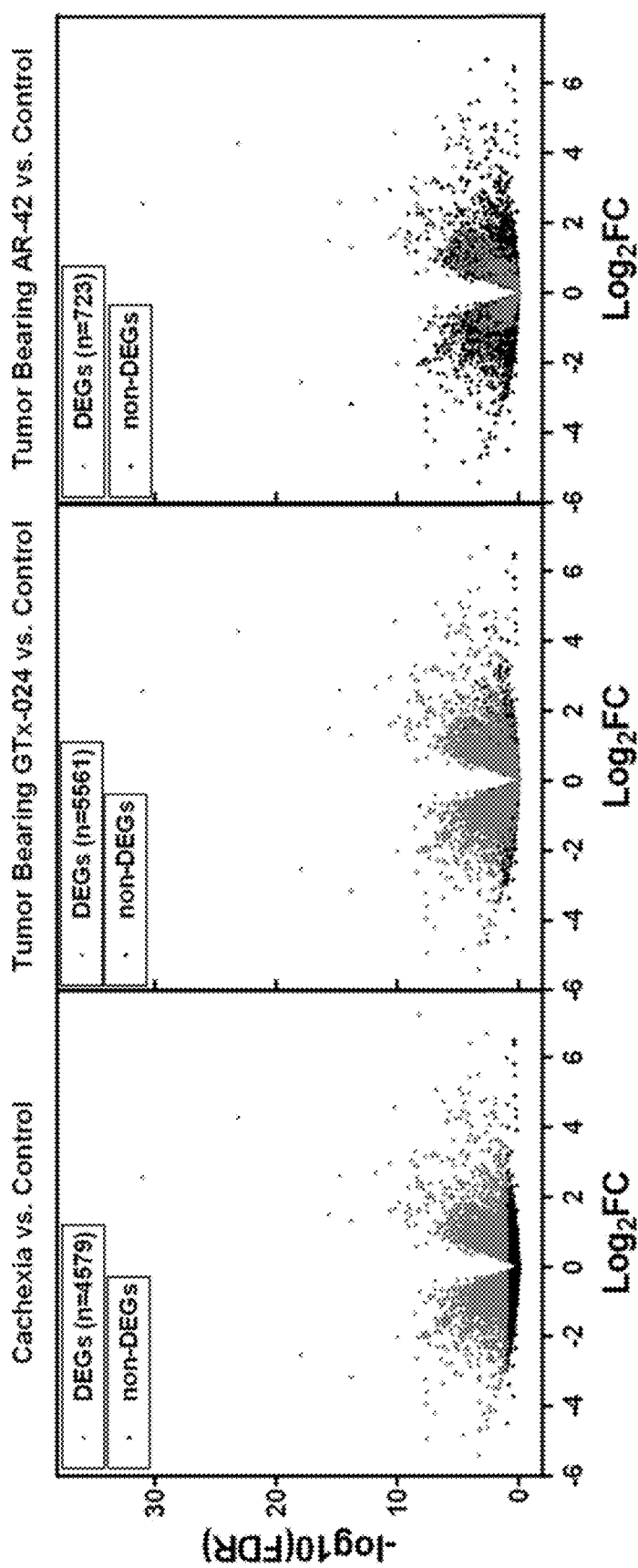
FIG. 5A shows effect of GTx-024 and AR-42 monotherapies on cachexia-related DEGs from RNA-seq analyses of Study 1 gastrocnemius muscles. All three panels consist of individual genes plotted with respect to their log 2 fold change and -log 10 Benjamini-Hochburg adjusted p-values from the comparison of cachexia vs tumor-free controls. Colors of the points reflect the DEG status of each gene for the given comparison.
Figure 5B:
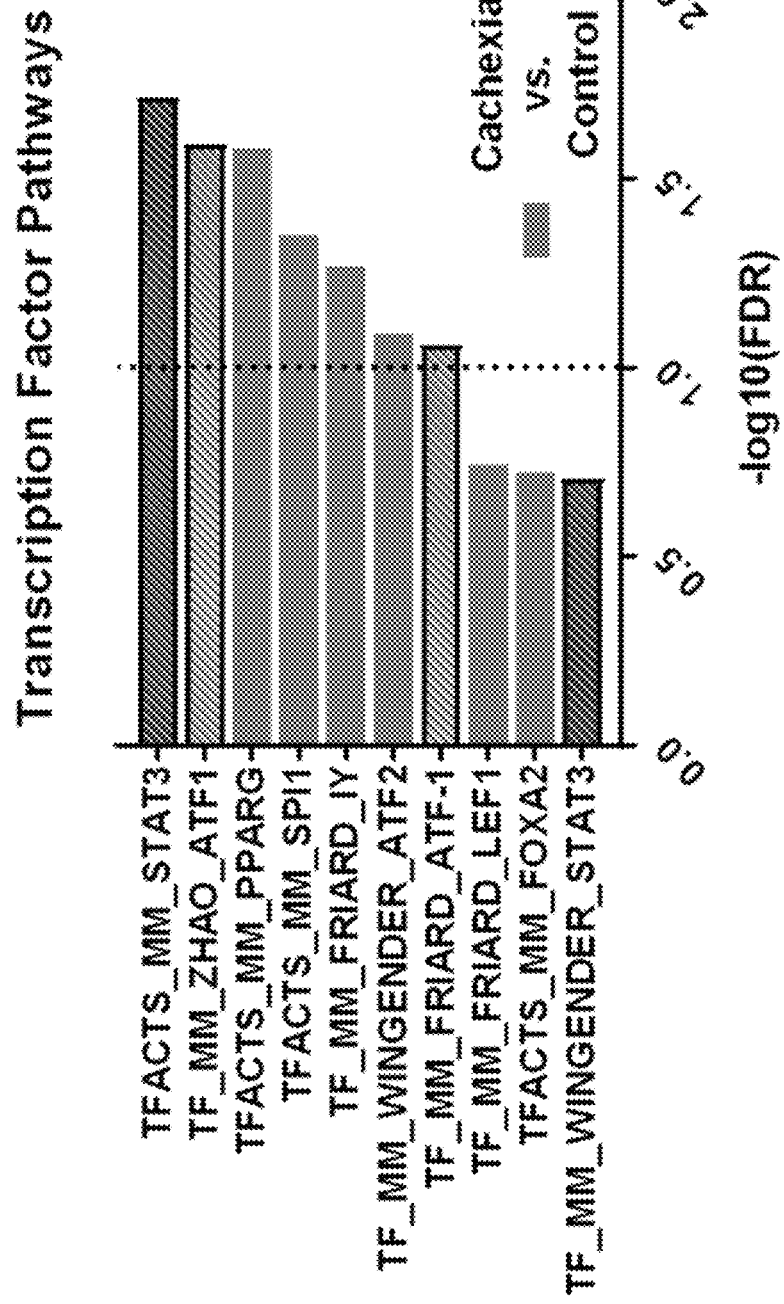
FIG. 5B is a bar graph showing results from transcription factor pathway-focused GSEA of tumor-bearing (cachexia) versus tumor-free control transcriptomes. STAT3 and ATF-1 gene sets used for subsequent combined analyses are hatched.
Figure 5C:
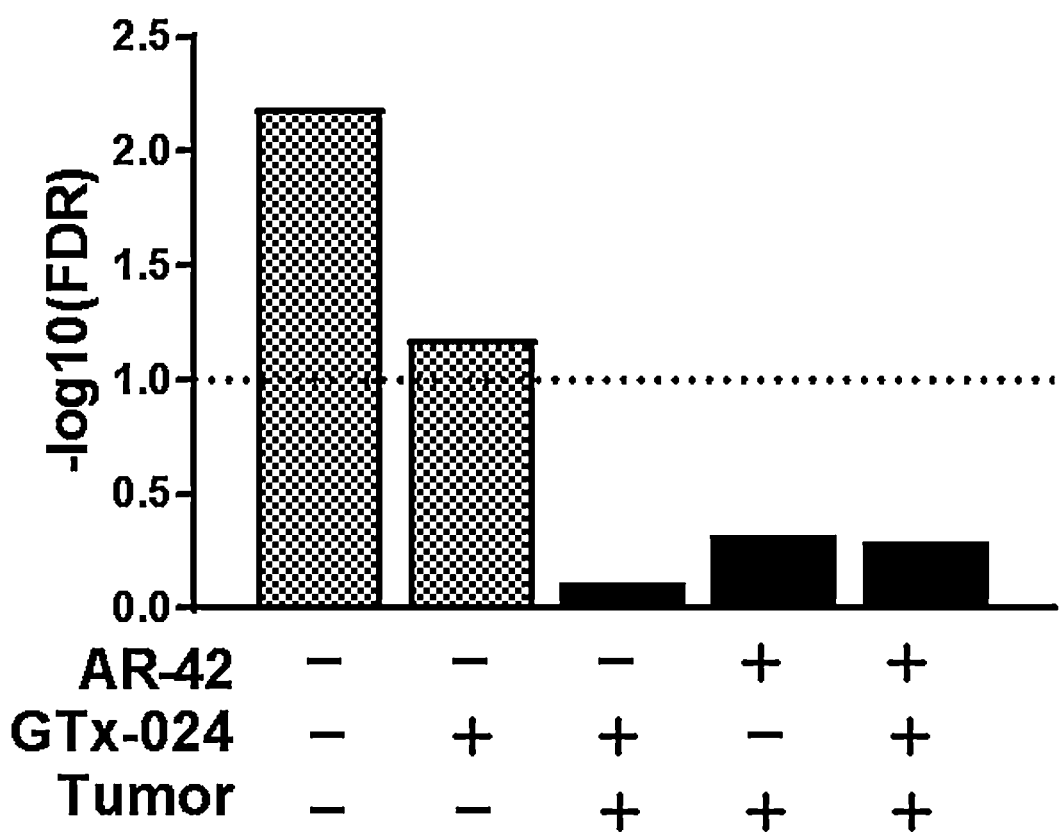
FIG. 5C is a bar graph showing significance values from GSEA using combined STAT3 gene sets identified in B. Each treatment group is compared to tumor-bearing control transcriptomes.
Figure 5D:
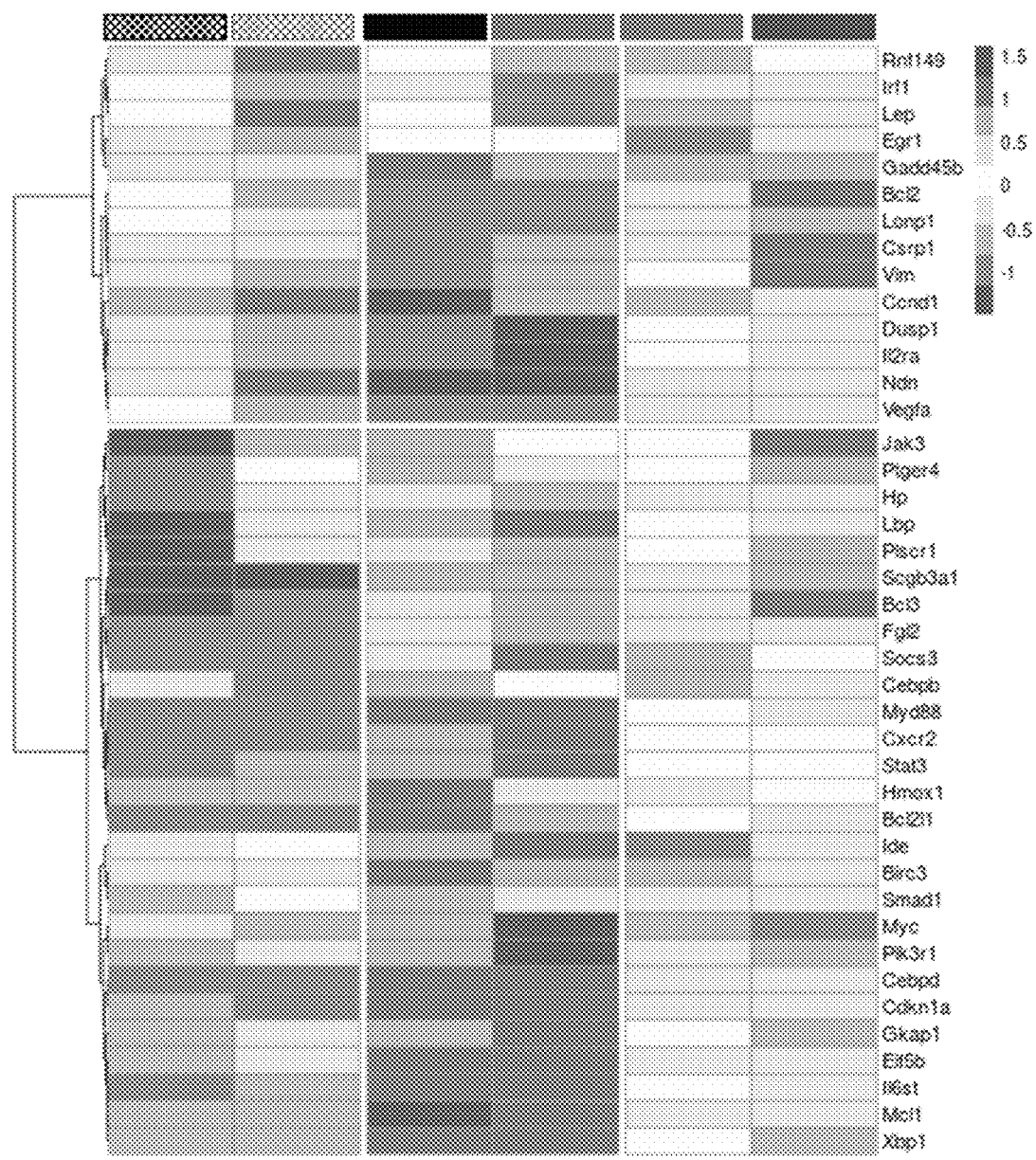
FIG. 5D is a heat map of DEGs within the combined STAT3 gene sets representing mean z scores calculated from normalized RNAseq count data. Tumor-free control, GTx-024 tumor-free, tumor-bearing control, GTx-024 tumor-bearing, AR-42 tumor-bearing, and Combination tumor-bearing.
Figure 5E:
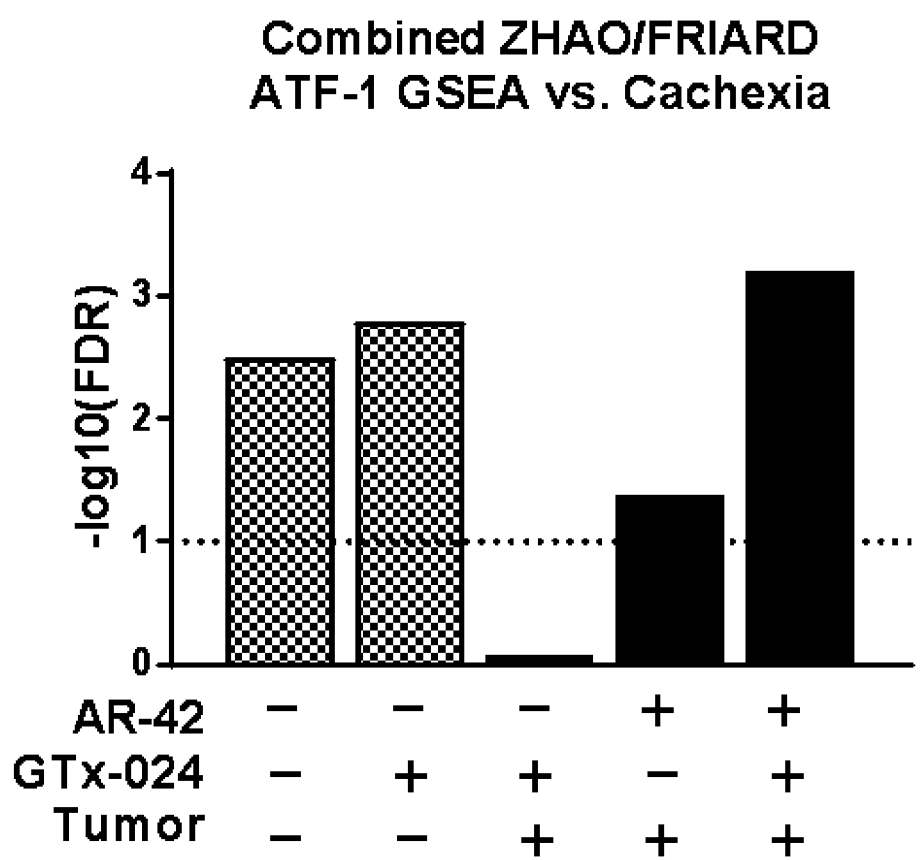
FIG. 5E is a bar graph showing results of GSEA using combined ATF-1 gene sets identified in B across treatment groups versus tumor-bearing control transcriptomes.
Figure 5F:
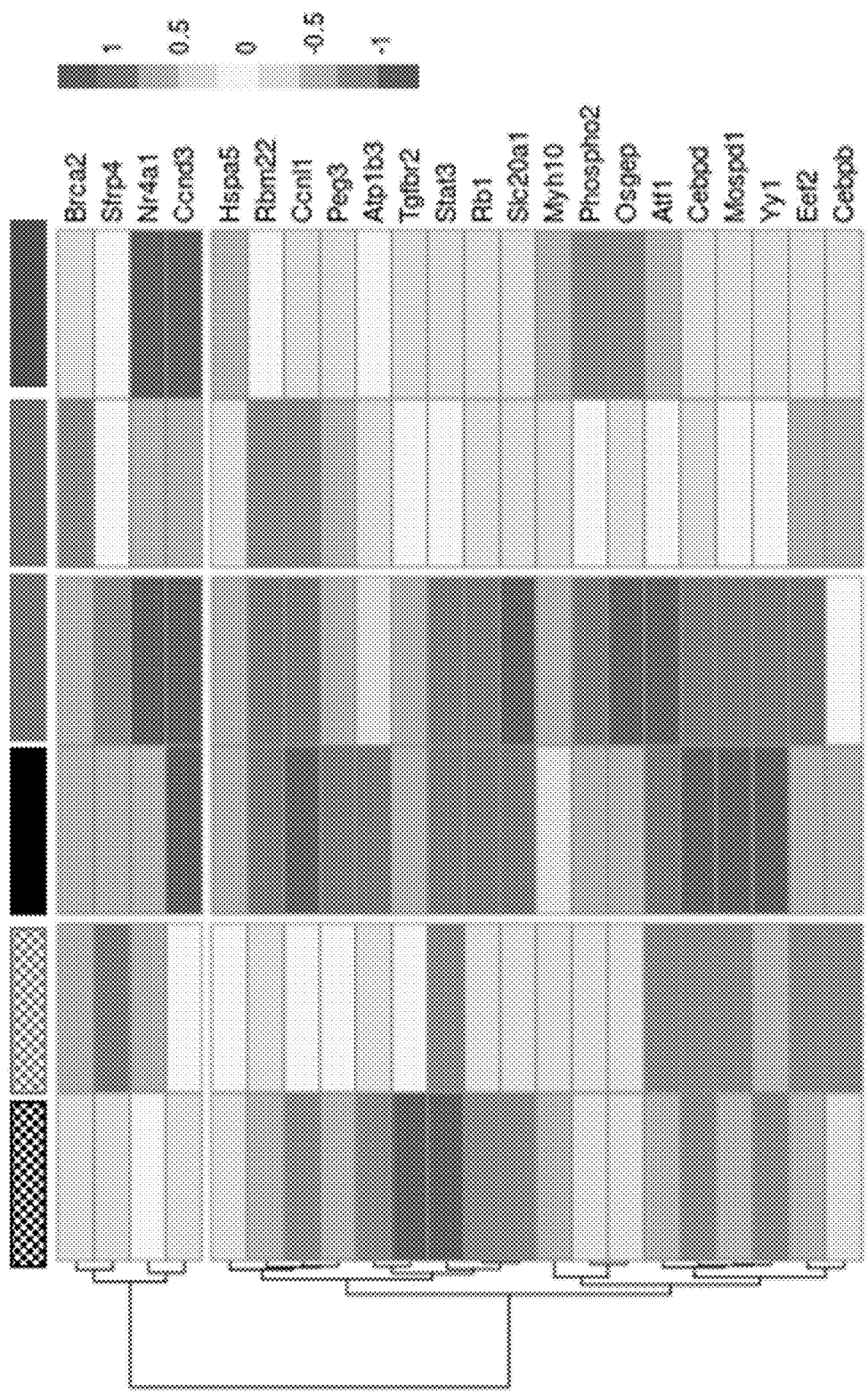
FIG. 5F is a heat map of DEGs within the combined ATF-1 gene sets (mean z score), treatment groups as in FIG. 5D.
Figure 14:
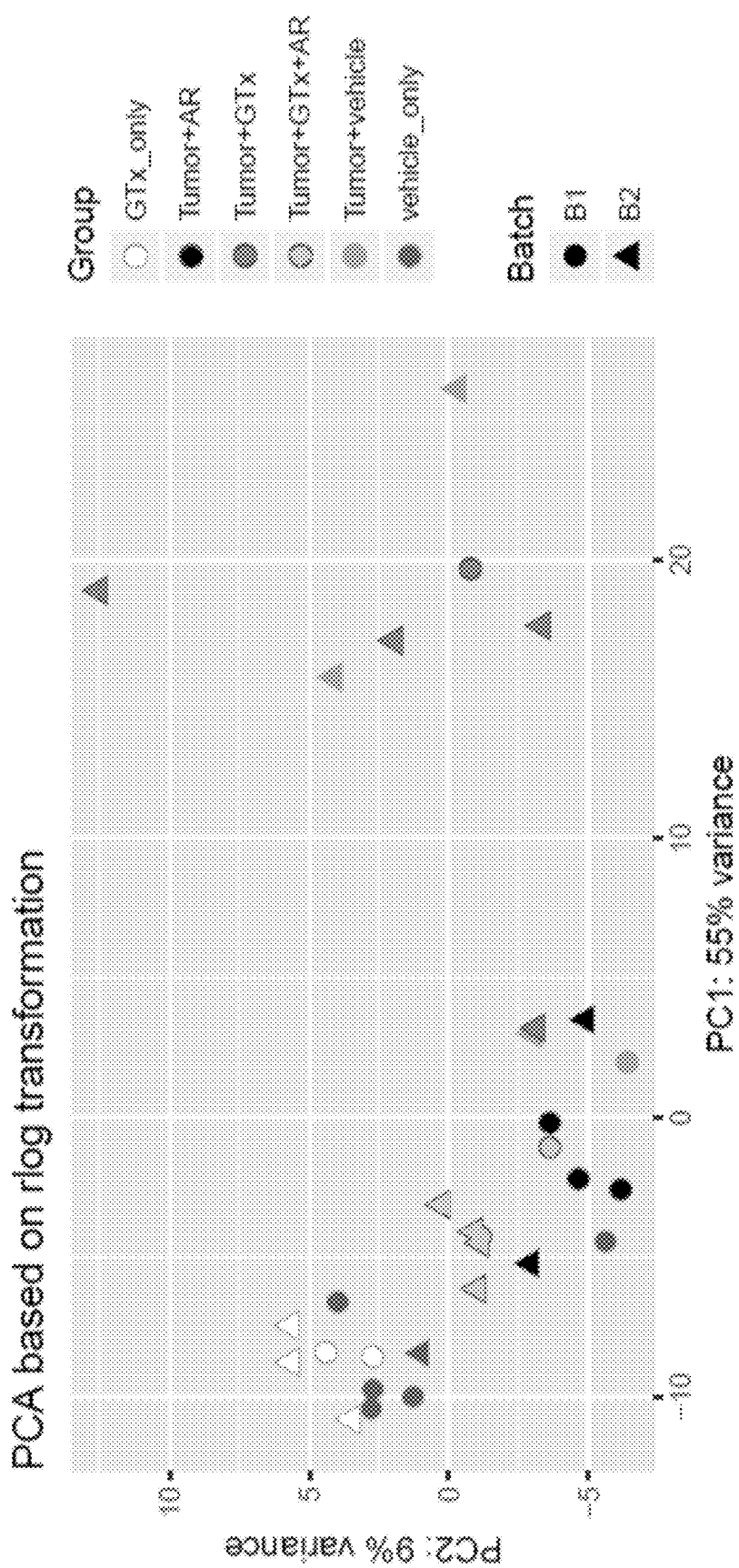
FIG. 14. Principle Component Analysis plots of Study 1 RNA-seq samples utilized for subsequent analyses.
Figure 15A:
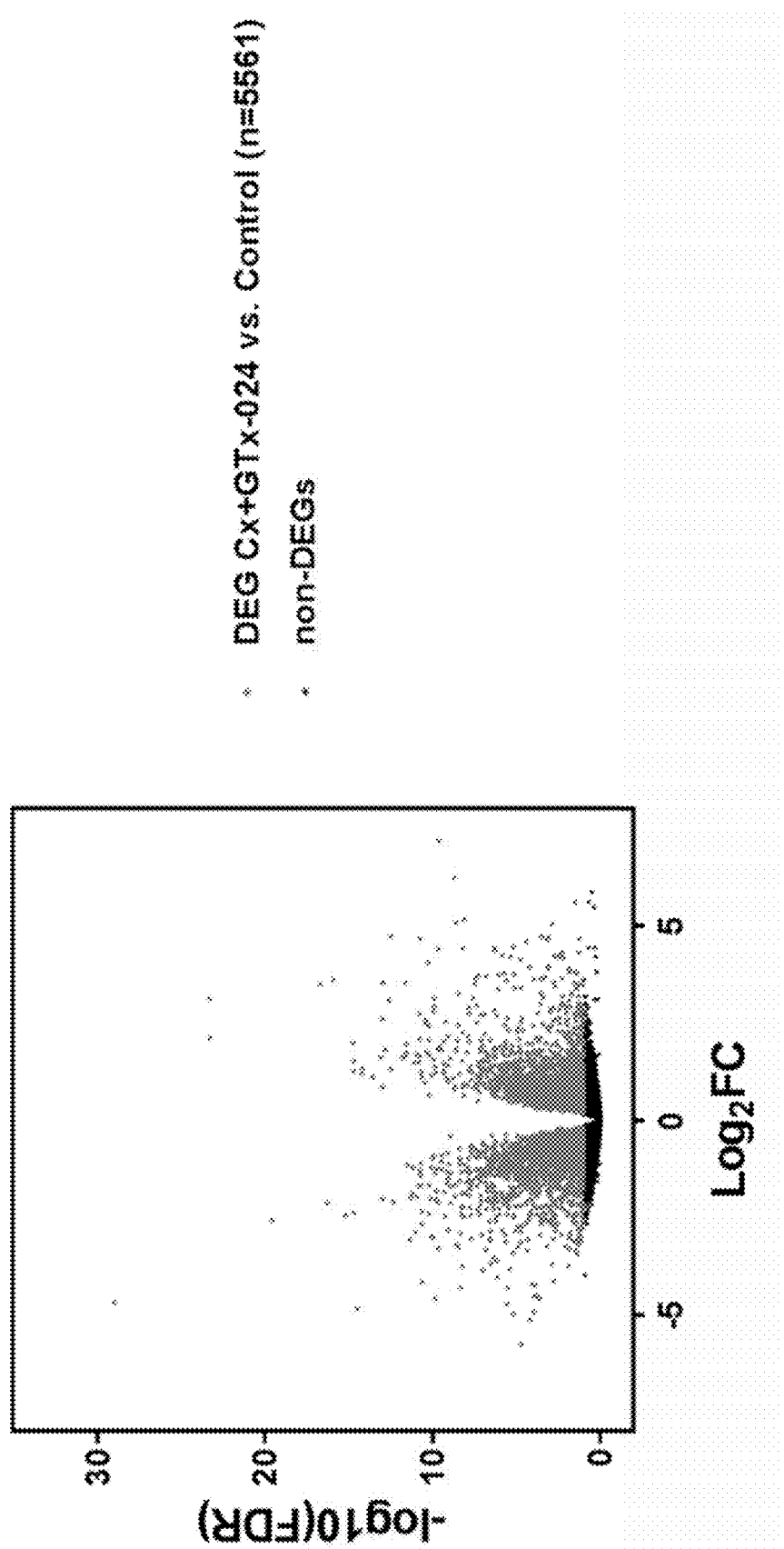
FIG. 15A-15B are standard volcano plots from RNA-seq analyses of Study 1 gastrocnemius muscles showing DEGs for tumor-bearing GTx-024-treated (Cx+GTx-024) mice versus tumor-free controls (FIG. 15A), and DEGs for tumor-bearing AR-42-treated (Cx+AR-42) mice versus tumor-free controls (FIG. 15B). Log-transformed fold change (FC) in expression is plotted on the x-axis and log-transformed false discovery rate (FDR)-adjusted p-values are plotted on the y-axis.
Figure 15B:
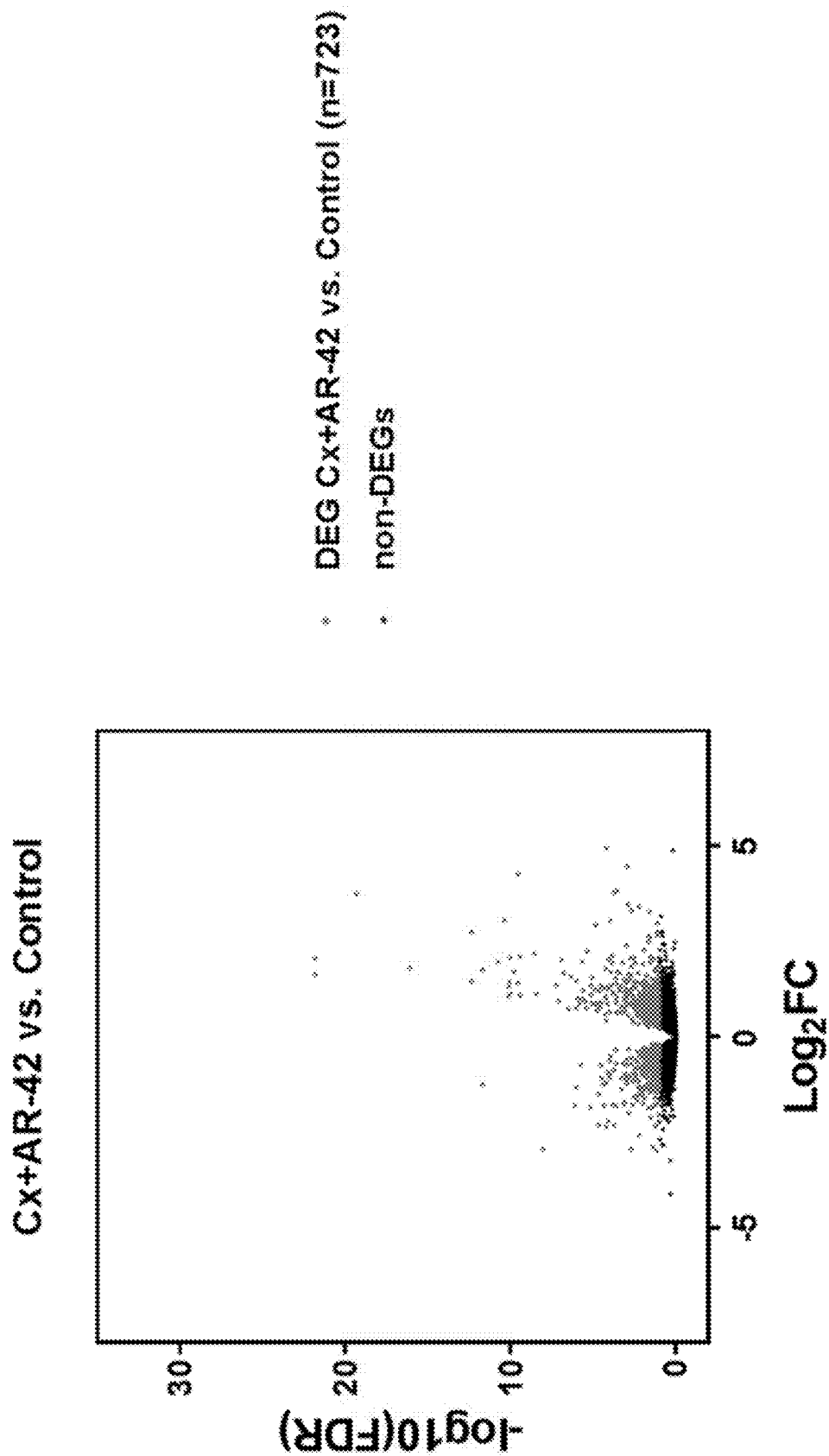
Figure 16B:
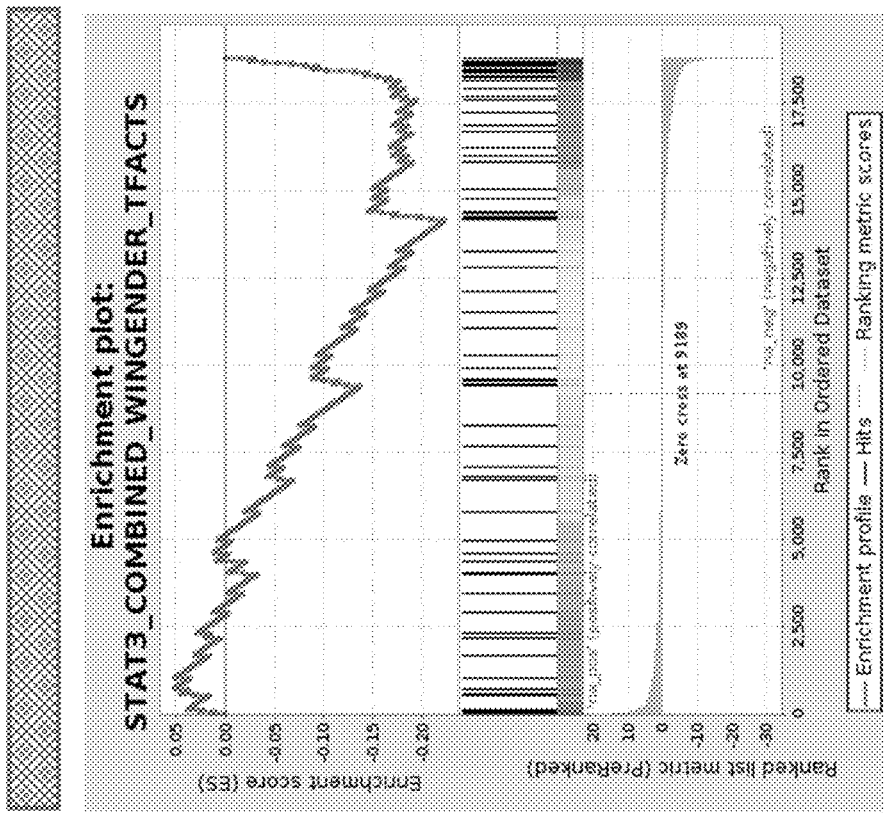
FIGS. 16A-16E are enrichment plots of the STAT3 gene set for each treatment group versus tumor-bearing control comparisons. Tumor-free control (black hatched), GTx-024-treated tumor-free, GTx-024-treated tumor-bearing, AR-42-treated tumor-bearing and Combination-treated tumor-bearing.
Figure 16A:
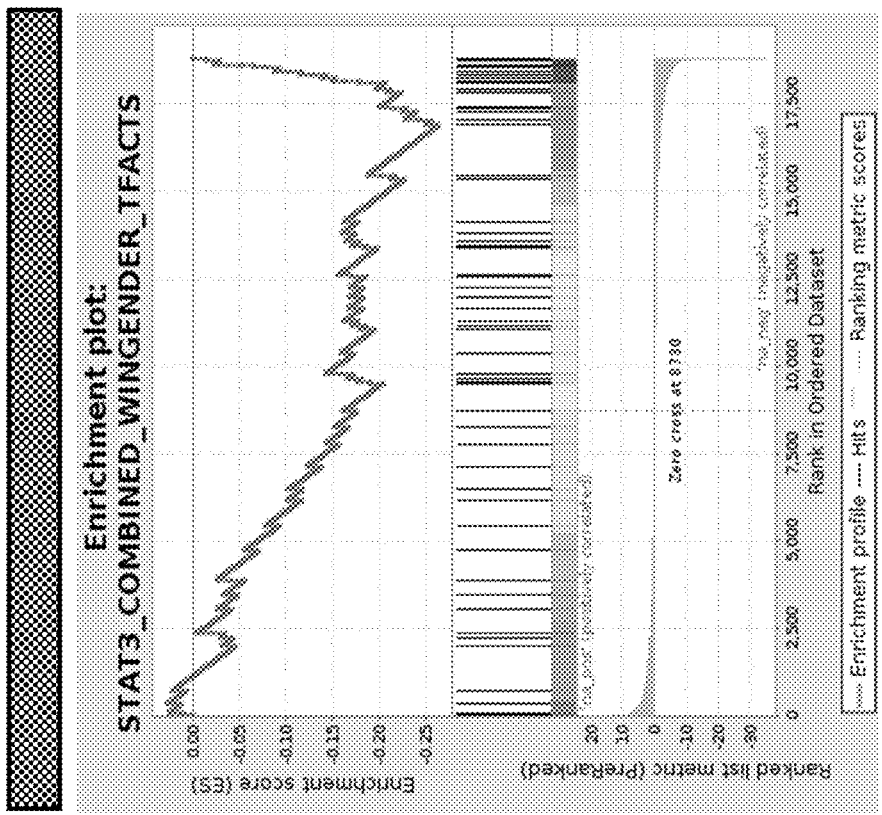
Figure 16D:
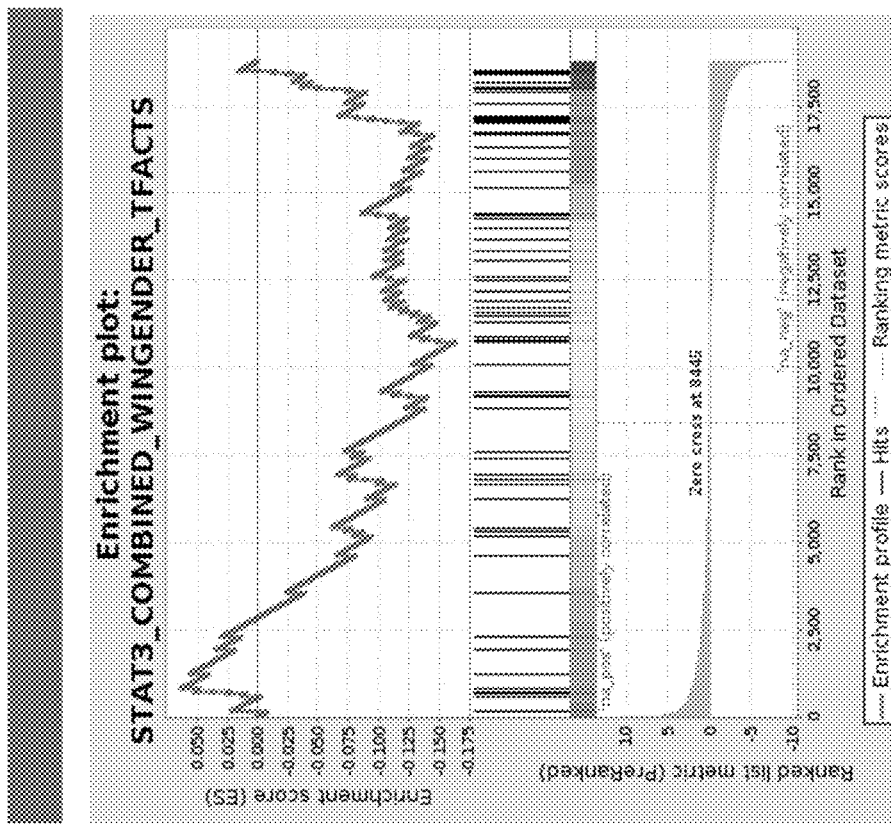
Figure 16C:
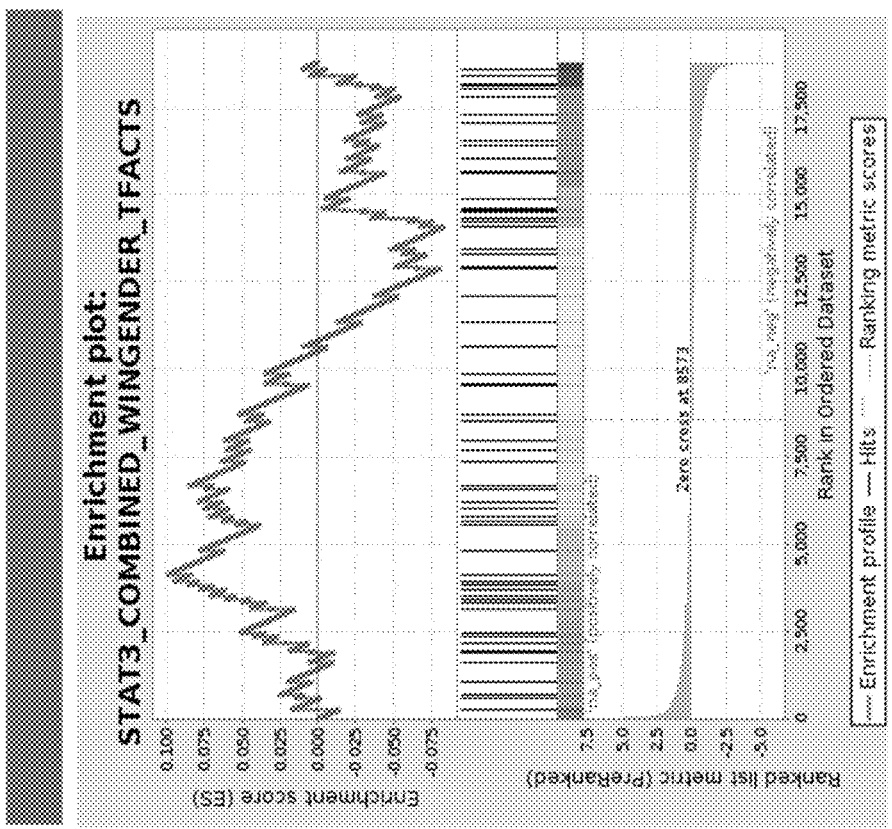
Figure 16E:
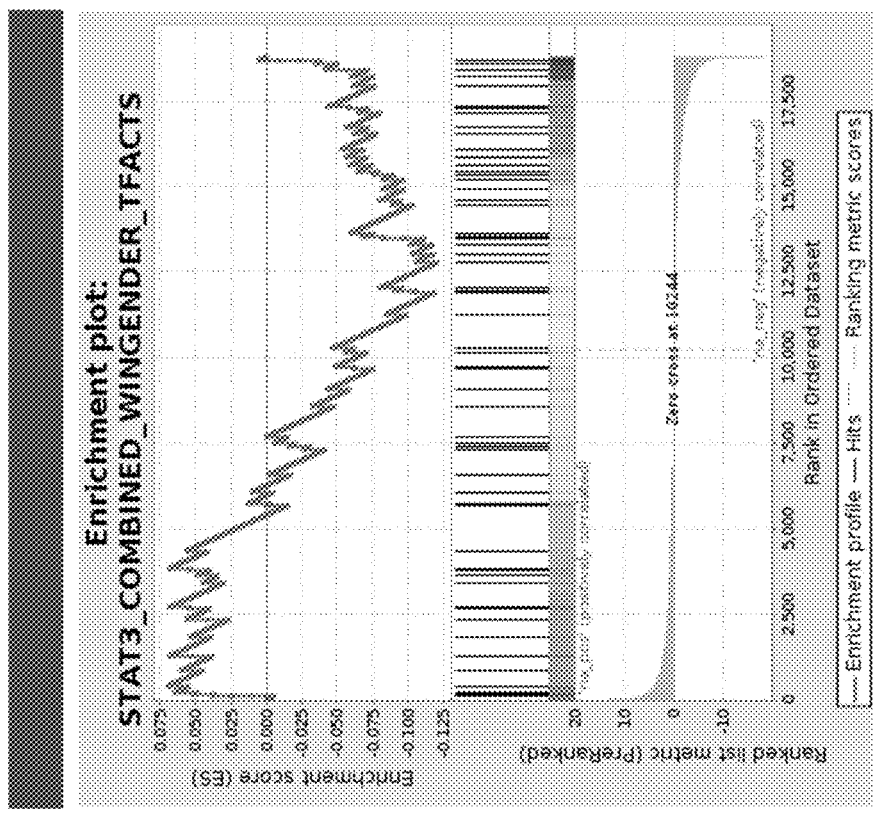
Figure 17B:
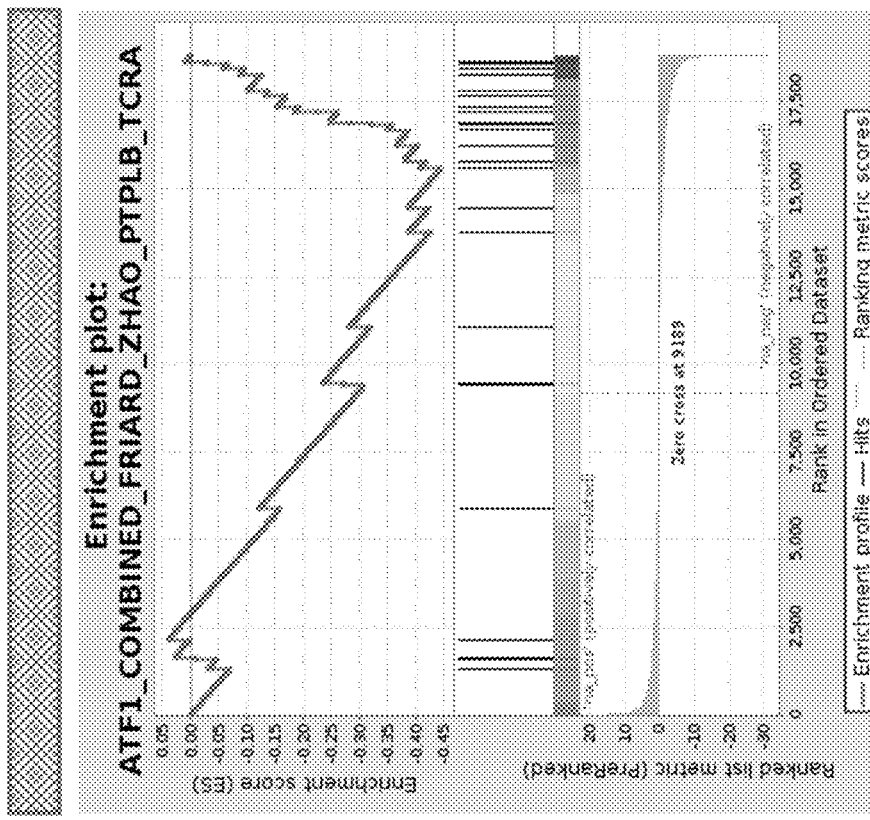
FIGS. 17A-17E are enrichment plots of the ATF-1 gene set for each treatment group versus tumor-bearing control comparisons. Tumor-free control (black hatched), GTx-024-treated tumor-free (blue hatched), GTx-024-treated tumor-bearing (blue), AR-42-treated tumor-bearing (red) and Combination-treated tumor-bearing (green).
Figure 17A:
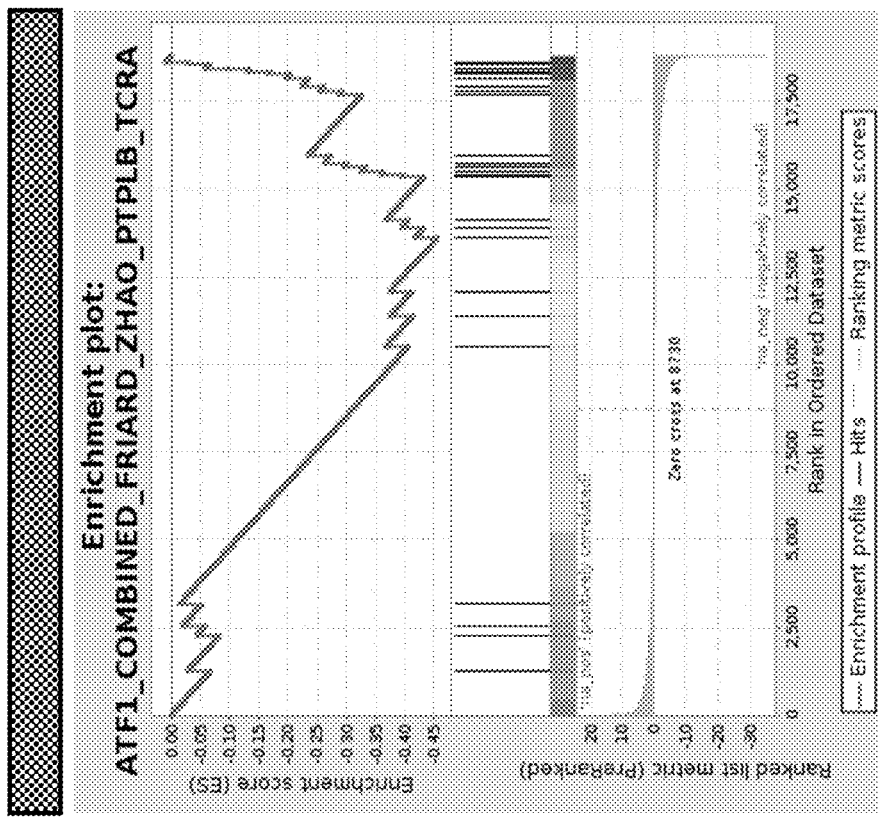
Figure 17D:
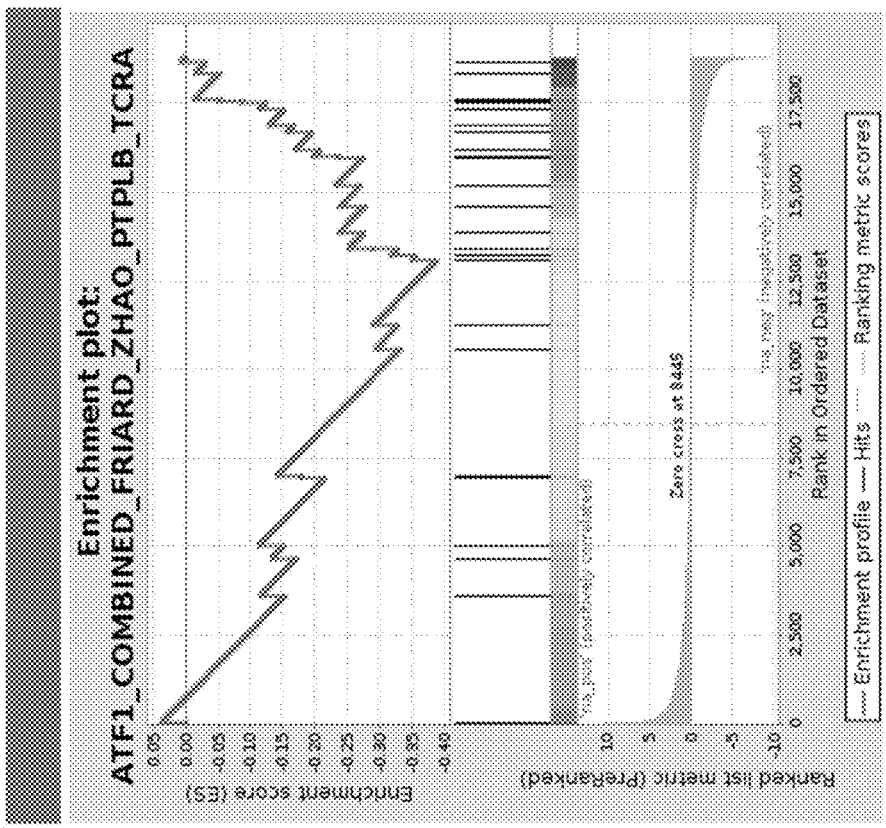
Figure 17C:
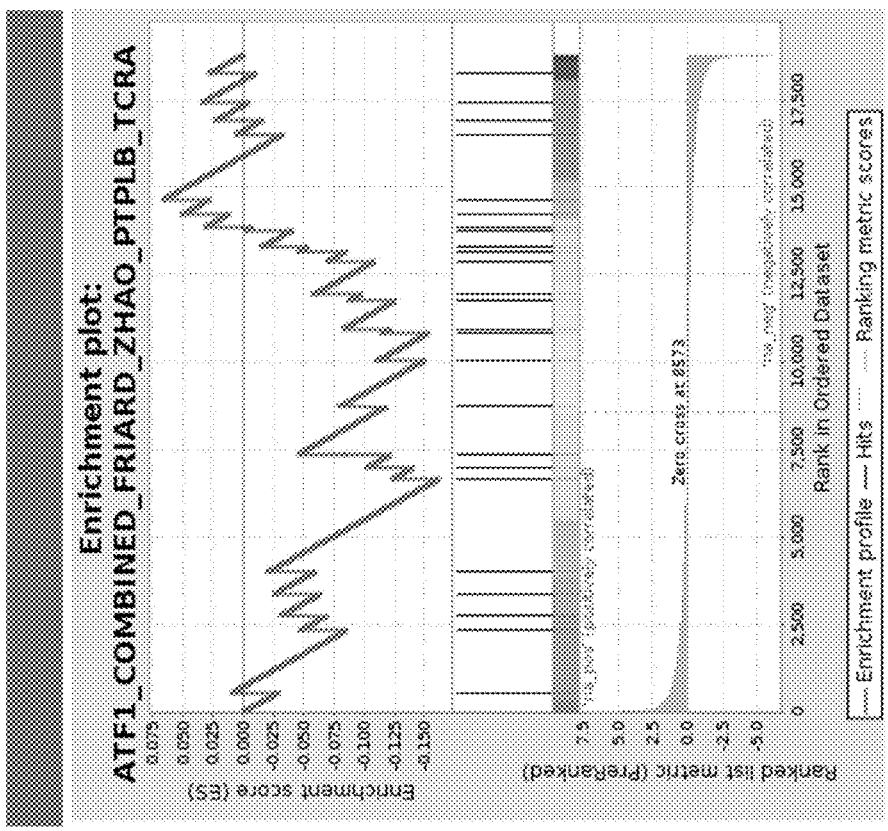
Figure 17E:
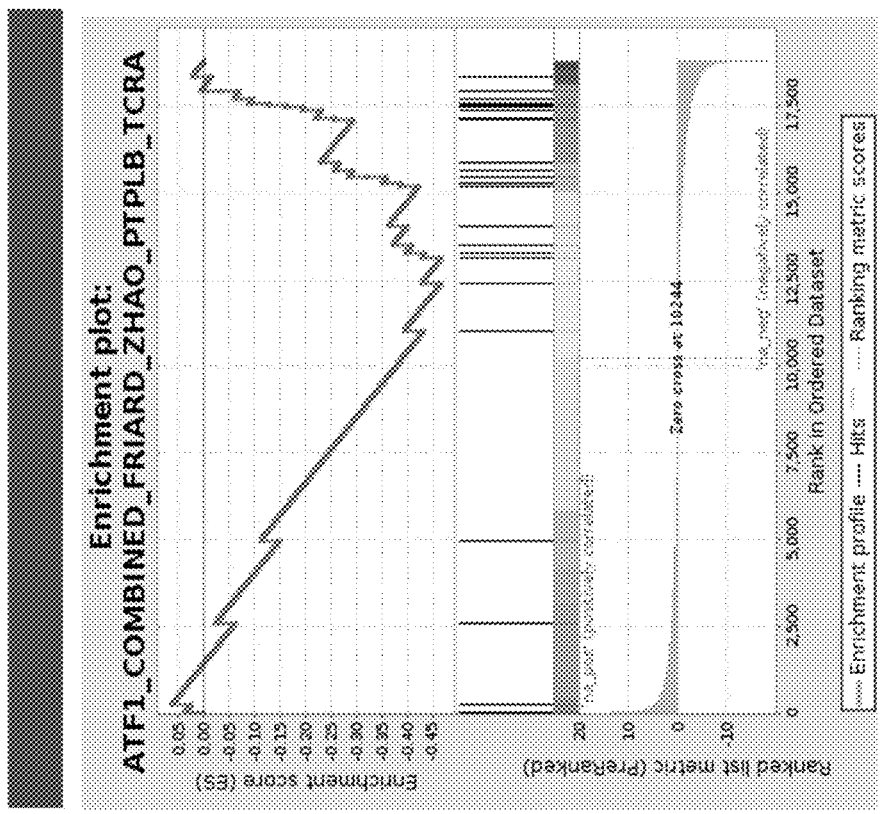

To further characterize AR-42's anti-cachectic effects at the reduced dose of 10 mg/kg, RNA-seq analyses were performed on all gastrocnemius tissues from Study 1 (FIG. 2A, B). This resulted in 31 evaluable samples across treatment groups (FIG. 14) after removal of two samples due to insufficient sequencing yield/quality. 4,579 differentially expressed genes (DEGs; FDR <0.1) were detected in cachectic versus control muscle, whereas treatment of cachectic mice with GTx-024 or AR-42 alone resulted in 5,561 and 723 DEGs, respectively, consistent with their corresponding anti-cachectic efficacies (FIG. 5A, FIGS. 15A and 15B). Given the ability of HDAC inhibitors and androgens to modulate transcription, initial functional analyses were focused on curated *Mus musculus* transcription factor (TF) target gene sets, and revealed multiple over-represented TF targets in cachectic versus control muscle (FIG. 5B). STAT3 and activation of transcription-1 (ATF1) gene sets were each represented twice in the top ten pathways following GSEA supporting their potential relevance in cachectic signaling. The two STAT3 target gene sets were combined and GSEA was repeated with the combined set for all treatment groups. In contrast to pSTAT3 activation (FIG. 4D), this analysis demonstrated the inability of any treatment in tumor-bearing mice to significantly limit the importance of STAT3 target-gene regulation relative to cachectic controls (FIG. 5C and FIG. 16). However, when analysis is focused on individual genes within the combined set that are differentially expressed in at least one comparison, clear cachexia-dependent regulation is apparent that responds only to AR-42 treatment (FIG. 5D). A similar analysis with combined ATF-1 data sets revealed the ability of AR-42, but not GTx-024 treatment, to significantly impact ATF-1 target gene regulation in tumor-bearing mice implicating AR-42's ability to modulate ATF-1 activation in its anti-cachectic efficacy (FIG. 5E and FIG. 17). Of note, STAT3 and CEPBδ are among the differentially expressed ATF-1 target genes induced by cachexia that respond only to AR-42 treatment (FIG. 5F).

Figure 5G:
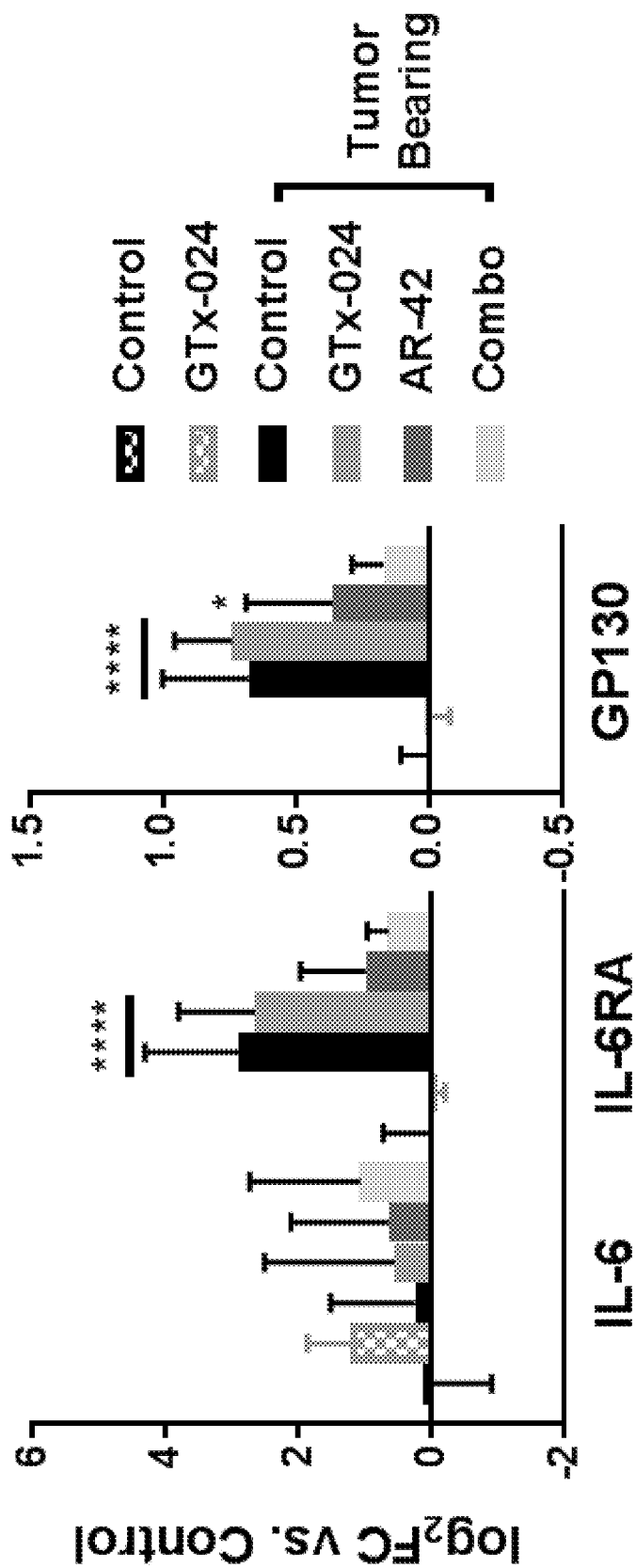
FIG. 5G is a bar graph showing mRNA expression of mediators of IL-6 signaling upstream of STAT3. Data presented as mean±SD of per animal log-transformed fold change (log 2FC) values versus tumor-free controls. *p<0.1, p<0.05, *p<0.01, ****p<0.001 based on Benjamini-Hochburg adjusted p-values from DESeq2.

The expression of genes within the IL-6 pathway were further evaluated as IL-6-mediated STAT3 target gene regulation is well characterized in the C-26 model (Bonetto A, et al. PloS one. 2011 6(7):e22538), and IL-6-mediated increases in skeletal muscle cyclic AMP (cAMP), a primary driver of ATF-1 activation (Rehfuss R P, et al. J Biol Chem. 1991 266(28):18431-4), have also been reported (Kelly M, et al. Diabetes. 2009 58(9):1953-60). Unlike circulating IL-6 cytokine, IL-6 mRNA in gastrocnemius muscle was not induced by cachexia, nor was it modulated by any treatment (FIG. 5G). However, expression of both IL-6 receptor (IL-6RA) and the key effector GP130 were elevated in cachectic mice and required AR-42 (IL-6RA) or combination treatment (GP130) to restore non-cachectic control levels.

Figure 18A:
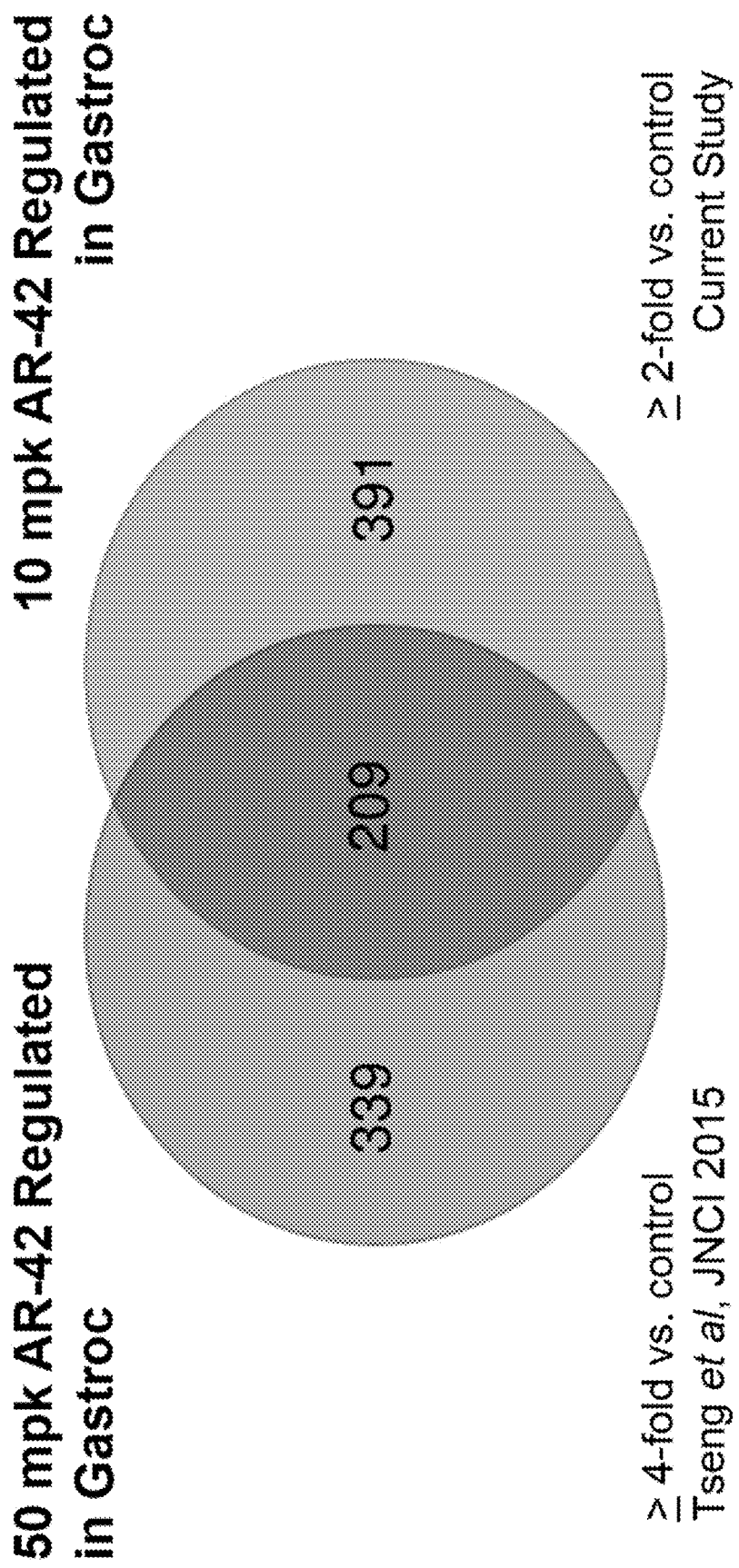
FIG. 18A shows genes differentially regulated 4-fold or greater in gastrocnemius muscle by 50 mg/kg AR-42 treatment relative to tumor-bearing vehicle-treated controls from Tseng et al. (Tseng Y C, et al. J Natl Cancer Inst. 2015 107(12):djv274) intersected with genes differentially regulated 2-fold or greater in gastrocnemius muscle by 10 mg/kg AR-42 treatment relative to tumor-bearing controls from Study 1.
Figure 18B:
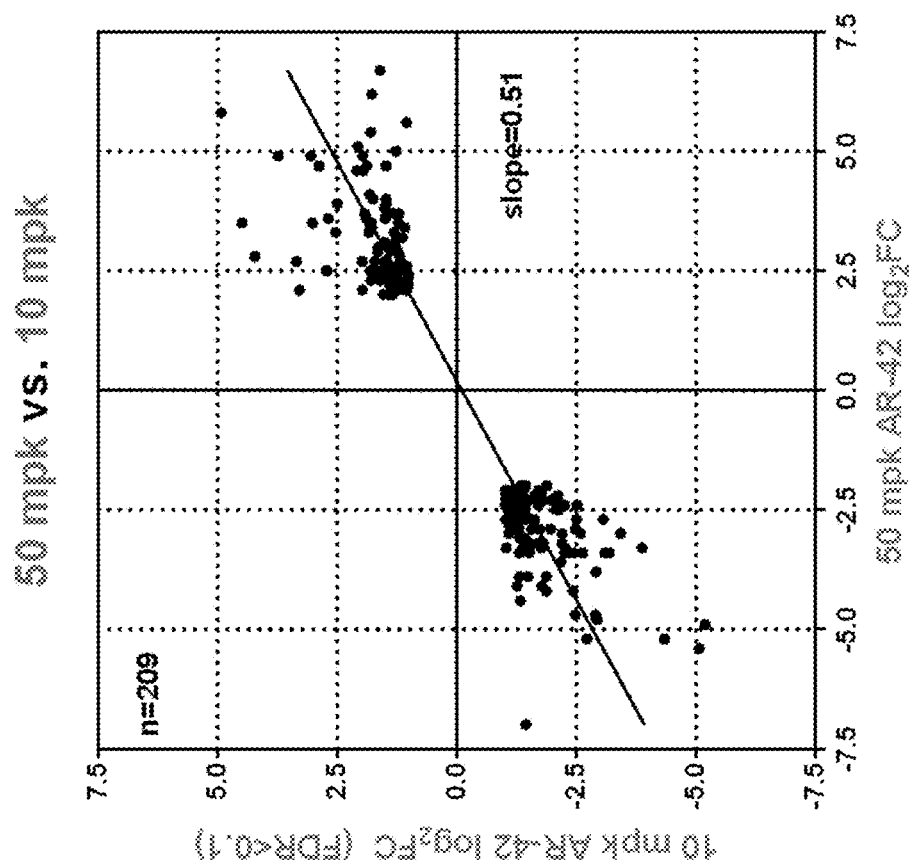
FIG. 18B is a scatter plot of the 209 overlapping genes identified in FIG. 18A.
Figure 18C:
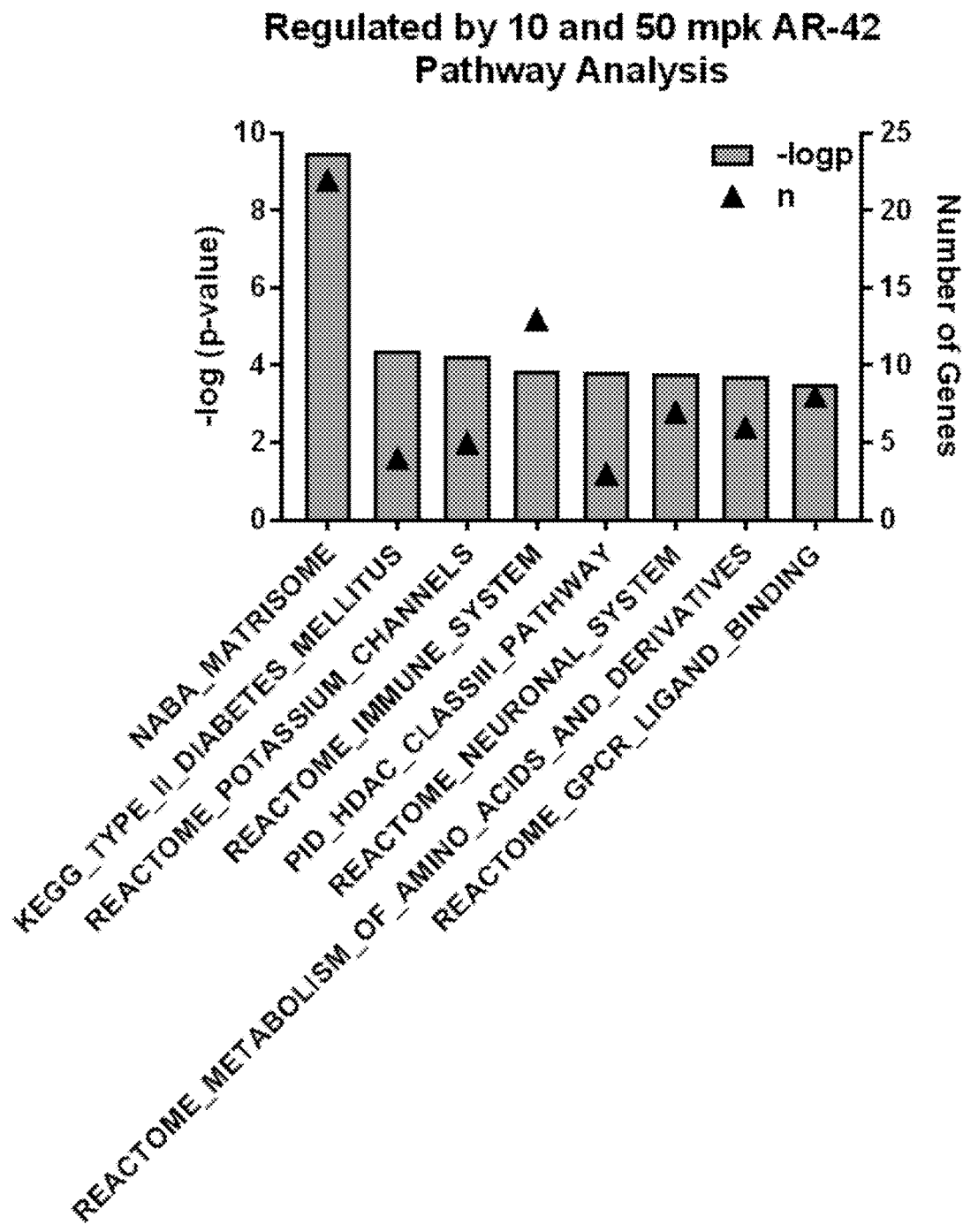
FIG. 18C is a bar graph showing canonical pathway analysis using the 147 overlapping genes identified in FIG. 18A.

Considerable overlap exists between the transcriptomes of cachectic gastrocnemius muscles from mice treated with 10 or 50 mg/kg AR-42 such that high fold-change DEGs identified Tseng et al. (Bonetto A, et al. PloS one. 2011 6(7):e22538) and in the current study are all regulated in the same direction (n=209, FIG. 18A-B). Similar to previous analyses (FIG. 11), functional interrogation of the genes within this overlap further support the importance of AR-42's ability to modulate immune and extracellular matrix signaling in eliciting its anti-cachectic effects (FIG. 18C). Taken together these findings support the ability of the reduced 10 mg/kg dose of AR-42 to generate anti-cachectic effects by reducing procachectic IL-6RA/GP130/STAT3 signaling in skeletal muscle.

Transcriptomic Analyses of GTx-024's Anabolic Effects in Skeletal Muscle

Figure 6A:
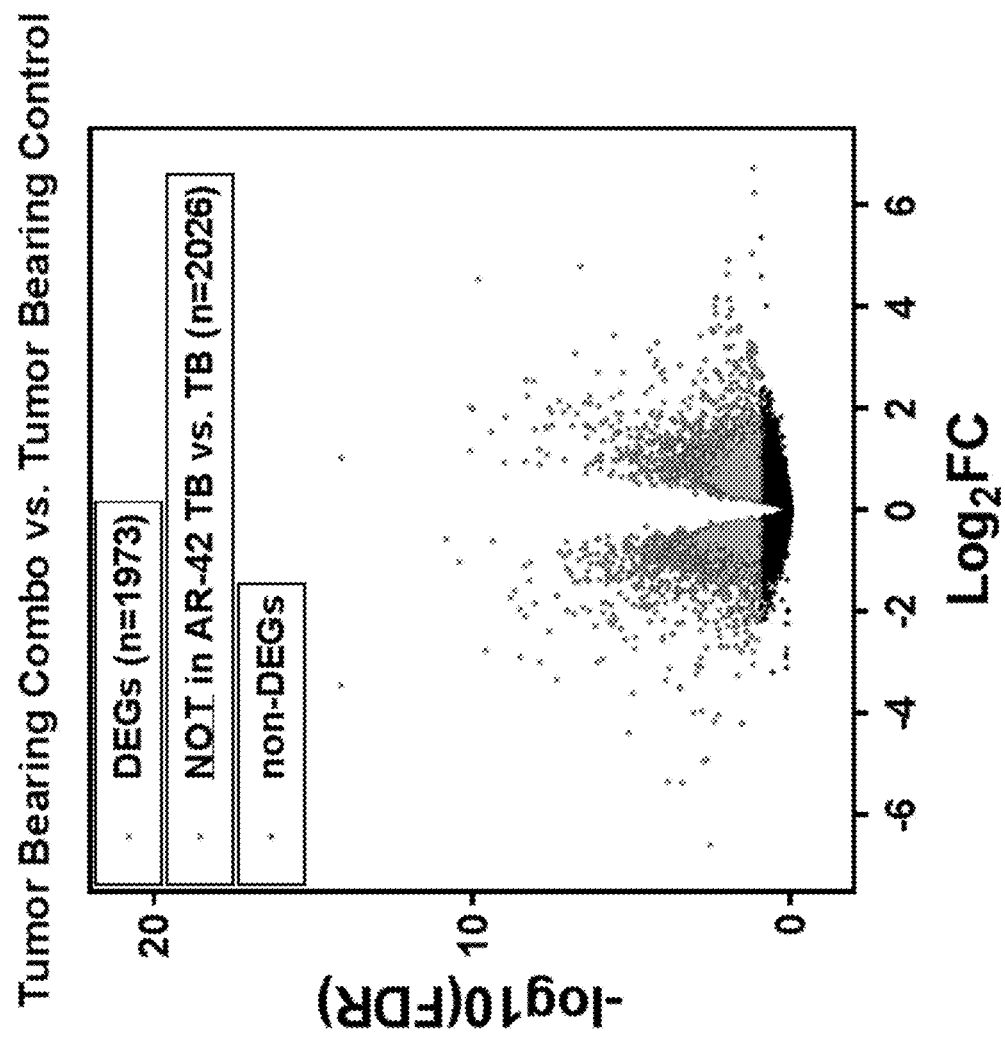
FIG. 6A is a volcano plot from RNA-seq analyses of Study 1 gastrocnemius muscles for tumor-bearing combination-treated mice versus tumor-bearing controls. Genes not differentially expressed in this comparison are indicated. The remaining genes are DEGs in the combination-treated versus tumor-bearing control comparison. The subset of these DEGs that are not also differentially expressed in the comparison of AR-42-treated tumor-bearing mice versus tumor-bearing controls is shown, suggesting these genes are responsive to only the combination therapy. Log 2-transformed fold change (FC) in expression is plotted on the x-axis and -log 10 transformed Benjamini-Hochburg adjusted p-values are plotted on the y-axis.
Figure 19:
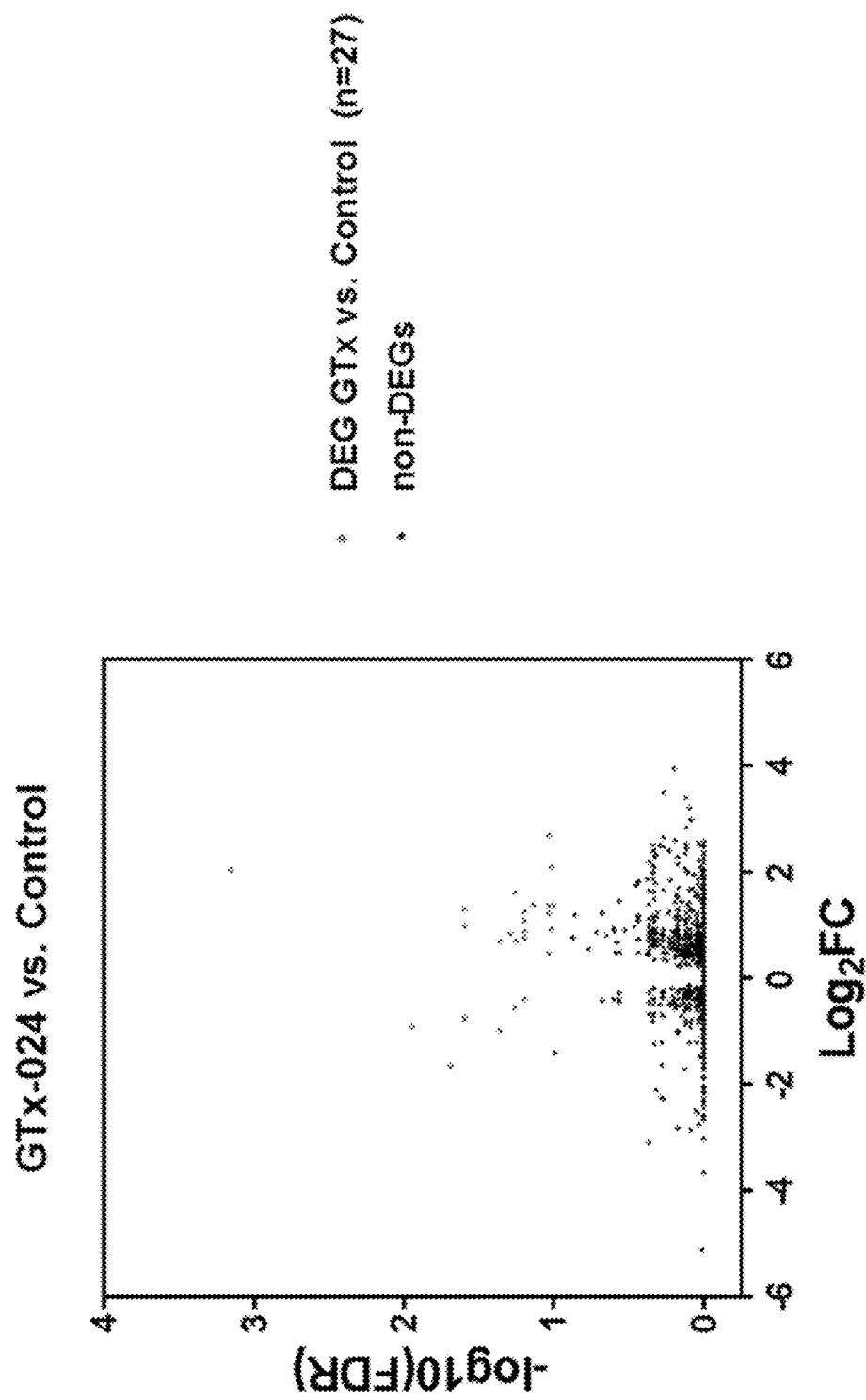
FIG. 19 is a standard volcano plot from RNA-seq analyses of Study 1 gastrocnemius muscles showing DEGs for GTx-024-treated tumor-free controls versus vehicle-treated tumor-free controls (colored red). Log-transformed fold change (FC) in expression is plotted on the x-axis and log-transformed false discovery rate (FDR)-adjusted p-values are plotted on the y-axis.
Figure 20A:
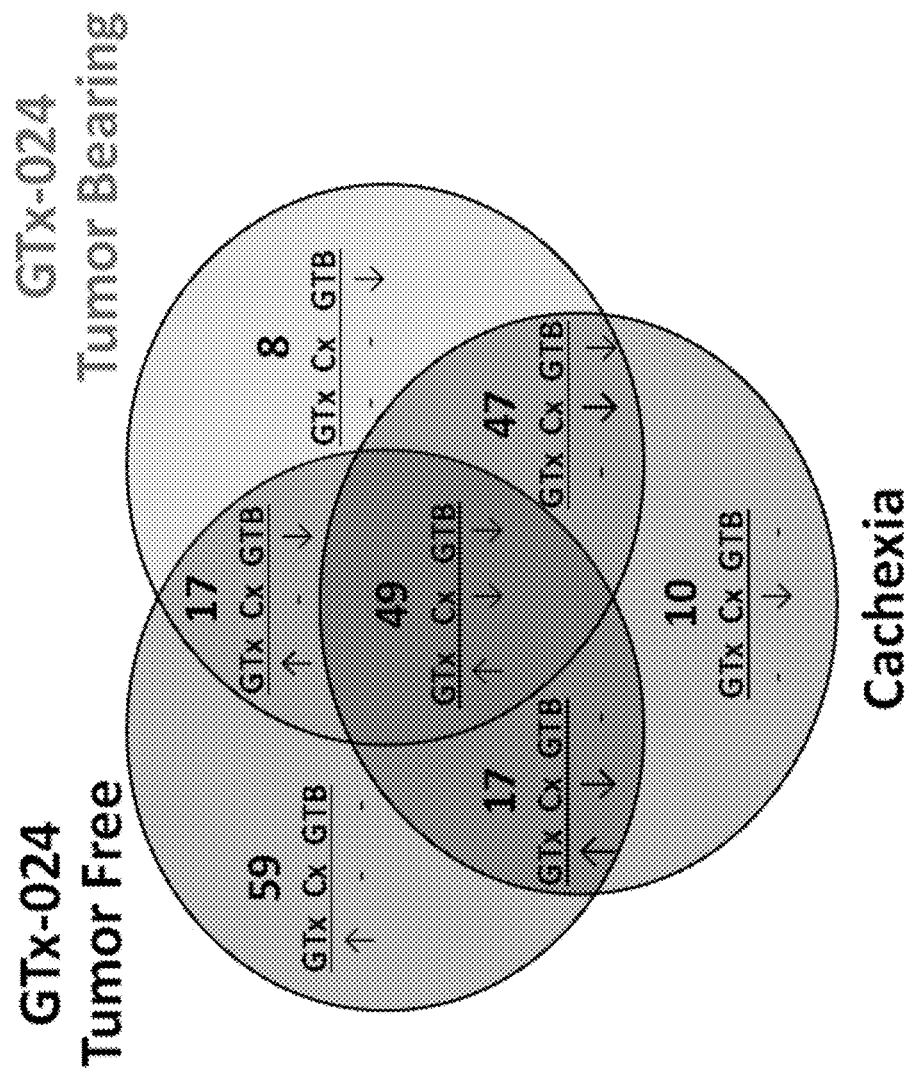
FIGS. 20A-20C show overlapping genes among leading-edge subsets from the enrichment analysis of the CTNNB1 gene set presented in FIG. 6 were identified. The comparisons performed were among GTx-treated tumor-free mice (GTx-024, No Tumor), tumor-bearing mice (Cachexia) and either GTx-024-treated tumor-bearing mice (GTx-024, Cachexia) (FIG. 20A), AR-42-treated tumor-bearing mice (AR-42, Cachexia) (FIG. 20B), or Combination-treated tumor-bearing mice (Combo, Cachexia) (FIG. 20C). In each case, the directionality of regulation compared to tumor-free controls is designated by arrows.
Figure 20B:
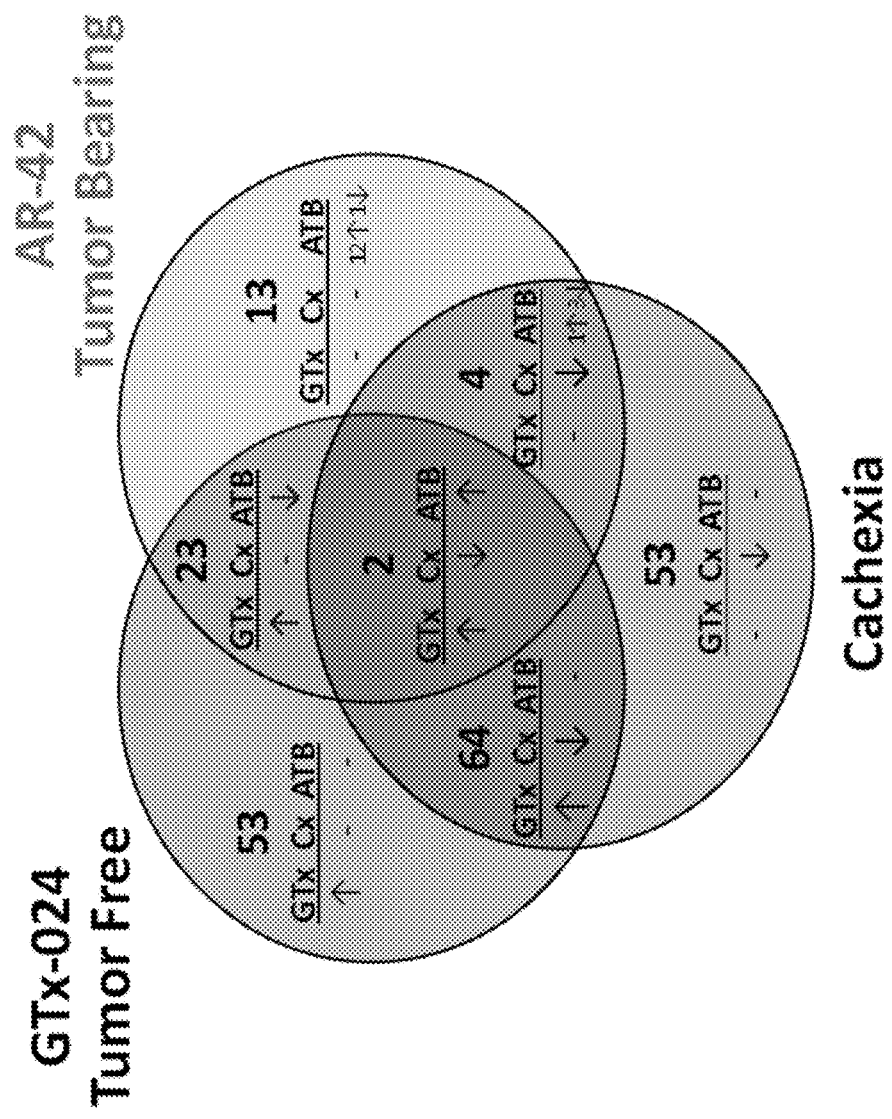
Figure 20C:
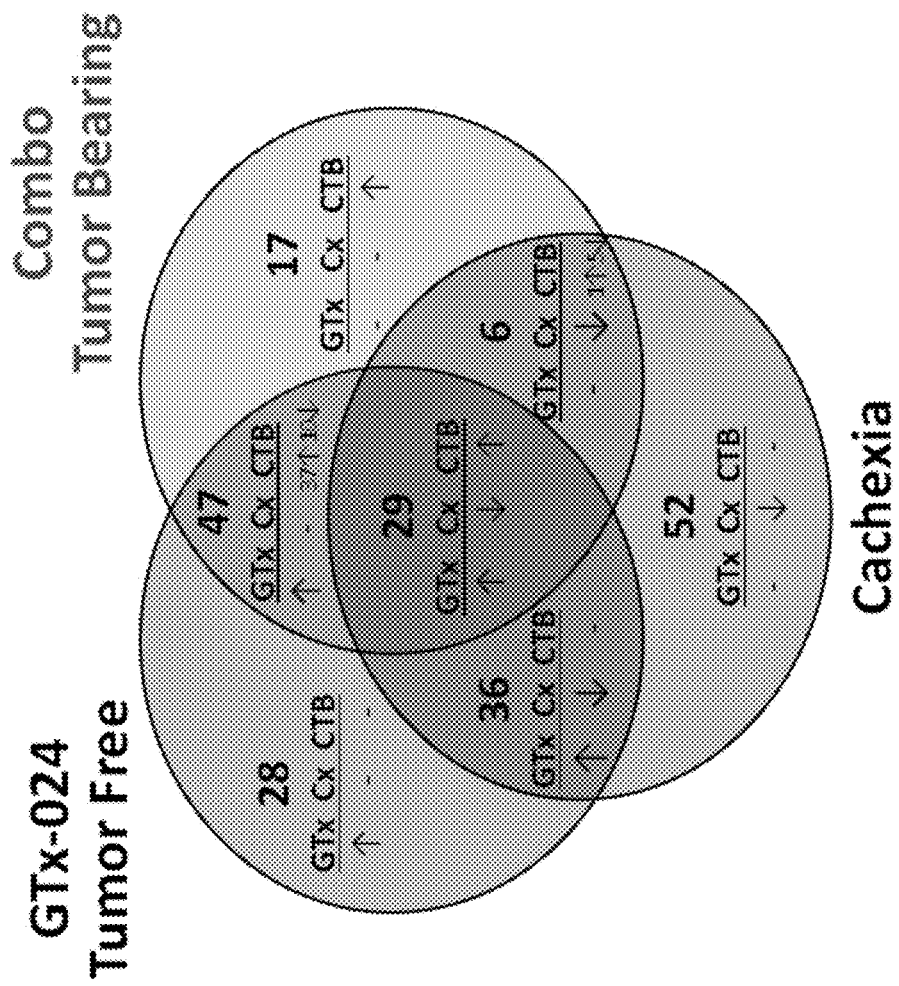
Figure 21:
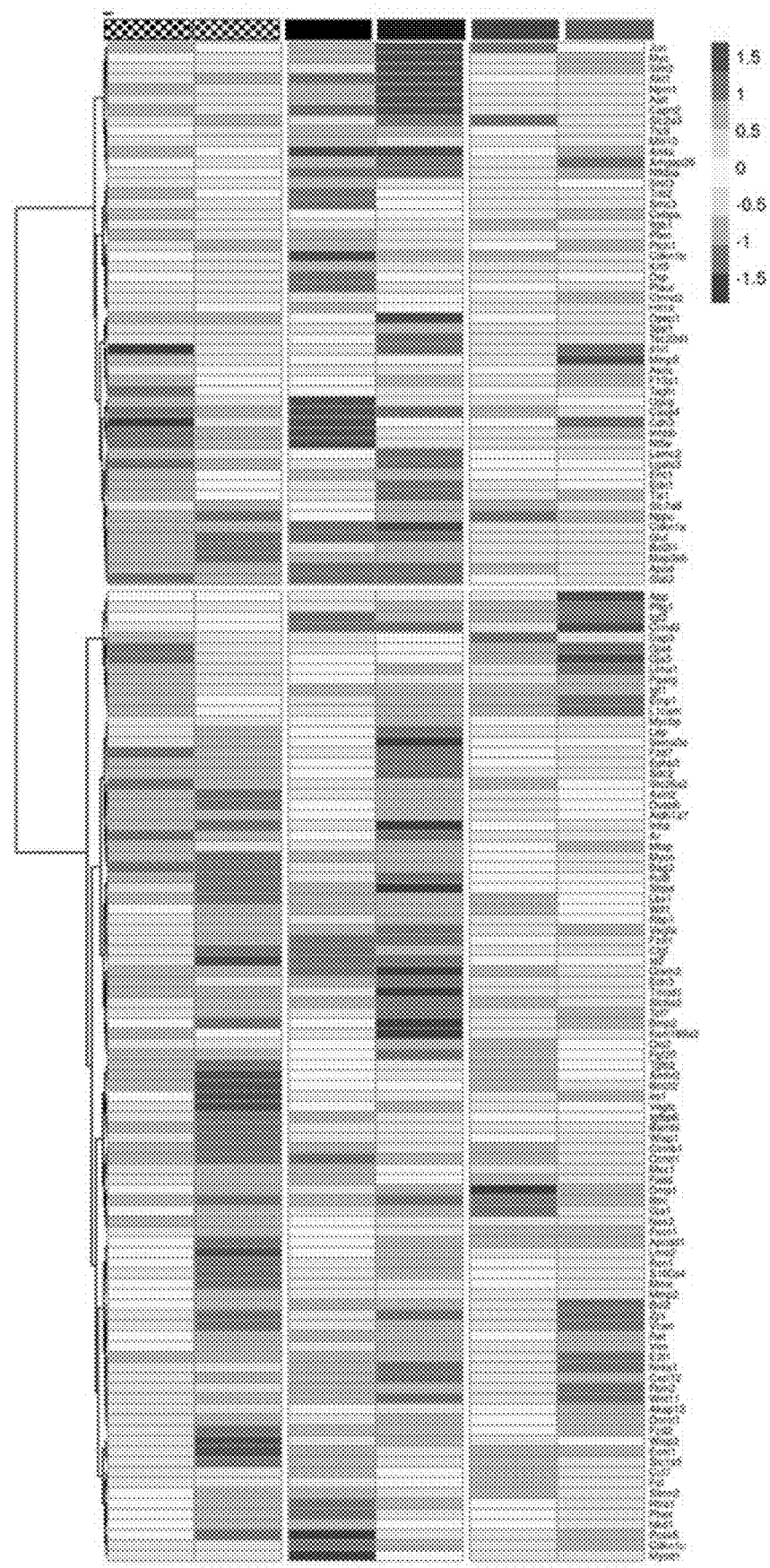
FIG. 21 is a heat map of DEGs within the CTNNB1 gene set (mean z score). Tumor-free control, GTx-024-treated tumor-free, tumor-bearing control, GTx-024-treated tumor-bearing, AR-42-treated tumor-bearing, and Combination-treated tumor-bearing.

To better understand GTx-024's contribution to the efficacy apparent in combination-treated mice, the transcriptome of combination-treated gastrocnemius muscle was compared to cachectic controls revealing 2,026 DEGs (or 50.6% of all DEGs) not solely attributable to AR-42 treatment (FIG. 6A). It is possible that GTx-024-mediated anabolic signaling detectable in GTx-024-treated tumor-free controls would be diminished in tumor-bearing GTx-024-treated animals in the absence of AR-42. Though very few DEGs were apparent in GTx-024-treated tumor-free controls (n=27, FIG. 19), GSEA focused on TF pathways revealed abundant coordinated signaling with regulation of 8-catenin (CTNNB1) target genes providing the most significant overlap (FDR <1e-5, FIG. 6B). Coordinate regulation of 8-catenin target genes was not apparent in cachectic controls or following GTx-024 or AR-42 monotherapy, but was again among the most prominent pathways detected by GSEA in combination-treated mice (FDR <1e-5, FIG. 6C). GSEA plots demonstrate a robust pattern of GTx-024-mediated activation of 8-catenin target genes requiring AR-42 co-administration in cachectic mice (FIG. 6D, leftmost panel compared to rightmost panel). Analysis of overlap of the leading edge genes revealed a large number of CTNNB1 genes regulated by both GTx-024 and cachexia versus tumor free controls but in different directions (n=49 middle, 17 bottom left; FIG. 20A). Many fewer leading edge genes were regulated by AR-42 monotherapy but also in an opposite direction to GTx-024 (n=2 middle, 23 top middle; FIG. 20B). However, combined therapy results in a larger leading edge gene set overlap that is regulated in a similar direction to GTx-024 monotherapy (n=29 middle, 37 of 47 top middle; FIG. 20C). This pattern of β-catenin target gene regulation is also apparent when DEG's within the TFACTS_CTNNB1 gene set are visualized across treatment groups (FIG. 21).

Figure 6B:
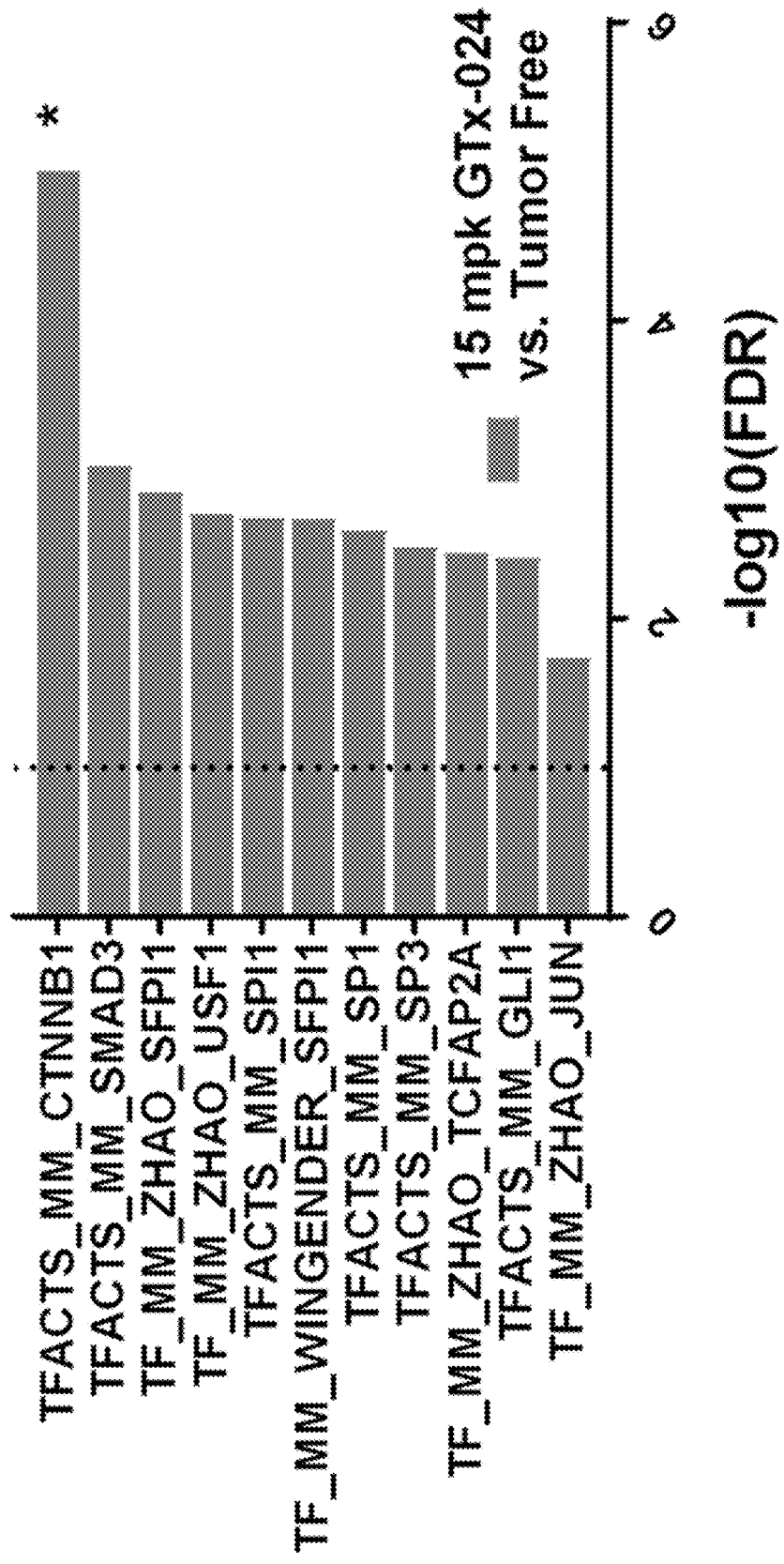
FIG. 6B is a bar graph showing significance values from transcription factor pathway-focused GSEA of GTx-024-treated tumor-free versus tumor-free control transcriptomes. *FDR<1e-5 was determined for the CTNNB1 gene set, and was set to 1e-5 for plot.
Figure 6C:
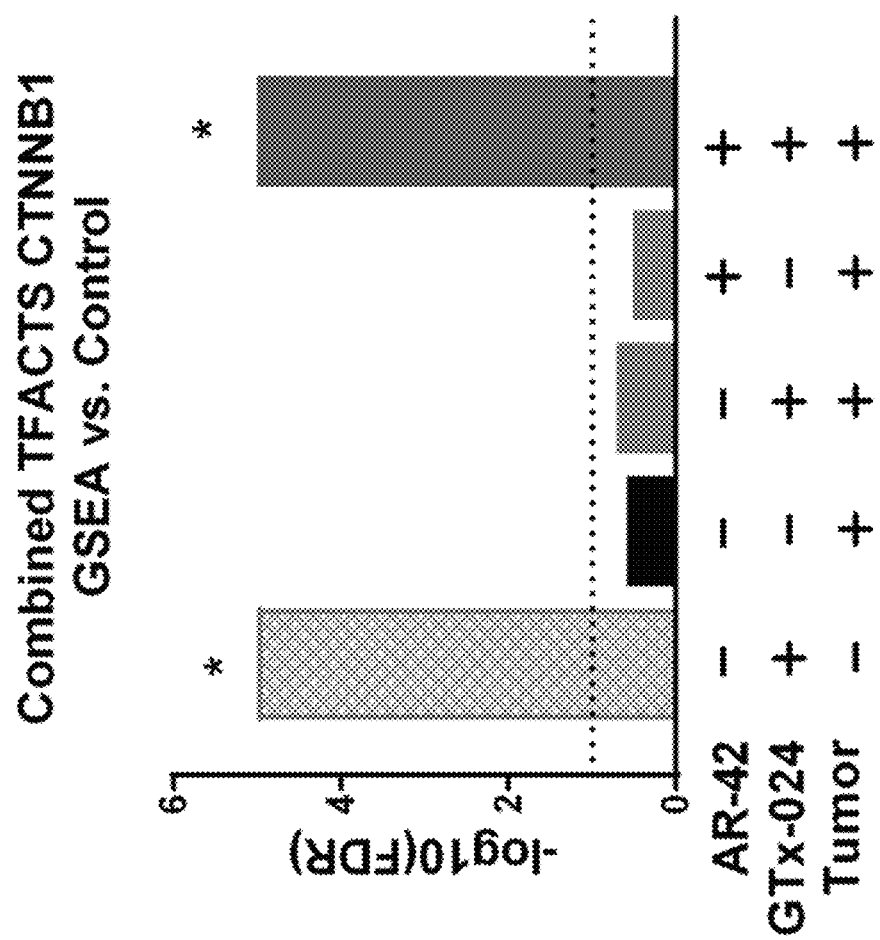
FIG. 6C is a bar graph showing significance values from GSEA using combined CTNNB1 gene sets. Each treatment group was compared to tumor-free control transcriptomes. *FDR<1e-5 determined, set to 1e-5 for plot.
Figure 6D:
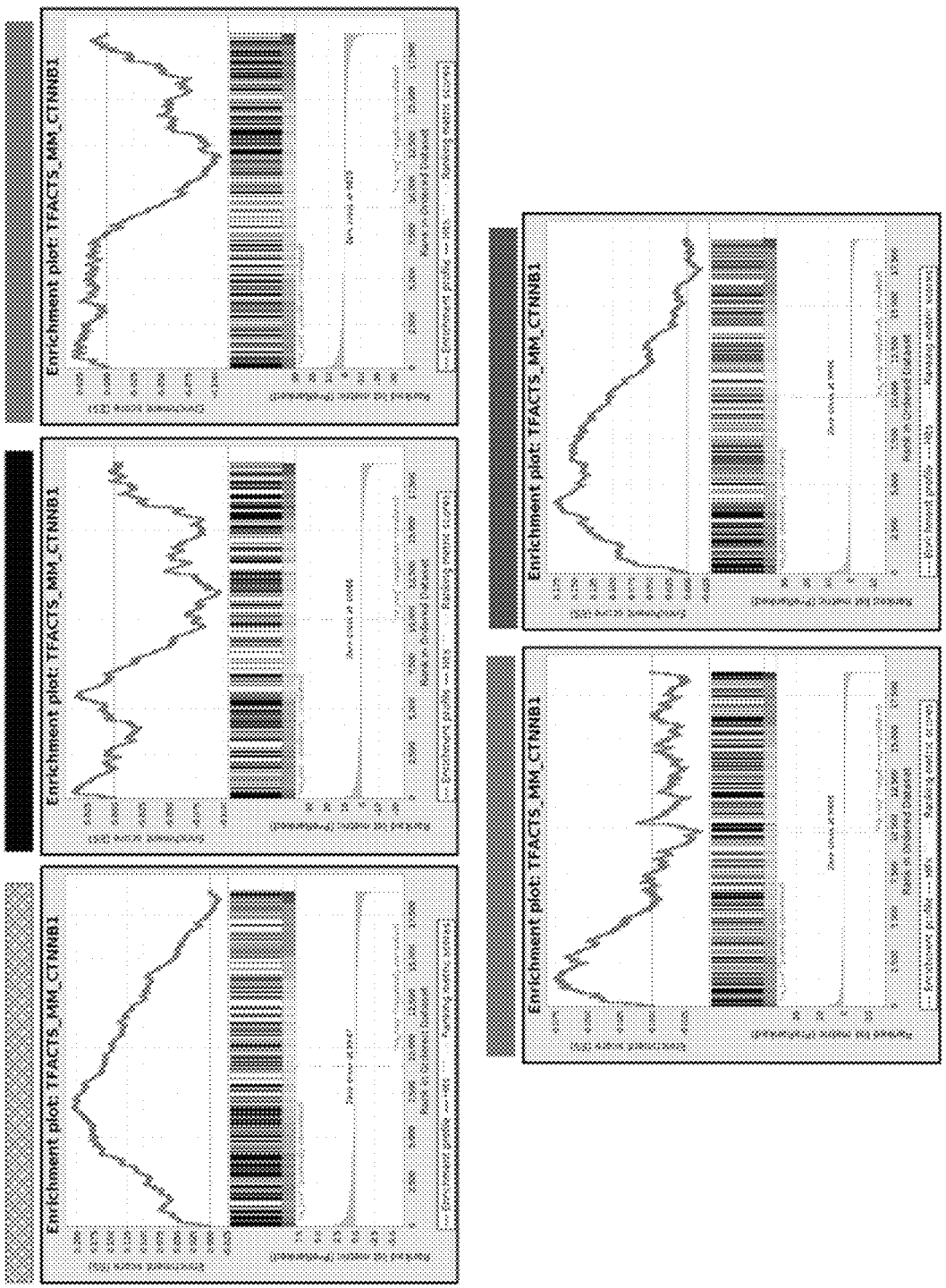
FIG. 6D contains enrichment plots from GSEA of the CTNNB1 gene set for each treatment group versus tumor-free control comparisons. GTx-024-treated tumor-free (blue hatched), tumor-bearing control, GTx-024-treated tumor-bearing, AR-42-treated tumor-bearing, and Combination-treated tumor-bearing.
Figure 6E:
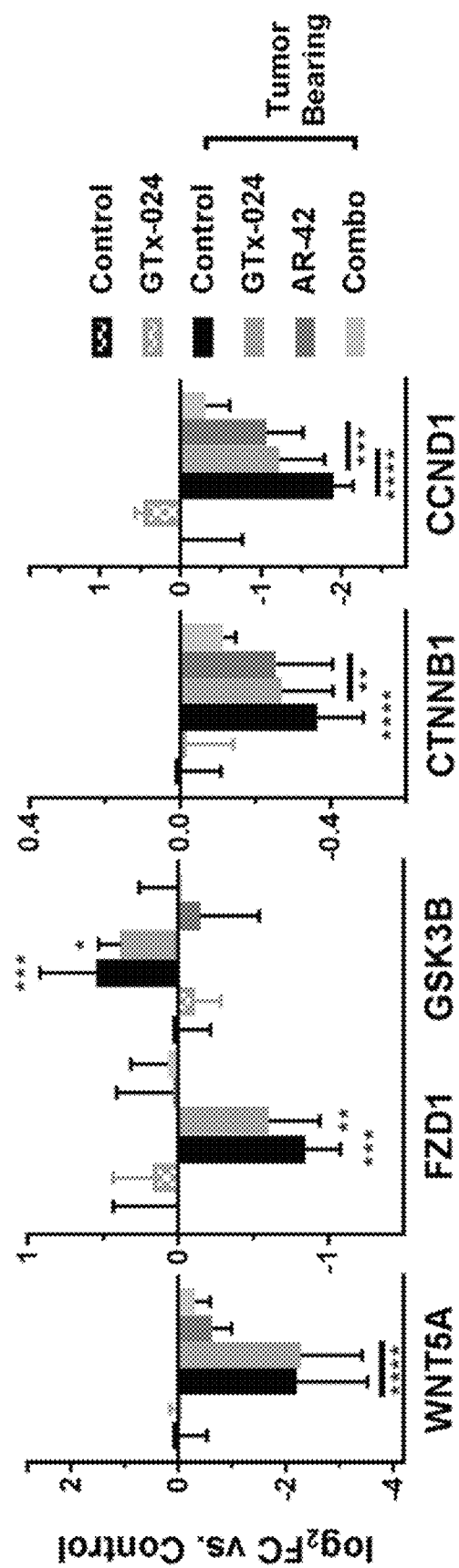
FIG. 6E contains bar graphs showing mRNA expression of WNT effectors upstream of β-catenin. Data are presented as mean±SD of log-transformed fold change (log 2FC) values versus tumor-free controls. *p<0.1, p<0.05, *p<0.01, **p<0.001 based on Benjamini-Hochburg adjusted pvalues from DESeq2.
Figure 6F:
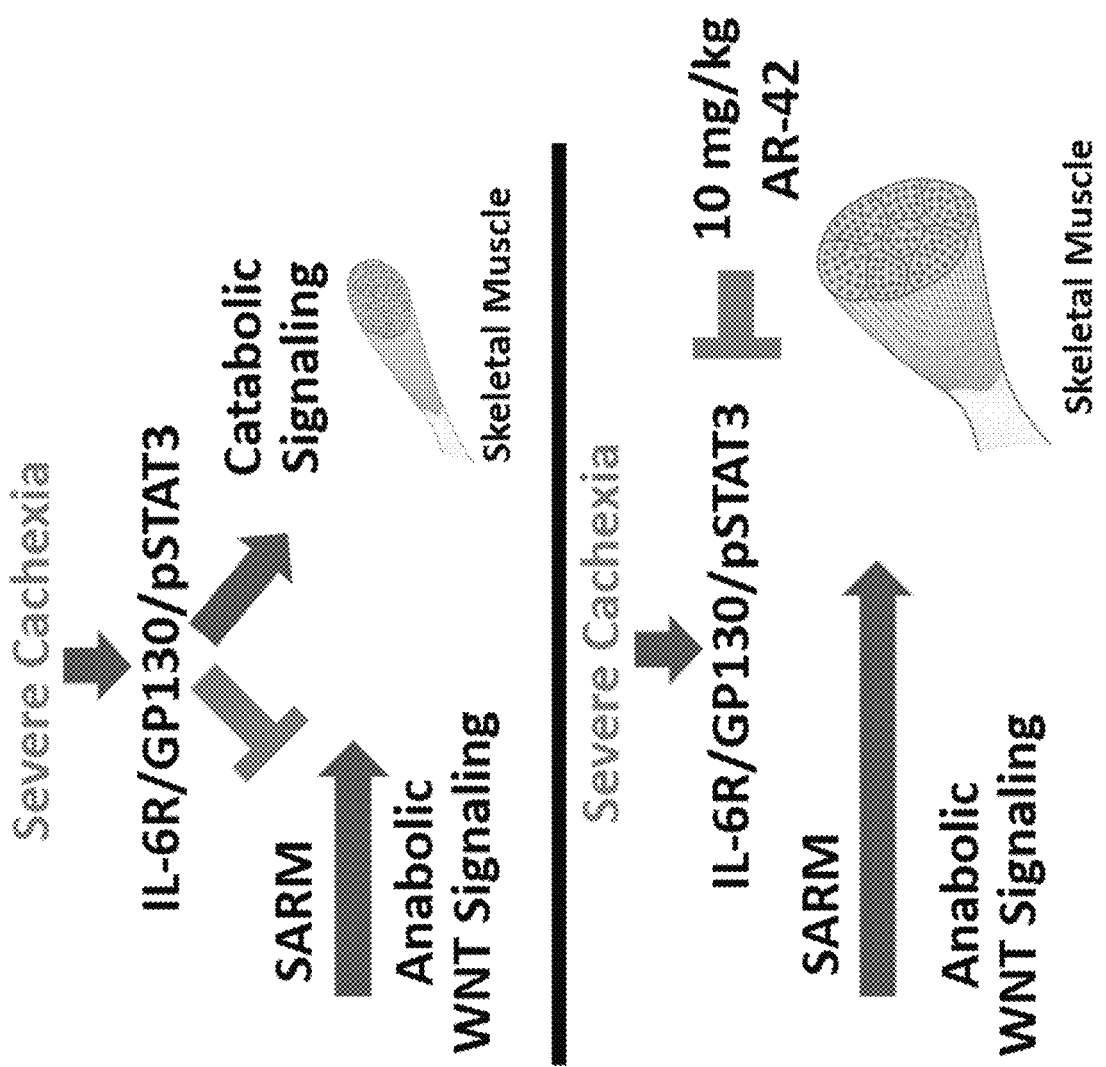
FIG. 6F**) is an illustration of a Graphical Mechanistic Hypothesis.

Expression of the canonical skeletal muscle WNT agonist Wnt5a (WNTSA), canonical WNT receptor Fzd1 (FZD1) and 8-catenin itself (CTNNB1) were all reduced with C26 tumor burden, whereas the negative regulator of 8-catenin, GSK3B, was up-regulated (FIG. 6E). In each case, GTx-024 monotherapy in tumor-bearing mice failed to restore expression to tumor-free control levels. However, with the exception of β-catenin, AR-42 treatment effectively reversed tumor-induced regulation. Furthermore, combination treatment alone restored β-catenin and the well-characterized β-catenin target gene cyclin D1 (CCND1) (Shtutman M, et al. Proc Natl Acad Sci USA. 1999 96(10):5522-7) expression to tumor-free control levels. Taken together these data provide strong support for: 1) the dependence of GTx-024's anabolic effects in skeletal muscle on functional WNT/β-catenin signaling; 2)C-26 tumor burden's ability to disrupt WNT/β-catenin signaling in skeletal muscle; and 3) AR-42's ability to restore WNT/β-catenin responsiveness to treatment with GTx-024.

Discussion

Anti-Cachectic Efficacy of Reduced Dose 10 mg/kg AR-42

AR-42 is currently under clinical evaluation as a direct anti-tumor agent (NCT02282917, NCT02795819, NCT02569320). Recent clinical experience suggested the previously described 50 mg/kg anti-cachectic dose in mice would be poorly tolerated and inconsistent with administration to already heavily treated cachectic cancer patients. Described herein is a 5-fold AR-42 dose reduction that retained anti-cachectic efficacy across multiple studies (FIG. 2 and FIG. 9). Preliminary enrichment analyses of AR-42-regulated transcripts in muscle implicated IL-6 and immune system signaling in the anti-cachectic efficacy of AR-42 (FIG. 11). However, at this reduced dose of AR-42, circulating cytokines were not significantly modulated by AR-42 treatment (FIG. 4A and Table 1By contrast, activation of STAT3, an essential mediator of IL-6 family cytokine-derived immune signals, was AR-42-sensitive in skeletal muscle (FIG. 4D). IL-6 family cytokine signaling through STAT3, as opposed to FOXO, NFKB, SMAD or C/EBP transcription, drives C2C12 myotube atrophy in response to C-26 cell conditioned media (Seto D N, et al. J Biol Chem. 2015 290(32):19976-86). In agreement with the critical role of STAT3 activation in C-26-mediated cachexia, both genetic manipulation and pharmacological inhibition of STAT3 mitigate C-26 tumor-induced losses in skeletal muscle (Silva K A, et al. J Biol Chem. 2015 290(17):11177-87; Seto D N, et al. J Biol Chem. 2015 290(32):19976-86). Transcriptomic analyses of gastrocnemius muscle confirmed the ability of reduced dose AR-42 to markedly impact cachexia-associated transcription (FIG. 5A) and substantiated STAT3 and ATF-1 transcriptional programs as cachectic drivers (FIG. 5B). ATF-1 is a member of the cAMP response element-binding protein (CREB) family of TFs whose activation is associated with fibroblast proliferation and transformation, but has no described role in muscle wasting (Zheng D, et al. Cancer Res. 2008 68(18):7650-60). AR-42 treatment reduced the expression of IL-6RA and the effector protein GP130 (Figure similar to reports of AR-42 activity in multiple myeloma cells (Zhang S, et al. Int J Cancer. 2011 129(1):204-13) and the activity of pan-HDACi's in naïve CD4+ T cells (Glauben R, et al. J Biol Chem. 2014 289(9): 6142-51). Tissue-specific HDACi-mediated muting of IL-6R and/or GP130 induction following cachectic challenge provides a plausible mechanism for the reversal of IL-6 family cytokine-driven ATF-1/STAT3 transcription (FIGS. 5D and 5F) detected in the absence of broader systemic immune effects (FIG. 4).

Impact of C-26 Tumor Burden on Androgen Signaling

A key finding of this report is the extent of resistance to anabolic androgen administration in the C26-model of cancer cachexia. Fully anabolic doses of two SARMS and a potent steroidal androgen, administered orally (GTx-024) and parenterally (TFM-4AS-1, DHT), resulted in no detectable anti-cachectic efficacy (FIG. 2), despite demonstrated anabolic capability and evidence of systemic hormonal activity (FIG. 8A).

Androgens have a well characterized ability to normalize skeletal muscle catabolic gene expression associated with either glucocorticoid (dexamethasone)- or hypogonadism (castration)-induced atrophy (Jones A, et al. Endocrinology. 2010 151(8):3706-19; White J P, et al. Mol Cell Endocrinol. 2013 365(2):174-86; Serra C, et al. Endocrinology. 2013 154(12):4594-606). It is possible that the inability of androgens to reverse C-26 tumor-mediated atrogene expression underlies their lack of efficacy (FIG. 3A). Consistent with this hypothesis, inflammatory cytokine-driven catabolic signaling in the C-26-model, which is mechanistically distinct from androgen-responsive wasting, appears completely insensitive to androgen administration (FIG. 5). A plausible explanation for androgens' ineffectiveness as a monotherapy is a cachexia-mediated direct disruption of AR signaling. However, the response of the hypothalamic-pituitary-gonadal axis (FIG. 8A), several cytokines (FIG. 4A) and gastrocnemius transcriptome (FIG. 14) to androgen, along with no obvious effects of tumor burden on AR mRNA or protein (FIGS. 3B and C), suggests the AR's ability to respond to androgen in skeletal muscle remains intact. Nonetheless, catabolic signaling through the IL-6/GP130/STAT3 axis appears refractory to diverse androgen administration.

In addition to mitigating catabolic proteasomal signaling, androgens have well-characterized direct anabolic effects on skeletal muscle that include targeting MUSCs and pluripotent mesenchymal progenitor cells to promote muscle hypertrophy (Dubois V, et al. Cell Mol Life Sci. 2012 69(10): 1651-67). Is is possible that compromised androgen-mediated anabolic signaling might contribute to GTx-024's lack of anti-cachectic efficacy. For consistency across studies, all of the mechanistic analyses focused on gastrocnemius muscle which, like most skeletal muscles, has scant AR expression (FIG. 3A). It readily responds to androgen administration (Serra C, et al. Endocrinology. 2013 154(12): 4594-606). As such, GTx-024 treatment in tumor-free mice resulted in very few DEGs (FIG. 19A) but GSEA, which is designed to detect patterns within whole transcriptomes, as opposed to individual DEGs (Subramanian A, et al. Proc Natl Acad Sci USA. 2005 102(43):15545-50), revealed a robust induction of β-catenin target gene regulation (FIG. 6B-D). The disclosed results are consistent with androgen-mediated β-catenin activation reported in the context of whole muscle tissue (Gentile M A, et al. J Mol Endocrinol. 2010 44(1):55-73), and as a requirement for myogenic differentiation of pluripotent mesenchymal cells (Singh R, et al. Endocrinology. 2009 150(3):1259-68). Notably, GTx-024-mediated β-catenin target gene regulation is completely abrogated in the context of C26-tumor burden (FIG. 6C-D), which corresponds with coordinated suppression of canonical WNT pathway effectors (FIG. 6E). GTx-024-mediated β-catenin activation was only restored in the presence of AR-42 which, as a monotherapy, normalized WNT effector expression.

Disclosed herein is dysfunctional skeletal muscle WNT signaling in experimental cachexia. Cachexia was associated with suppression of canonical WNT effectors (FIG. 6E) and an inability to respond to androgen-mediated WNT signals (FIG. 6D). Multiple β-catenin target genes did respond to cachectic signaling (FIGS. 20 and 21), suggesting that components of WNT-mediated β-catenin target gene regulation remain intact despite the suppression of upstream WNT effectors. Importantly, both constitutive activation and genetic abrogation of WNT signaling impair proper adult muscle satellite cells ("MUSC") function in response to injury (Rudolf A, et al. Cell Rep. 2016 15(6):1277-90; Otto A, et al. J Cell Sci. 2008 121(Pt 17):2939-50; Agley C C, et al. Sci Rep. 2017 7(1):13189). The provided data suggest tightly controlled WNT-signaling is lost in tumor-bearing mice. This is consistent with other reports of MUSC dysfunction in the C-26 model (He W A, et al. J Clin Invest. 2013 123(11):4821-35). Intriguingly, β-catenin-mediated follistatin (FST) induction is required to promote MUSC differentiation following stimulation with WNT ligands (Jones A E, et al. Skelet Muscle. 2015 5:14) and androgens (Braga M, et al. Mol Cell Endocrinol. 2012 350(1):39-52). Given the clear effects of exogenous androgen administration on MUSC activation (Sinha-Hikim I, et al. Am J Physiol Endocrinol Metab. 2003 285(1):E197-205), it is plausible that cachexia-mediated disruption of WNT signaling represents a functional blockade of androgenic anabolism in skeletal muscle (FIG. 6G). Furthermore, intact WNT signaling is required for proper MUSC function irrespective of androgen administration, suggesting the dysfunctional WNT signaling reported here might be linked more broadly to the important clinical problem of cancer-induced anabolic resistance (Hardee J P, et al. Oxid Med Cell Longev. 2017 2017:8018197).

Combined Anabolic and Anti-Catabolic Therapy in Cancer Cachexia

Disclosed herein is the combination of SARM and HDAC inhibitor administration in experimental cachexia, which demonstrated efficacy using two agents currently undergoing clinical development. Even with the limited treatment window available in the C-26 model, there was improved total body weight (FIG. 2A, D), lower limb skeletal muscle mass (FIG. 2B, E), and grip strength (FIG. 2C, F) for two different SARMs when combined with AR-42 over tumor-bearing controls and SARM monotherapy. Transcriptome characterization of skeletal muscle tissue revealed the ability of AR-42, but not GTx-024, to ameliorate IL-6/GP130/STAT3-mediated catabolic signaling, whereas GTx-024, but not AR-42, stimulated anabolic canonical WNT signaling. Strikingly, GTx-024's ability to effectively stimulate WNT signaling required AR-42 co-treatment in cachectic mice. Notably, when AR-42 was combined with DHT (FIG. 2D), terminal body weights were significantly improved compared to single agent AR-42 treatment. The mechanistic support for beneficial signaling in muscle following SARM and HDACi co-administration along with DHT's in vivo efficacy suggests that similar results are possible with optimized combination SARM regimens.

Despite established efficacy in diverse patient populations (Dobs A S, et al. Lancet Oncol. 2013 14(4):335-45; Dalton J T, et al. J Cachexia Sarcopenia Muscle. 2011 2(3):153-61), GTx-024 failed to provide anabolic benefit in advanced NSCLC patients (Crawford J. Curr Opin Clin Nutr Metab Care. 2016 19(3):199-204). Though weight loss was not required for enrollment in GTx-024's registration trials, roughly half of all patients reported >5% unexplained weight loss at initiation of chemotherapy suggesting a high prevalence of cachexia at diagnosis. In a similar cohort receiving anabolic ghrelin mimetic anamorelin therapy, subgroup analyses revealed patients with body mass indices <18.5 (and presumably severe cachexia) showed no improvements in body composition (Temel J S, et al. Lancet Oncol. 2016 17(4):519-31). Analogous to these clinical populations, the provided data show that anabolic androgen administration cannot overcome severe catabolic signaling in the C-26 model and that profound cachectic burden additionally results in a blockade of critical anabolic signaling. Furthermore, AR-42's anti-cachectic efficacy involves both mitigating catabolic signaling and licensing anabolic signaling providing compelling mechanistic support for combined GTx-024/AR-42 administration in cachectic patients. Combination therapy demonstrates the potential to improve anabolic response in patient populations with advanced cancer wasting.

TABLE 1

Serum Cytokine Panel-Complete Results. Multiplex analysis of diverse serum cytokinesa at Day 17 sacrifice from Study 2.[b]

| | Tumor-free | | C-26 Tumor-bearing | | | |
|---|---|---|---|---|---|---|
| | Vehicle | GTx-024 | Vehicle | GTx-024 | AR-42 | Combo |
| Eotaxin | 715.35 ± 120.63 | 669.53 ± 100.70 | 846.40 ± 222.70 | 876.82 ± 100.53 | 735.73 ± 110.62 | 754.99 ± 93.28 |
| G-CSF | 248.66 ± 64.60* | 338.39 ± 71.70* | 12164.11 ± 18944.48 | 2446.63 ± 1625.70* | 2782.18 ± 2191.30 | 1674.20 ± 1160.74* |
| GM-CSF | 18.71 ± 5.56 | 13.27 ± 4.62* | 21.92 ± 5.36 | 17.35 ± 4.33 | 18.70 ± 3.77 | 20.58 ± 5.40 |
| IFNg | 7.19 ± 2.69 | 5.93 ± 2.14 | 4.44 ± 2.58 | 4.12 ± 2.09 | 4.69 ± 1.11 | 3.31 ± 1.85 |
| IL-1a | 228.75 ± 279.11 | 60.41 ± 56.12 | 82.77 ± 61.73 | 167.80 ± 156.50 | 143.31 ± 157.59 | 58.77 ± 40.43 |
| IL-1b | 11.26 ± 9.64 | 14.65 ± 5.66 | 15.22 ± 8.72 | 12.12 ± 5.54 | 20.48 ± 6.25 | 10.31 ± 6.93 |
| IL-2 | 18.51 ± 11.07 | 15.43 ± 6.56 | 20.81 ± 14.87 | 15.62 ± 3.41 | 19.37 ± 6.07 | 13.74 ± 4.30 |
| IL-3 | 1.73 ± 0.77 | 1.10 ± 0.63 | 10.24 ± 24.68 | 0.92 ± 0.56 | 0.72 ± 0.83 | 0.85 ± 0.44 |
| IL-4 | 0.98 ± 0.94 | 0.48 ± 0.37 | 0.35 ± 0.21 | 0.23 ± 0.14 | 0.32 ± 0.19 | 0.27 ± 0.08 |
| IL-5 | 7.12 ± 1.97 | 5.71 ± 3.26 | 2.18 ± 1.78 | 1.11 ± 0.66 | 5.50 ± 4.41 | 9.23 ± 10.44 |
| IL-6 | 3.35 ± 1.51* | 2.45 ± 1.31* | 537.66 ± 417.18 | 397.54 ± 341.43 | 256.59 ± 183.1 | 448.16 ± 294.52 |
| IL-7 | 14.18 ± 8.61 | 11.51 ± 11.06 | 11.01 ± 5.26 | 11.19 ± 8.17 | 41.51 ± 99.92 | 63.39 ± 146.65 |
| IL-9 | 14.87 ± 10.69 | 8.02 ± 6.78 | 10.30 ± 8.93 | 8.69 ± 9.43 | 11.28 ± 7.68 | 12.25 ± 8.35 |
| IL-10 | 12.22 ± 5.83 | 2.38 ± 1.13 | 11.14 ± 12.03 | 14.15 ± 18.01 | 15.13 ± 11.16 | 11.37 ± 8.75 |
| IL12 (p40) | 41.84 ± 32.05 | 22.48 ± 13.42 | 24.13 ± 19.98 | 27.61 ± 27.95 | 31.22 ± 24.43 | 17.07 ± 20.10 |
| IL-12 (p70) | 27.70 ± 19.35 | 10.83 ± 6.12 | 17.42 ± 15.14 | 12.62 ± 7.71 | 10.16 ± 6.16 | 9.34 ± 2.66 |
| IL-13 | 33.94 ± 8.04 | 29.87 ± 12.81 | 34.04 ± 9.17 | 31.63 ± 8.22 | 34.19 ± 8.29 | 31.96 ± 8.08 |
| IL-15 | 103.31 ± 50.35 | 131.33 ± 70.97 | 84.16 ± 54.06 | 97.32 ± 39.18 | 51.57 ± 19.99 | 517.81 ± 1308.98 |
| IL-17 | 3.04 ± 2.26 | 5.01 ± 1.18* | 1.30 ± 0.57 | 1.75 ± 1.28 | 1.82 ± 0.85 | 2.11 ± 1.21 |
| IP-10 | 162.64 ± 43.04 | 145.68 ± 48.83* | 238.29 ± 124.78 | 154.76 ± 17.98* | 215.35 ± 52.46 | 227.77 ± 45.23 |
| KC | 65.92 ± 26.47 | 90.02 ± 17.69 | 326.10 ± 215.79 | 288.89 ± 15.46 | 363.38 ± 200.65 | 1094.01 ± 528.53* |
| LIF | 2.03 ± 2.17* | 2.50 ± 2.34 | 24.51 ± 11.26 | 45.26 ± 21.57* | 15.79 ± 5.15 | 28.08 ± 21.16 |
| LIX | 3254.87 ± 3474.12 | 1316.67 ± 1662.66 | 4211.17 ± 3120.65 | 5234.39 ± 4771.34 | 2515.38 ± 3119.67 | 1663.11 ± 1732.77 |
| MCP-1 | 56.10 ± 28.48 | 54.54 ± 7.47 | 116.59 ± 58.35 | 88.07 ± 24.41 | 91.18 ± 40.23 | 88.57 ± 18.09 |
| M-CSF | 47.72 ± 27.44* | 27.23 ± 10.09 | 23.63 ± 8.29 | 22.23 ± 9.45 | 20.21 ± 4.63 | 21.00 ± 4.19 |
| MIG | 100.03 ± 20.20 | 89.29 ± 41.83 | 42.36 ± 14.76 | 39.33 ± 12.88 | 55.17 ± 10.58 | 90.75 ± 78.56 |
| MIP-1a | 108.48 ± 32.73 | 75.46 ± 29.41 | 119.93 ± 59.04 | 108.03 ± 27.91 | 63.79 ± 19.14 | 67.82 ± 37.92 |
| MIP-1b | 88.59 ± 10.35 | 87.69 ± 10.61 | 89.87 ± 24.41 | 81.67 ± 11.63 | 76.41 ± 12.81 | 83.90 ± 9.08 |
| MIP-2 | 117.91 ± 32.13 | 136.75 ± 47.91 | 139.23 ± 33.21 | 147.63 ± 59.81 | 146.34 ± 32.60 | 105.45 ± 37.15 |
| RANTES | 29.72 ± 8.43 | 20.84 ± 10.38 | 23.70 ± 9.51 | 20.67 ± 4.57 | 19.70 ± 4.31 | 17.64 ± 6.13 |
| TNFa | 12.58 ± 4.75 | 12.15 ± 4.24 | 17.86 ± 19.40 | 12.71 ± 5.12 | 12.77 ± 4.55 | 11.01 ± 2.09 |
| VEGF | 1.05 ± 0.39 | 0.87 ± 0.32 | 1.06 ± 0.27 | 0.87 ± 0.29 | 1.04 ± 0.24 | 0.88 ± 0.22 | apg/ml; Data expressed as mean ± SD
[b]Treatments (p.o., qd): GTx-024 (15 mg/kg); AR-42 (10 mg/kg).
*$p < 0.05$, versus tumor-bearing vehicle-trated controls; One-way ANOVA followed by Dunnett's multiple comparison test.
Eotaxin: chemokine (C-C motif) ligand 11; G-CSF: granulocyte colony-stimulating factor; GM-CSF: granulocyte macrophage colony-stimulating factor; IFNγ: interferon gamma; IL-1a: interleukin-1 alpha; IL-1b: interleukin-1 beta; IL-2: interleukin-2; IL-3: interleukin-3; IL-4: interleukin-4; IL-5: interleukin-5; IL-6: interleukin-6; IL-7: interleukin-7; IL-9: interleukin-9; IL-10: interleukin-10; IL-12 (p40): interleukin-12 subunit p40; IL-12 (p70): interleukin-12 subunit p70; IL-13: interleukin-13; IL-15: interleukin-15; IL-17: interleukin-17; IP-10: interferon gamma-induced protein 10; KC: Chemokine (C-X-C motif) ligand 1; LIF: leukemia inhibitory factor; LIX: chemokine (C-X-C motif) ligand 5; MCP: monocyte chemoattractant protein-1; M-CSF: macrophage colony-stimulating factor; MIG: monokine induced by gammainterferon, chemokine (C-X-C motif) ligand 9; MIP-1a: macrophage inflammatory protein 1 alpha; MIP-1b: macrophage inflammatory protein 1 beta; MIP-2: macrophage inflammatory protein 2; RANTES: regulated upon activation, normally T-expressed, and presumably secreted, chemokine (C-C motif) ligand 5; TNFα: tumer necrosis factor-alpha; VEGF: vascular endothelial growth factor.

TABLE 2

Primer sequences

| Target | Accession Number | Primer Forward (5' to 3') | Reverse (5' to 3') | Amplicon size (bp) | Sequence | Reference |
|---|---|---|---|---|---|---|
| AR | NM_013476.4 | GCCTCCGAAGTGTGGTATCC | CCTGGTACTGTCCAAACGCA | 138 | 2457/2476, 2594/2575 | |
| C/EBPδ | NM_007679.4 | CGACTTCAGCGCCTACATTGA | CTAGCGACAGACCCCACAC | 171 | 216/236 386/368 | Primer Bank ID 31560718a1 |
| Fbxo32/ Atrogin1 | NM_026346.3 | TTCAGCAGCCTGAACTACGA | AGTATCCATGGCGCTCCTTC | 139 | 435/454, 573/554 | |

TABLE 2-continued

Primer sequences

| Target | Accession Number | Primer Forward (5' to 3') | Primer Reverse (5' to 3') | Amplicon size (bp) | Sequence | Reference |
|---|---|---|---|---|---|---|
| Trim63/ MuRF-1 | NM_001039048.2 | GTGACCAAGGAGAATAGCCAC | ATCAGAGCCTCGATGAAGCC | 149 | 693/713, 841/822 | |
| B-actin | NM_001101.3 | CATGTACGTTGCTATCCAGGC | CTCCTTAATGTCACGCACGAT | 250 | 477-497/706-726 | Primer Bank ID 4501885a1 |

TABLE 3

Post-alignment quality control metrics for RNA-seq dataset.

| Metric | Mean | SD | Min | Max |
|---|---|---|---|---|
| Total Reads (R1 + R2) | 44,883,616 | 8,088,060 | 34,227,544 | 67,059,036 |
| Reads After Adaptor Trimming | 43,026,750 | 7,833,050 | 33,101,092 | 65,368,280 |
| Duplicate Reads (%) | 29.8% | 4.3% | 23.1% | 40.5% |
| Mapped Reads (%) | 89.0% | 1.3% | 86.5% | 91.5% |
| Genic Reads (%) | 84.0% | 1.4% | 81.2% | 86.6% |
| Exonic Reads (%) | 82.0% | 1.5% | 79.2% | 84.9% |

Adaptor sequences were trimmed from reads with Trimmomatic prior to alignment to mm10, and post-alignment metrics were calculated with samtools. Bed files used to calculate proportions of genic and exonic reads were obtained from the knownGene table associated with the UCSC Genes track (mm10).

Unless defined otherwise, all technical and scientific terms used herein have the same meanings as commonly understood by one of skill in the art to which the disclosed disclosure belongs. Publications cited herein and the materials for which they are cited are specifically incorporated by reference.

Those skilled in the art will recognize, or be able to ascertain using no more than routine experimentation, many equivalents to the specific aspects of the disclosure described herein. Such equivalents are intended to be encompassed by the following claims.

What is claimed is:

1. A method for treating cancer cachexia in a subject, comprising administering to the subject a therapeutically effective amount of
AR-42, having the following chemical structure:

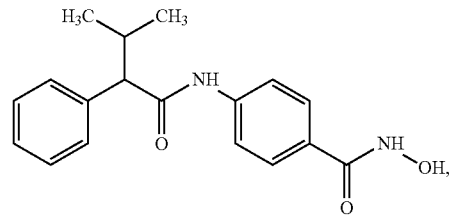 [SMILES: CC(C)C(C(=O)Nc1ccc(C(=O)NO)cc1)c1ccccc1]

and
a class I/IIB HDAC inhibitor and an androgen receptor modulator.

2. The method of claim 1, wherein the subject has been diagnosed as having cancer cachexia.

3. The method of claim 1, wherein the androgen receptor modulator is an anabolic androgenic steroid (AAS), a steroidal androgen, a non-steroidal, selective androgen receptor modulators (SARMs), or combinations thereof.

* * * * *